(12) United States Patent
Prisbrey et al.

(10) Patent No.: US 10,254,204 B2
(45) Date of Patent: *Apr. 9, 2019

(54) MEMBRANE-ASSISTED PURIFICATION

(71) Applicant: Accelerate Diagnostics, Inc., Tucson, AZ (US)

(72) Inventors: Landon Prisbrey, Tucson, AZ (US); Elise Blackmore, Tucson, AZ (US); Kenneth R. Hance, Tucson, AZ (US); Steven W. Metzger, Tucson, AZ (US); Kevin Marshall, Tucson, AZ (US)

(73) Assignee: Accelerate Diagnostics, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/586,132

(22) Filed: May 3, 2017

(65) Prior Publication Data

US 2017/0234781 A1 Aug. 17, 2017

Related U.S. Application Data

(63) Continuation-in-part of application No. 15/236,021, filed on Aug. 12, 2016, which is a continuation of
(Continued)

(51) Int. Cl.
*A61K 39/12* (2006.01)
*G01N 1/40* (2006.01)
(Continued)

(52) U.S. Cl.
CPC .............. *G01N 1/40* (2013.01); *B03C 5/005* (2013.01); *C12M 47/12* (2013.01); *C12N 13/00* (2013.01);
(Continued)

(58) Field of Classification Search
None
See application file for complete search history.

(56) References Cited

U.S. PATENT DOCUMENTS

| 2,666,355 A | 1/1954 | Trurnit |
| 3,493,772 A | 2/1970 | Daughters, II et al. |

(Continued)

FOREIGN PATENT DOCUMENTS

| AU | 772760 | 5/2004 |
| EP | 0498920 | 8/1992 |

(Continued)

OTHER PUBLICATIONS

Magnúsdóttir et al. (Collection of Capillary Electrophoresis Fractions on a Moving Membrane. From: Methods in Molecular Biology, vol. 162: Capillary Electrophoresis of Nucleic Acids, vol. 1: Introduction to the Capillary Electrophoresis of Nucleic Acids. 2001; 323-331).*

(Continued)

*Primary Examiner* — Janet L Andres
*Assistant Examiner* — Stuart W Snyder
(74) *Attorney, Agent, or Firm* — Klarquist Sparkman, LLP

(57) ABSTRACT

Methods and systems for purifying one or more microbial cells and/or viruses from a biological sample are provided. The biological sample is added to a well disposed in a medium. A potential is applied across the medium to cause the contaminants to enter one or more walls of the well, and retain the microbial cells and/or viruses in the well. The microbial cells and/or viruses can be removed from the well, and optionally adhered or fixed to a surface, or detected. In one embodiment, the microbial cells and/or viruses are retained in the well by embedding in the medium. The medium including the embedded microbial cells and/or (Continued)

viruses may be excised or otherwise removed and transferred to a glass slide or other solid surface. In some examples, a biological sample containing contaminants and one or more microbial cells is introduced to a well disposed in a porous filter medium, wherein the porous filter medium includes pores smaller than the one or more microbial cells, thereby preventing the one or more microbial cells from entering the porous filter medium.

18 Claims, 21 Drawing Sheets

Related U.S. Application Data application No. 14/004,145, filed as application No. PCT/US2012/028139 on Mar. 7, 2012, now Pat. No. 9,434,937.

(60) Provisional application No. 61/449,824, filed on Mar. 7, 2011.

(51) Int. Cl.
  B03C 5/00 (2006.01)
  C12N 13/00 (2006.01)
  G01N 33/49 (2006.01)
  C12M 1/00 (2006.01)
  C12Q 1/02 (2006.01)
  C12Q 1/24 (2006.01)
  G01N 1/34 (2006.01)
  G02B 21/36 (2006.01)
  C12N 7/00 (2006.01)

(52) U.S. Cl.
  CPC ............... *C12Q 1/02* (2013.01); *C12Q 1/24* (2013.01); *G01N 1/34* (2013.01); *G01N 33/491* (2013.01); *G02B 21/367* (2013.01); *B03C 2201/26* (2013.01); *C12N 7/00* (2013.01); *C12N 2710/00051* (2013.01); *G01N 2001/4038* (2013.01)

(56) References Cited

U.S. PATENT DOCUMENTS

| | | |
|---|---|---|
| 3,532,790 A | 10/1970 | Greenberg et al. |
| 3,637,313 A | 1/1972 | Upatnieks |
| 3,792,081 A | 2/1974 | Higuchi et al. |
| 3,811,036 A | 5/1974 | Perry |
| 3,832,532 A | 8/1974 | Praglin et al. |
| 3,854,480 A | 12/1974 | Zaffaroni |
| 3,904,293 A | 9/1975 | Gee |
| 3,926,564 A | 12/1975 | Giaever |
| 3,935,073 A | 1/1976 | Waters |
| 3,938,515 A | 2/1976 | Leeper et al. |
| 3,957,362 A | 5/1976 | Mancini et al. |
| 3,961,628 A | 6/1976 | Arnold |
| 4,069,307 A | 1/1978 | Higuchi et al. |
| 4,070,248 A | 1/1978 | Schmidt |
| 4,076,591 A | 2/1978 | Heden |
| 4,136,250 A | 1/1979 | Mueller et al. |
| 4,199,449 A | 4/1980 | Slejko |
| 4,199,499 A | 4/1980 | Smithwick, Jr. et al. |
| 4,200,493 A | 4/1980 | Wilkins et al. |
| 4,220,152 A | 9/1980 | Dresback |
| 4,224,439 A | 9/1980 | Ayers et al. |
| 4,233,847 A | 11/1980 | Walker |
| 4,246,343 A | 1/1981 | Wilkins et al. |
| 4,259,442 A | 3/1981 | Gayral |
| 4,282,287 A | 8/1981 | Giese |
| 4,288,543 A | 9/1981 | Sielaff et al. |
| 4,313,734 A | 2/1982 | Leuvering |
| 4,325,910 A | 4/1982 | Jordan |
| 4,330,440 A | 5/1982 | Ayers et al. |
| 4,332,476 A | 6/1982 | Stenberg et al. |
| 4,351,337 A | 9/1982 | Sidman |
| 4,357,142 A | 11/1982 | Schall, Jr. et al. |
| 4,363,634 A | 12/1982 | Schall, Jr. |
| 4,383,757 A | 5/1983 | Phillips |
| 4,390,343 A | 6/1983 | Walter |
| 4,423,099 A | 12/1983 | Mueller et al. |
| 4,450,150 A | 5/1984 | Sidman |
| RE31,712 E | 10/1984 | Giese |
| 4,478,822 A | 10/1984 | Haslam et al. |
| 4,478,914 A | 10/1984 | Giese |
| 4,481,137 A | 11/1984 | Ohnishi et al. |
| 4,487,839 A | 12/1984 | Kamentsky |
| 4,500,778 A | 2/1985 | Kusaka et al. |
| 4,508,832 A | 4/1985 | Carter et al. |
| 4,509,841 A | 4/1985 | Sakai et al. |
| 4,521,522 A | 6/1985 | Lundstrom et al. |
| 4,537,861 A | 8/1985 | Elings et al. |
| 4,540,881 A | 9/1985 | Hayashi et al. |
| 4,548,890 A | 10/1985 | Mueller et al. |
| 4,548,990 A | 10/1985 | Mueller et al. |
| 4,558,012 A | 12/1985 | Nygren et al. |
| 4,588,624 A | 5/1986 | Nygren et al. |
| 4,613,567 A | 9/1986 | Yasoshima et al. |
| 4,626,674 A | 12/1986 | Oinoue |
| 4,643,968 A | 2/1987 | Weaver |
| 4,655,595 A | 4/1987 | Bjork et al. |
| 4,657,543 A | 4/1987 | Langer et al. |
| 4,661,913 A | 4/1987 | Wu et al. |
| 4,663,296 A | 5/1987 | Revillet et al. |
| 4,693,884 A | 9/1987 | Kleiner et al. |
| 4,693,972 A | 9/1987 | Mansour et al. |
| 4,713,441 A | 12/1987 | Heller et al. |
| 4,716,123 A | 12/1987 | Wood |
| 4,752,567 A | 6/1988 | De Brabander et al. |
| 4,764,342 A | 8/1988 | Kelln et al. |
| 4,772,484 A | 9/1988 | Kitchell et al. |
| 4,778,758 A | 10/1988 | Ericsson et al. |
| 4,805,623 A | 2/1989 | Jobsis |
| 4,814,144 A | 3/1989 | Edelmann et al. |
| 4,857,313 A | 8/1989 | Song et al. |
| 4,876,208 A | 10/1989 | Gustafson et al. |
| 4,877,659 A | 10/1989 | Vince |
| 4,882,168 A | 11/1989 | Casey et al. |
| 4,885,077 A | 12/1989 | Karakelle et al. |
| 4,933,147 A | 6/1990 | Hollar et al. |
| 4,959,301 A | 9/1990 | Weaver et al. |
| 4,993,147 A | 2/1991 | Carpenter et al. |
| 5,002,792 A | 3/1991 | Vegoe |
| RE33,581 E | 4/1991 | Nicoli et al. |
| 5,017,009 A | 5/1991 | Schutt et al. |
| 5,066,465 A | 11/1991 | Kano et al. |
| 5,079,144 A | 1/1992 | Carr et al. |
| 5,079,172 A | 1/1992 | Hari et al. |
| 5,082,630 A | 1/1992 | Partin et al. |
| 5,089,606 A | 2/1992 | Cole et al. |
| 5,149,543 A | 9/1992 | Cohen et al. |
| 5,173,164 A | 12/1992 | Egen et al. |
| 5,196,527 A | 3/1993 | Ookuma et al. |
| 5,208,037 A | 5/1993 | Wright et al. |
| 5,218,039 A | 6/1993 | Stoy et al. |
| 5,239,170 A | 8/1993 | Hughlett |
| 5,240,618 A | 8/1993 | Caldwell et al. |
| 5,288,611 A | 2/1994 | Kohne |
| 5,314,805 A | 5/1994 | Haugland et al. |
| 5,329,461 A | 7/1994 | Allen et al. |
| 5,350,697 A | 9/1994 | Swope et al. |
| 5,405,783 A | 4/1995 | Pirrung et al. |
| 5,466,416 A | 11/1995 | Ghaed et al. |
| 5,468,606 A | 11/1995 | Bogart et al. |
| 5,488,567 A | 1/1996 | Allen et al. |
| 5,491,097 A | 2/1996 | Ribi et al. |
| 5,494,829 A | 2/1996 | Sandstrom et al. |
| 5,496,701 A | 3/1996 | Pollard-Knight |
| 5,556,764 A | 9/1996 | Sizto et al. |
| 5,578,460 A | 11/1996 | Ebersole et al. |
| 5,599,668 A | 2/1997 | Stimpson et al. |
| 5,604,099 A | 2/1997 | Erlich et al. |

(56) References Cited

U.S. PATENT DOCUMENTS

| | | |
|---|---|---|
| 5,622,868 A | 4/1997 | Clarke et al. |
| 5,623,707 A | 4/1997 | Kusaka |
| 5,648,652 A | 7/1997 | Sekiya et al. |
| 5,656,432 A | 8/1997 | Claverys et al. |
| 5,789,173 A | 8/1998 | Peck et al. |
| 5,792,622 A | 8/1998 | Botsford |
| 5,824,494 A | 10/1998 | Feldberg |
| 5,828,716 A | 10/1998 | Bisconte de Saint Julien |
| 5,843,651 A | 12/1998 | Stimpson et al. |
| 5,849,486 A | 12/1998 | Heller et al. |
| 5,863,754 A | 1/1999 | Bajard |
| 5,866,345 A | 2/1999 | Wilding et al. |
| 5,872,013 A | 2/1999 | Leunissen et al. |
| 5,888,760 A | 3/1999 | Godsey et al. |
| 5,922,593 A | 7/1999 | Livingston |
| 5,939,291 A | 8/1999 | Loewy et al. |
| 5,958,704 A | 9/1999 | Starzl et al. |
| 5,976,821 A | 11/1999 | Huston et al. |
| 5,981,268 A | 11/1999 | Kovacs et al. |
| 5,993,634 A | 11/1999 | Simpson et al. |
| 6,017,696 A | 1/2000 | Heller |
| 6,043,048 A | 3/2000 | Johnston et al. |
| 6,051,380 A | 4/2000 | Sosnowski et al. |
| 6,054,270 A | 4/2000 | Southern |
| 6,086,824 A | 7/2000 | Fanning et al. |
| 6,096,272 A | 8/2000 | Clark et al. |
| 6,099,803 A | 8/2000 | Ackley et al. |
| 6,101,946 A | 8/2000 | Martinsky |
| 6,103,479 A | 8/2000 | Taylor |
| 6,107,054 A | 8/2000 | Gibbs |
| 6,122,599 A | 9/2000 | Mehta |
| 6,136,171 A | 10/2000 | Frazier et al. |
| 6,143,247 A | 11/2000 | Sheppard, Jr. et al. |
| 6,153,400 A | 11/2000 | Matsumura et al. |
| 6,153,416 A | 11/2000 | Yuan |
| 6,169,394 B1 | 1/2001 | Frazier et al. |
| 6,176,620 B1 | 1/2001 | Obara |
| 6,214,560 B1 | 4/2001 | Yguerabide et al. |
| 6,221,592 B1 | 4/2001 | Schwartz et al. |
| 6,241,894 B1 | 6/2001 | Briggs et al. |
| 6,242,188 B1 | 6/2001 | Dattagupta et al. |
| 6,245,508 B1 | 6/2001 | Heller et al. |
| 6,251,615 B1 | 6/2001 | Oberhardt |
| 6,251,616 B1 | 6/2001 | Barbera-Guillem et al. |
| 6,251,624 B1 | 6/2001 | Matsumura et al. |
| 6,264,825 B1 | 7/2001 | Blackburn et al. |
| 6,270,953 B1 | 8/2001 | Malcus-Vocanson et al. |
| 6,274,384 B1 | 8/2001 | Starzl et al. |
| 6,290,839 B1 | 9/2001 | Kayyem et al. |
| 6,372,895 B1 | 4/2002 | Bentsen et al. |
| 6,379,897 B1 | 4/2002 | Weidenhammer et al. |
| 6,391,264 B2 | 5/2002 | Hammer et al. |
| 6,391,546 B1 | 5/2002 | Karube et al. |
| 6,391,577 B1 | 5/2002 | Mikkelsen et al. |
| 6,391,937 B1 | 5/2002 | Beuhler et al. |
| 6,395,506 B1 | 5/2002 | Pitner et al. |
| 6,403,367 B1 | 6/2002 | Cheng et al. |
| 6,416,969 B2 | 7/2002 | Matsumura et al. |
| 6,432,694 B1 | 8/2002 | Malmqvist |
| 6,437,551 B1 | 8/2002 | Krulevitch et al. |
| 6,472,166 B1 | 10/2002 | Wardlaw et al. |
| 6,472,228 B2 | 10/2002 | Wang et al. |
| 6,548,263 B1 | 4/2003 | Kapur et al. |
| 6,551,841 B1 | 4/2003 | Wilding et al. |
| 6,565,727 B1 | 5/2003 | Shenderov |
| 6,573,088 B2 | 6/2003 | Gemmell et al. |
| 6,596,532 B1 | 7/2003 | Hyman et al. |
| 6,605,453 B2 | 8/2003 | Ozkan et al. |
| 6,607,888 B2 | 8/2003 | Schwartz et al. |
| 6,611,765 B2 | 8/2003 | Boeufgras et al. |
| 6,642,682 B1 | 11/2003 | Perkins et al. |
| 6,696,286 B1 | 2/2004 | Halverson et al. |
| 6,703,819 B2 | 3/2004 | Gascoyne |
| 6,716,620 B2 | 4/2004 | Bashir et al. |
| 6,809,862 B2 | 10/2004 | Behnsen et al. |
| 6,841,379 B2 | 1/2005 | Matson |
| 6,844,028 B2 | 1/2005 | Mao et al. |
| 6,872,545 B2 | 3/2005 | Griner et al. |
| 6,900,030 B2 | 5/2005 | Pitner et al. |
| 6,951,714 B2 | 10/2005 | Giovannoni et al. |
| 7,067,194 B2 | 6/2006 | Mao et al. |
| 7,108,775 B2 | 9/2006 | Bahatt et al. |
| 7,115,384 B2 | 10/2006 | Clark et al. |
| 7,123,345 B2 | 10/2006 | Sugihara et al. |
| 7,214,299 B2 | 5/2007 | Armstrong |
| 7,250,775 B1 | 7/2007 | Collins et al. |
| 7,258,837 B2 | 8/2007 | Yager et al. |
| 7,306,924 B2 | 12/2007 | Gomez et al. |
| 7,341,841 B2 | 3/2008 | Metzger et al. |
| 7,348,183 B2 | 3/2008 | Fritsch et al. |
| 7,397,540 B2 | 7/2008 | Lundgren et al. |
| 7,413,891 B2 | 8/2008 | Bashir et al. |
| 7,429,355 B2 | 9/2008 | Bishop et al. |
| 7,435,579 B2 | 10/2008 | Bashir et al. |
| 7,451,646 B2 | 11/2008 | Cleland et al. |
| 7,481,977 B2 | 1/2009 | Percival et al. |
| 7,510,637 B2 | 3/2009 | Barlow et al. |
| 7,561,789 B2 | 7/2009 | Border et al. |
| 7,564,245 B2 | 7/2009 | Lee |
| 7,576,307 B2 | 8/2009 | Yazdanfar et al. |
| 7,601,300 B2 | 10/2009 | Blanton et al. |
| 7,622,078 B2 | 11/2009 | Pagés Pinyol |
| 7,629,029 B2 | 12/2009 | Mao et al. |
| 7,642,068 B2 | 1/2010 | Steiner et al. |
| 7,651,837 B2 | 1/2010 | Ohno et al. |
| 7,670,793 B2 | 3/2010 | Glencross |
| 7,678,256 B2 | 3/2010 | Davalos et al. |
| 7,687,239 B2 | 3/2010 | Goldberg et al. |
| 7,689,022 B2 | 3/2010 | Weiner et al. |
| 7,723,095 B2 | 5/2010 | Cleuziat et al. |
| 7,754,148 B2 | 7/2010 | Yu et al. |
| 7,829,275 B2 | 11/2010 | Franzen et al. |
| 7,842,504 B2 | 11/2010 | Devlin, Sr. |
| 7,873,268 B2 | 1/2011 | Segawa et al. |
| 7,901,624 B2 | 3/2011 | Hansen et al. |
| 7,910,062 B2 | 3/2011 | Yu et al. |
| 7,955,555 B2 | 6/2011 | Blecka et al. |
| 8,014,583 B2 | 9/2011 | Zahniser |
| 8,029,746 B2 | 10/2011 | Yu et al. |
| 8,058,078 B2 | 11/2011 | Hansen et al. |
| 8,071,319 B2 | 12/2011 | Metzger et al. |
| 8,102,276 B2 | 1/2012 | Sugiura |
| 8,168,443 B2 | 5/2012 | Yu et al. |
| 8,178,602 B2 | 5/2012 | Mao et al. |
| 8,188,438 B2 | 5/2012 | La |
| 8,304,245 B2 | 11/2012 | Kuypers et al. |
| 8,323,466 B2 | 12/2012 | Kim et al. |
| 8,329,437 B1 | 12/2012 | Ayliffe |
| 8,335,393 B2 | 12/2012 | Kotani |
| 8,354,307 B2 | 1/2013 | Lee |
| 8,361,298 B2 | 1/2013 | Sabin et al. |
| 8,361,299 B2 | 1/2013 | Sabin et al. |
| 8,364,409 B2 | 1/2013 | Rieder et al. |
| 8,368,964 B2 | 2/2013 | Xu et al. |
| 8,372,353 B2 | 2/2013 | Lee et al. |
| 8,372,600 B2 | 2/2013 | Sachs et al. |
| 8,391,582 B2 | 3/2013 | Weiner et al. |
| 8,421,484 B2 | 4/2013 | Prodan et al. |
| 8,460,887 B2 | 6/2013 | Goldberg et al. |
| 8,478,445 B2 | 7/2013 | Hansen et al. |
| 8,481,281 B2 | 7/2013 | Demirev et al. |
| 8,508,652 B2 | 8/2013 | Albu et al. |
| 8,512,636 B2 | 8/2013 | Blanton et al. |
| 8,513,001 B2 | 8/2013 | Weiss et al. |
| 8,563,298 B2 | 10/2013 | Lowery, Jr. et al. |
| 8,603,769 B2 | 12/2013 | Feng et al. |
| 8,614,056 B2 | 12/2013 | Davis et al. |
| 8,635,028 B2 | 1/2014 | Sengupta et al. |
| 8,647,835 B2 | 2/2014 | Walsh et al. |
| 8,652,800 B2 | 2/2014 | Walsh et al. |
| 8,703,061 B2 | 4/2014 | Guzman |
| 8,709,344 B2 | 4/2014 | Bishop et al. |
| 8,765,062 B2 | 7/2014 | Linder et al. |
| 8,779,779 B2 | 7/2014 | Wang et al. |

(56) References Cited

U.S. PATENT DOCUMENTS

| | | |
|---|---|---|
| 8,780,181 B2 | 7/2014 | Olesen et al. |
| 8,804,105 B2 | 8/2014 | Ayliffe |
| 8,821,814 B2 | 9/2014 | Cho et al. |
| 8,828,680 B2 | 9/2014 | Williams et al. |
| 8,841,118 B2 | 9/2014 | Robinson et al. |
| 8,895,255 B1 | 11/2014 | Goldberg et al. |
| 8,911,987 B2 | 12/2014 | Robinson et al. |
| 8,932,523 B2 | 1/2015 | Linder et al. |
| 8,943,588 B1 | 1/2015 | Speegle et al. |
| 8,969,072 B2 | 3/2015 | Robinson et al. |
| 8,970,826 B2 | 3/2015 | Liu et al. |
| 9,007,233 B2 | 4/2015 | Sugiura |
| 9,048,771 B2 | 6/2015 | Ohba et al. |
| 9,057,714 B2 | 6/2015 | Gomm et al. |
| 9,090,462 B2 | 7/2015 | Straus |
| 9,133,498 B2 | 9/2015 | Kwon et al. |
| 9,150,900 B2 | 10/2015 | Bishop et al. |
| 9,213,043 B2 | 12/2015 | Cook et al. |
| 9,248,422 B2 | 2/2016 | Ching et al. |
| 9,274,132 B2 | 3/2016 | Wilson et al. |
| 9,290,382 B2 | 3/2016 | Straus |
| 9,353,396 B2 | 5/2016 | Demirev et al. |
| 9,405,288 B2 | 8/2016 | Ogata |
| 9,434,937 B2 * | 9/2016 | Metzger ............... C12M 47/12 |
| 9,567,621 B2 | 2/2017 | Robinson et al. |
| 9,657,327 B2 | 5/2017 | Metzger et al. |
| 9,677,109 B2 | 6/2017 | Shamsheyeva et al. |
| 9,714,420 B2 | 7/2017 | Metzger et al. |
| 9,841,422 B2 | 12/2017 | Goldberg et al. |
| 2001/0009774 A1 | 7/2001 | Shin et al. |
| 2001/0053535 A1 | 12/2001 | Bashir et al. |
| 2002/0028489 A1 | 3/2002 | Ammann et al. |
| 2002/0028519 A1 | 3/2002 | Yguerabide et al. |
| 2002/0031795 A1 | 3/2002 | James et al. |
| 2002/0119455 A1 | 8/2002 | Chan |
| 2002/0127144 A1 | 9/2002 | Mehta |
| 2002/0148729 A1 | 10/2002 | Armstrong |
| 2002/0155490 A1 | 10/2002 | Skinner et al. |
| 2002/0155591 A1 | 10/2002 | Farina et al. |
| 2002/0164677 A1 | 11/2002 | Giovannoni et al. |
| 2002/0197709 A1 | 12/2002 | Van der Weide et al. |
| 2003/0023149 A1 | 1/2003 | Montemagno et al. |
| 2003/0032171 A1 | 2/2003 | Gemmell et al. |
| 2003/0032173 A1 | 2/2003 | Farina et al. |
| 2003/0036054 A1 | 2/2003 | Ladisch et al. |
| 2003/0119028 A1 | 6/2003 | Graves et al. |
| 2003/0124623 A1 | 7/2003 | Yager et al. |
| 2003/0134269 A1 | 7/2003 | Hirai et al. |
| 2003/0147132 A1 | 8/2003 | Behnsen et al. |
| 2003/0153023 A1 | 8/2003 | Starzl et al. |
| 2003/0157587 A1 | 8/2003 | Gomez et al. |
| 2003/0170613 A1 | 9/2003 | Straus |
| 2003/0186341 A1 | 10/2003 | Kuhn et al. |
| 2003/0211566 A1 | 11/2003 | Gazenko |
| 2003/0224436 A1 | 12/2003 | Nelson et al. |
| 2004/0052426 A1 | 3/2004 | Landesman |
| 2004/0089546 A1 | 5/2004 | Bahatt et al. |
| 2004/0168916 A1 | 9/2004 | Fuchs et al. |
| 2004/0189311 A1 | 9/2004 | Glezer et al. |
| 2005/0048599 A1 | 3/2005 | Goldberg et al. |
| 2005/0059105 A1 | 3/2005 | Alocilja et al. |
| 2005/0112544 A1 | 5/2005 | Xu et al. |
| 2005/0114041 A1 | 5/2005 | Gawad et al. |
| 2005/0118705 A1 | 6/2005 | Rabbitt et al. |
| 2005/0121596 A1 | 6/2005 | Kam et al. |
| 2005/0202523 A1 | 9/2005 | Shaw et al. |
| 2005/0208592 A1 | 9/2005 | Caron et al. |
| 2005/0213374 A1 | 9/2005 | Xu et al. |
| 2005/0221403 A1 | 10/2005 | Gazenko |
| 2005/0238652 A1 | 10/2005 | Tsuji et al. |
| 2005/0255445 A1 | 11/2005 | Van Damme et al. |
| 2005/0287572 A1 | 12/2005 | Mathies et al. |
| 2006/0120916 A1 | 6/2006 | Kolari et al. |
| 2006/0141618 A1 | 6/2006 | Yasuda et al. |
| 2006/0166184 A1 | 7/2006 | Yasuda et al. |
| 2006/0194307 A1 | 8/2006 | Yasuda et al. |
| 2006/0243594 A1 | 11/2006 | Schnelle et al. |
| 2007/0037225 A1 | 2/2007 | Metzger et al. |
| 2007/0202538 A1 | 8/2007 | Glezer et al. |
| 2007/0238146 A1 | 10/2007 | Tyler et al. |
| 2007/0298513 A1 | 12/2007 | Starzl et al. |
| 2008/0014181 A1 | 1/2008 | Ariff et al. |
| 2008/0046286 A1 | 2/2008 | Halsted |
| 2008/0072664 A1 | 3/2008 | Hansen et al. |
| 2008/0138799 A1 | 6/2008 | Cheng et al. |
| 2008/0193965 A1 | 8/2008 | Zeng et al. |
| 2008/0221805 A1 | 9/2008 | Andrews |
| 2008/0241858 A1 | 10/2008 | Metzger et al. |
| 2009/0012723 A1 | 1/2009 | Treado et al. |
| 2009/0051372 A1 | 2/2009 | Sethu et al. |
| 2009/0104689 A1 | 4/2009 | Kim et al. |
| 2009/0203063 A1 | 8/2009 | Wheeler et al. |
| 2009/0208072 A1 | 8/2009 | Seibel et al. |
| 2010/0048428 A1 | 2/2010 | Coyer et al. |
| 2010/0075340 A1 | 3/2010 | Javanmard |
| 2010/0099139 A1 | 4/2010 | Ben-David et al. |
| 2010/0120016 A1 | 5/2010 | Li et al. |
| 2010/0129858 A1 | 5/2010 | Walsh et al. |
| 2010/0248281 A1 | 9/2010 | Straus |
| 2010/0267165 A1 | 10/2010 | Bruls et al. |
| 2011/0023690 A1 | 2/2011 | Wilson |
| 2011/0042582 A1 | 2/2011 | Ingber et al. |
| 2011/0117577 A1 | 5/2011 | Reboud et al. |
| 2011/0136165 A1 | 6/2011 | Vojnovic et al. |
| 2011/0183856 A1 | 7/2011 | Agan et al. |
| 2011/0237446 A1 | 9/2011 | Treado et al. |
| 2011/0242308 A1 | 10/2011 | Igarashi et al. |
| 2011/0256617 A1 | 10/2011 | Cocchi et al. |
| 2012/0028342 A1 | 2/2012 | Ismagilov et al. |
| 2012/0077206 A1 | 3/2012 | Metzger et al. |
| 2012/0103817 A1 | 5/2012 | Omori et al. |
| 2012/0105837 A1 | 5/2012 | Ingber |
| 2012/0142032 A1 | 6/2012 | Morgan |
| 2012/0149584 A1 | 6/2012 | Olle |
| 2012/0169863 A1 | 7/2012 | Bachelet et al. |
| 2012/0223217 A1 | 9/2012 | Zheng et al. |
| 2012/0244519 A1 | 9/2012 | Olesen et al. |
| 2012/0258874 A1 | 10/2012 | Narain et al. |
| 2013/0017534 A1 | 1/2013 | Nickel et al. |
| 2013/0045878 A1 | 2/2013 | McCue |
| 2013/0089886 A1 | 4/2013 | Feng et al. |
| 2013/0115607 A1 | 5/2013 | Nielsen et al. |
| 2013/0183694 A1 | 7/2013 | Janetzko et al. |
| 2013/0217063 A1 | 8/2013 | Metzger et al. |
| 2013/0271060 A1 | 10/2013 | Messersmith et al. |
| 2013/0295588 A1 | 11/2013 | Watkins et al. |
| 2013/0295597 A1 | 11/2013 | DeWitte et al. |
| 2013/0324437 A1 | 12/2013 | Pogliano et al. |
| 2013/0345525 A1 | 12/2013 | Kline |
| 2014/0038171 A1 | 2/2014 | Metzger et al. |
| 2014/0179726 A1 | 6/2014 | Bajaj et al. |
| 2014/0199719 A1 | 7/2014 | Shih et al. |
| 2014/0234949 A1 | 8/2014 | Wasson et al. |
| 2014/0278136 A1 | 9/2014 | Shamsheyeva et al. |
| 2014/0278143 A1 | 9/2014 | Garstecki et al. |
| 2014/0323340 A1 | 10/2014 | Goldberg et al. |
| 2014/0343868 A1 | 11/2014 | Colwell et al. |
| 2015/0168290 A1 | 6/2015 | Shachaf |
| 2015/0225762 A1 | 8/2015 | Metzger et al. |
| 2015/0293270 A1 | 10/2015 | Jarvius et al. |
| 2015/0301002 A1 | 10/2015 | DeWitte et al. |
| 2015/0337351 A1 | 11/2015 | Metzger |
| 2016/0010138 A1 | 1/2016 | Shamsheyeva et al. |
| 2016/0051985 A1 | 2/2016 | Knight et al. |
| 2016/0238826 A1 | 8/2016 | Shields et al. |
| 2016/0279633 A1 | 9/2016 | Bachelet et al. |
| 2016/0289729 A1 | 10/2016 | Richards et al. |
| 2016/0348091 A1 | 12/2016 | Metzger et al. |
| 2017/0023599 A1 | 1/2017 | Richards et al. |

(56) References Cited

U.S. PATENT DOCUMENTS

| | | |
|---|---|---|
| 2017/0029864 A1 | 2/2017 | Straus |
| 2017/0218426 A1 | 8/2017 | Shamsheyeva et al. |
| 2018/0080932 A1 | 3/2018 | Goldberg et al. |
| 2018/0135093 A1 | 5/2018 | Ashby et al. |

FOREIGN PATENT DOCUMENTS

| | | |
|---|---|---|
| EP | 1648286 | 4/2006 |
| EP | 2 645 108 A1 | 10/2013 |
| EP | 2 987 851 A1 | 2/2016 |
| EP | 2 507 663 B1 | 2/2017 |
| GB | 1520733 | 8/1978 |
| JP | 52102491 | 8/1977 |
| JP | 58198759 | 11/1983 |
| JP | H11505405 | 5/1999 |
| JP | 2001509008 | 7/2001 |
| JP | 2002500892 | 1/2002 |
| JP | 2002502597 | 1/2002 |
| JP | 2002330799 | 11/2002 |
| JP | 2003527601 | 9/2003 |
| JP | 200481019 | 3/2004 |
| JP | 2004513628 | 5/2004 |
| WO | WO 1989001162 | 2/1989 |
| WO | WO 8910566 A1 | 11/1989 |
| WO | WO 1990011525 | 10/1990 |
| WO | WO 1991004491 | 4/1991 |
| WO | WO 1993013197 | 7/1993 |
| WO | WO 1994002831 | 2/1994 |
| WO | WO 1994011728 | 5/1994 |
| WO | WO 1995008640 | 3/1995 |
| WO | WO 1995028641 | 10/1995 |
| WO | WO 1996014431 | 5/1996 |
| WO | WO 1998022618 | 5/1998 |
| WO | WO 1998022808 | 5/1998 |
| WO | WO 1998040741 | 9/1998 |
| WO | WO 1999020789 | 4/1999 |
| WO | WO 1999037799 | 7/1999 |
| WO | WO 1999040174 | 8/1999 |
| WO | WO 1999058948 | 11/1999 |
| WO | WO 2000024941 | 5/2000 |
| WO | WO 2001031332 | 5/2001 |
| WO | WO 2001069230 | 9/2001 |
| WO | WO 2001079529 A1 | 10/2001 |
| WO | WO 2002038724 | 5/2002 |
| WO | WO 2002088299 | 11/2002 |
| WO | WO 2003012525 A1 | 2/2003 |
| WO | WO 2003022999 | 3/2003 |
| WO | WO 2003025208 | 3/2003 |
| WO | WO 2003048736 | 6/2003 |
| WO | WO 2003065009 | 8/2003 |
| WO | WO 2003073100 | 9/2003 |
| WO | WO 2005027714 | 3/2005 |
| WO | WO 2006015374 | 2/2006 |
| WO | WO 2006028601 A2 | 3/2006 |
| WO | WO 2006066216 | 6/2006 |
| WO | WO 2006113930 A2 | 10/2006 |
| WO | WO 2006135904 | 12/2006 |
| WO | WO 2009124068 | 10/2009 |
| WO | WO 2010062350 | 6/2010 |
| WO | WO 2010062352 | 6/2010 |
| WO | WO 2011/035304 A2 | 3/2011 |
| WO | WO 2012122314 | 9/2012 |
| WO | WO 2012162133 | 11/2012 |
| WO | WO 2013072069 A1 | 5/2013 |
| WO | WO 2013/130875 A1 | 9/2013 |
| WO | WO 2013/177277 A1 | 11/2013 |
| WO | WO 2014040088 | 3/2014 |
| WO | WO 2014100456 | 6/2014 |
| WO | WO 2014145899 | 9/2014 |
| WO | WO 2014153194 | 9/2014 |
| WO | WO 2014169921 A1 | 10/2014 |
| WO | WO 2016/037051 A1 | 3/2016 |
| WO | WO 2016207065 A1 | 12/2016 |

OTHER PUBLICATIONS

MS Bello Electrolytic modification of a buffer during a capillary electrophoresis run. Journal of Chromatography A, 1996; 744: 81-91.*

Jiang et al. Human Adenoviruses and Coliphages in Urban Runoff-Impacted Coastal Waters of Southern California. Appl. Environ. Microbiol. 2001; 67(1): 179-184.*

Alban et al. A novel experimental design for comparative two-dimensional gel analysis: Two-dimensional difference gel electrophoresis incorporating a pooled internal standard. Proteomics, 2003; 3: 36-44.*

Kremser, et al. Capillary electrophoresis of biological particles: Viruses, bacteria, and eukaryotic cells. Electrophoresis 2004, 25, 2282-2291.*

Pagola et al., "The structure of malaria pigment β-haematin," *Nature* 404:307-310, 2000.

U.S. Appl. No. 08/820,365, filed Mar. 12, 1997, now U.S. Pat. No. 5,958,704.

U.S. Appl. No. 09/346,039, filed Jul. 6, 1999, now U.S. Pat. No. 6,274,384.

U.S. Appl. No. 10/888,828, filed Jul. 8, 2004, now U.S. Pat. No. 7,687,239.

U.S. Appl. No. 11/303,803, filed Dec. 16, 2005, now U.S. Pat. No. 7,341,841.

U.S. Appl. No. 12/021,087, filed Jan. 28, 2008, now U.S. Pat. No. 8,071,319.

U.S. Appl. No. 12/702,210, filed Feb. 8, 2010, now U.S. Pat. No. 8,460,887.

U.S. Appl. No. 13/311,100, filed Dec. 5, 2011, now abandoned.

U.S. Appl. No. 13/763,446, filed Feb. 8, 2013, now U.S. Pat. No. 8,895,255.

U.S. Appl. No. 13/843,460, filed Mar. 15, 2013.

U.S. Appl. No. 14/004,145, filed Oct. 16, 2013, now U.S. Pat. No. 9,434,937.

U.S. Appl. No. 14/204,222, filed Mar. 11, 2014, now abandoned.

U.S. Appl. No. 14/209,917, filed Mar. 13, 2014.

U.S. Appl. No. 14/329,387, filed Jul. 11, 2014.

U.S. Appl. No. 14/427,172, filed Mar. 10, 2015.

U.S. Appl. No. 14/720,588, filed May 22, 2015.

U.S. Appl. No. 14/772,376, filed Sep. 2, 2015.

U.S. Appl. No. 15/003,604, filed Jan. 21, 2016.

U.S. Appl. No. 15/085,953, filed Mar. 30, 2016.

U.S. Appl. No. 15/236,021, filed Aug. 12, 2016.

U.S. Appl. No. 15/283,922, filed Oct. 3, 2016.

U.S. Appl. No. 15/484,250, filed Apr. 11, 2017.

Palarasah et al., "Sodium Polyanethole Sulfonate as an Inhibitor of Activation of Complement Function in Blood Culture Systems," *J Clin Microbiol*. 48:908-914, 2010.

EP 13835702.5 Office Action dated Oct. 16, 2017 (9 pages).

EP 16200084.8 Extended European Search Report dated Aug. 1, 2017 (17 pages).

EP 16192372.7 Extended European Search Report and Written Opinion dated Feb. 28, 2018 (11 pages).

Olsvik et al., "Magnetic Separation Techniques in Diagnostic Microbiology", *Clin Microbiol Rev*. 7:43-54, 1994.

Bloem et al., "Fully Automatic Determination of Soil Bacterium Numbers, Cell Volumes, and Frequencies of Dividing Cells by Confocal Laser Scanning Microscopy and Image Analysis," *Appl Environ Microbiol*. 61:926-936, 1995.

U.S. Appl. No. 15/827,187, filed Nov. 30, 2017.

U.S. Appl. No. 15/849,297, filed Dec. 20, 2017.

Inoue et al., "On-chip culture system for observation of isolated individual cells," *Lab on a Chip* 1:50-55, 2001.

Rodrigues and Kroll, "Rapid selective enumeration of bacteria in foods using a microcolony epifluorescence microscopy technique," *J Appl Bacteriol*. 64:65-78, 1988.

Zhu et al., "Filter-based microfluidic device as a platform for immunofluorescent assay of microbial cells," *Lab Chip* 4:337-341, 2004.

(56) References Cited

OTHER PUBLICATIONS

Accelerate Diagnostics: "Accelerate ID/AST," Vimeo, May 18, 2015, pp. 1-6, XP054976621, Retrieved from the Internet: URL:https://vimeo.com/128112270 [retrieved on Jun. 22, 2016].
Accelerate Diagnostics: "Fast Phenotypic Antibiotic Susceptibility Testing: Connie Price, M.D.," YouTube, Aug. 28, 2015, pp. 1-6, XP054976622, Retrieved from the Internet: URL:https://www.youtube.com/watch?v=1n1GW54atXE&index=3&list=PLsmqpsknnk2_ENp8Xd3BhK0vu9nfU0p6y [retrieved on Jun. 22, 2016].
Alere, Inc., "Adult Isolator Tube Solution Material Safety Data Sheet," (2010).
Aminian et al., "A Conformal Bayesian Network for Classification of *Mycobacterium tuberculosis* Complex Lineages," BMC Bioinformatics, 11(Suppl 3): S4 (2010).
Anzaldi et al., "Overcoming the Heme Paradox: Heme Toxicity and Tolerance in Bacterial Pathogens," Infect. Immun. 78(12): 4977-4989 (2010).
Ateya et al., "Volume Cytometry: Microfluidic Sensor for High-Throughput Screening in Real Time," Analytical Chem., 77:1290-1294, (2005).
Atlas and Snyder, Handbook of Media for Clinical Microbiology, 2006. CRC press.
Bae et al., "Immunosensor for Detection of Yersinia Enterocolitica Based on Imaging Ellipsometry," Analytical Chem., 76:1799-1803, (2004).
Baker et al., "The Bactericidal Action of Synthetic Detergents," J Exp Med. 74:611 620, 1941.
Balaban et al., "Bacterial Persistence as a Phenotypic Switch," Science, 305, pp. 1622-1625, (2004).
Barton et al., "Measurement of Bacterial Growth Rates on Polymers," J. Biomed. Mater Res., 32, pp. 271-278, (1996).
Bayoudh el al., "Electrical Detection and Characterization of Bacterial Adhesion Using Electrochemical Impedance Spectroscopy-Based Flow Chamber," Colloids and Surfaces A: Physicochem. Eng. Aspects, 318:291-300, (2008).
Beaglehole, "Performance of a Microscopic Imaging Ellipsometer," Rev. Sci. Instrum., 59:12, pp. 2557-2559, (1988).
Belding et al., "Effect of Sodium Polyanetholesulfonate on Antimicrobial Systems in Blood," Appl. Microbiol. 24(5): 691-698 (1972).
Benecky et al., "Simultaneous Detection of Multiple Analytes Using Copalis Technology: A Reduction to Practice," Clin. Chem., 44:9, pp. 2052-2054, (1998).
Boehm et al., "On-Chip Microfluidic Biosensor for Bacterial Detection and Identification," Sensors and Actuators, 126:508-514, (2007).
Bridson, E.Y., and Gould, G.W., "Quantal Microbiology," Lett. Appl. Microbiology, 30:95-98, (2000).
Burnham C-1358: Poster—"Rapid Detection of *Klebsiella pneumoniae* Carbapenemase (KPC) Producing Isolates Using the BACcel™ Digital Microscopy System," Presented at ASM 2013 May 18, 2013, Denver, CO.
Burnham et al., "Rapid Ertapenem Susceptibility Testing and *Klebsiella pneumoniae* Carbapenemase (KPC) Phenotype Detection in *Klebsiella pneumoniae* Using Automated Microscopy of Immobilized Live Bacterial Cells," *J Clin Microbiol*. 52:982-986, 2014.
Cabrera et al., "Continuous Concentration of Bacteria in a Microfluidic Flow Cell Using Electrokinetic Techniques," *Electrophoresis* 22:355-362, 2001.
Chan et al., "Evaluation of Lysis Filtration as an Adjunct to Conventional Blood Culture," J. Clin. Pathol. 39: 89-92 (1986).
Cheung et al., "Microfluidic Impedance-Based Flow Cytometry," Cytometry A, 77A, pp. 648-666, (2010).
Choi et al., "Rapid antibiotic susceptibility testing by tracking single cell growth in a microfluidic agarose channel system," *Lab Chip* 13:280-287, 2013.
Cooper et al. D-4013: Poster—"Potential Impact of Rapid Phenotype Identification on Antimicrobial Prescribing," Presented at the 48th ICAAC and IDSA Oct. 28, 2008, Washington, DC.

Dai et al., "Electrokinetic Trapping and Concentration Enrichment of DNA in a Microfluidic Channel," J. Am. Chem. Soc., 125"13026-13027, (2003).
Daims et al., "Quantification of Uncultured Microorganisms by Fluorescence Microscopy and Digital Image Analysis," Appl. Microbiol. Biotechnol., 75"237-248, (2007).
De Brabander et al.. "Detection of Gold Probes With Video-Enhanced Contrast Microscopy: Nanovid Microscopy," Amer. J., Anat. 185:282-295, (1989).
Delehanty, J.B., and Ligler, F.S., "A Microarray Immunoassay for Simultaneous Detection of Proteins and Bacteria," Anal. Chem., 74:5681-5687, (2002).
Desai, M.J., and Armstrong, D.W., "Separation, Identification, and Characterization of Microorganisms by Capillary Electrophoresis," Microbiology and Molecular Biology Reviews, 67, pp. 38-51, (2003).
Dorn et al., "Blood Culture Technique Based on Centrifugation: Developmental Phase," J. Clin. Micro. 3(3): 251-257 (1976).
Douglas et al. Poster—"Rapid Microbiological Identification and Major Drug Resistance Phenotyping with Novel Multiplexed Automated Digital Microscopy (MADM) for Ventilator-Associated Pneumonia (VAP) Surveillance," Presented at ATS 2011 May 16, 2011, Denver, CO.
Douglas et al., Rapid Automated Microscopy for Microbiological Surveillance of Ventilator-associated Pneumonia, *Am J Respir Crit Care Med*. 191:566-573, 2015.
Dwek et al., "Synchronization of Cell Division in Microorganisms by Percoll Gradients," J. Bacteriol. 144(1):17-21 (1980).
Elfwing et al., "Observing Growth and Division of Large Numbers of Individual Bacteria by Image Analysis," Appl. Environ. Micro., 70, pp. 675-678, (2004).
Elghanian et al., "Selective Colorimetric Detection of Polynucleotides Based on the Distance-Dependent Optical Properties of Gold Nanoparticles," Science, 277, pp. 1078-1081, (1997).
Ertl et al., "Electrochemical Biosensor Array for the Identification of Microorganisms Based on Lectin-Lipopolysaccharide Recognition," Analytical Chem., 73: 4241-4248, (2001).
Ertl et al., "Rapid Identification of Viable *Escherichia coli* Subspecies with Electrochemical Screen-Printed Biosensor Array," Biosensors Bioelectronics, 18, pp. 907-916, (2003).
Fun et al., "Encapsulating Bacteria in Agarose Microparticles Using Microfluidics for High-Throughput Cell Analysis and Isolation," ACS Chem. Biol., 18:260-266, (2011).
Fesenko et al., "Biosensing and Monitoring of Cell Populations Using the Hydrogel Bacterial Microchip," Biosens Bioelectron. 20:1860-1865, 2005.
Forero et al., "Automatic Identification Techniques of Tuberculosis Bacteria," Proc. SPIE 5203, Applications of Digital Image Processing XXVI, (Tescher, A.G., Ed.) SPIE Proceedings, 5203:71-81, (2003).
Friedman et al., "Precise Temporal Modulation in the Response of the SOS DNA Repair Network in Individual Bacteria," PLoS Bio. 3:1261-1268, (2005).
Gadkari, "Optimal Hydrogels for East and Safe Delivery of Bioactive Compounds," A Thesis Submitted to the Faculty of Drexel University, (2007).
Gamage et al. 2556: Poster—"Rapid Detection of Clinically Important *Staphylococcus aureus* Resistance Phenotypes Directly from Positive Blood Cultures Using Automated Microscopy," Presented at ASM2014 May 20, 2014, Boston, MA.
Gao et al., "Epipolarization Microscopic lmmunogold Assay: A Combination of lmmunogold Silver Staining, ELISA and Epipolarization Microscopy," Biotech. & Histochem., 70:211-216, (1995).
Gast, R.K. et al., "Detection of *Salmonella entertidis* in Incubated Pools of Egg Contents by Fluorescence Polarization and Lateral Flow Immunodiffusion," Poultry Science, 82:687-690, (2003).
Gawad et al., "Micromachined Impedance Spectroscopy Flow Cytometer for Cell Analysis and Particle Sizing," Lab on a Chip, 1, pp. 76-82, (2001).
Geerts et al., "Nanovid Microscopy," Nature, 1991, 351:765-766, (1991).

(56) References Cited

OTHER PUBLICATIONS

Geesey, and White, "Determination of Bacterial Growth and Activity at Solid-Liquid Interfaces," Annu. Rev. Microbiol., 44:579-602, (1990).

Gomez et al., "Microfluidic Biochip for Impedance Spectroscopy of Biological Species," Biomedical Microdevices, 3:3, pp. 201-209, (2001).

Greef et al., "Identification and Growth Rate Quantitation of Individual Bacterial Clones Using a Novel Microfluidic Concentration Device," Accelr8 Technology Corporation (1 page), 2006.

Hach Company, "Heterotrophic Bacteria, Pour Plate Method," Edition 7 (10 pages), 2012.

Hance et al. C-065: Poster—"A Rapid indirect Enzyme-Linked Immunosorbent Assay for Identification of *Acinetobacter* spp. from Cultured Isolates," Presented at the American Society for Microbiology 108th General Meeting Jun. 2, 2008.

Hance et al. K-392: Poster—"Rapid Identification of Live *Acinetobacter* spp. in Bronchoalveolar Lavage Specimens by Automated Immunofluorescence Microscopy," Presented at the 47th ICAAC Sep. 27, 2007.

Hance et al. P0539: Poster—"Pathogen Identification from Positive Blood Cultures Using Automated Sample Preparation and Automated Fluorescent in situ Hybridization (FISH)," Presented at ECCMID 2014, May 11, 2014, Barcelona, Spain.

Hance et al. Poster 2032: Poster—"Rapid Bacterial Identification Directly from Positive Blood Cultures Using Automated Sample Preparation and Multiplexed Fluorescence in situ Hybridization (FISH)," ASM2014, Boston, MA May 20, 2014.

Heileman et al., "Dielectric Spectroscopy as a Viable Biosensing Tool for Cell and Tissue Characterization and Analysis," Biosensors and Bioelectronics, 49, pp. 348-359, (2013).

Huang et al., "Electric Manipulation of Bioparticles and Macromolecules on Microfabricated Electrodes," Analytical Chem., 73, pp. 1549-1559, (2001).

Huang et al., "Lysozyme for Capture of Microorganisms on Protein Biochips," Enzyme and Microbial. Technol., 33:958-966, (2003).

Inverness Medical Group, "Wampole Isostat Microbial Tubes, Instructions for Use and Supplementary Application Notes," (2008).

Iregui et al., "Clinical Importance of Delays in the Initiation of Appropriate Antibiotic Treatment for Ventilator-Associated Pneumonia," *Chest* 122:262-268, 2002.

Isse et al., "Digital Transplantation Pathology: Combining Whole Slide Imaging, Multiplex Staining and Automated image Analysis," *Am J Transplant*. 12:27-37, 2012.

Jampachaisri et al., "Classification of oligonucleotide fingerprints: application for microbial community and gene expression analyses," Bioinformatics 21: 3122-3130 (2005).

Ji et al., "Real-time Detection of Bacterial Contamination in Dynamic Aqueous Environments Using Optical Sensors," Analytical Chem., 76:1411-1418, (2004).

Jin et al., "A Biosensor Concept Based on Imaging Ellipsometry for Visualization of Biomolecular Interactions," Analytical Biochem., 232:69-72, (1995).

Kastenholz, B. "Comparison of the Electrochemical Behavior of the High Molecular Mass Cadmium Proteins in *Arabidopsis thaliana* and in Vegetable Plants on Using Preparative Native Continuous Polyacrylamide Gel Electrophoresis (PNC-PAGE)," Electroanalysis 18:103-106 (2006).

Kim and Soh, "Simultaneous Sorting of Multiple Bacterial Targets Using Integrated Dielectrophoretic-Magnetic Activated Cell Sorter," Lab Chip 9:2313-2318, 2009.

Kim et al., "Programmed Trapping of Individual Bacteria Using Micrometre-Size Sieves," Lab on a Chip, 11, pp. 1089-1095, (2011).

Koh et al., "Integrating Polymerase Chain Reaction, Valving, and Electrophoresis in a Plastic Device for Bacterial Detection," Analytical Chem., 75:4591-4598, (2003).

Kremser, et al., "Capillary Electrophoresis of Biological Particles: Viruses, Bacteria, and Eukaryotic Cells," Electrophoresis 25: 2282-2291 (2004).

Kubitschko et al., "Sensitivity Enhancement of Optical Immunosensors with Nanoparticles," Analytical Biochem., 253, pp. 112-122, (1997).

Kuehn et al., "Automated Confocal Laser Scanning Microscopy and Semiautomated Image Processing for Analysis of Biofilms," Appl. Environ. Microbio., 64:4115-4127, (1998).

Kumar et al., "Duration of Hypotension Before Initiation of Effective Antimicrobial Therapy is the Critical Determinant of Survival in Human Septic Shock," *Crit Care Med*. 34:1589-1596, 2006.

Lagally et al., "Integrated Portable Genetic Analysis Microsystem for Pathogen/Infectious Disease Detection," Analytical Chem., 76, pp. 3162-3170, (2004).

Lawrence et al., "Computer-Enhanced Darkfield Microscopy for the Quantitative Analysis of Bacterial Growth and Behavior on Surfaces," J. Microbial. Methods 10:123-138, (1989).

Lerner, "Bayesian Fluorescence In Situ Hybridisation Signal Classification," Artif. Intell. Med. 30: 301-316 (2004).

Levin-Reisman et al., "Automated Imagining With ScanLag Reveals Previously Undetectable Bacterial Growth Phenotypes," *Nature Methods* 7:737-739, 2010.

Lisby et al. ePoster "Performance of the new Accelerate ID/AST System in Highly Resistant *Acinetobacter baumannii* Bloodstream Infection Isolates, Compared to Routine Laboratory Testing," ECCMID Apr. 23, 2015, Copenhagen, Denmark.

Liu et al., "CMEIAS: A Computer-Aided System for the Image Analysis of Bacterial Morphotypes in Microbial Communities," Microb. Ecol., 41:173-194, (2001).

Lloyd, D., and Hayes, A.J., "Vigour, Vitality and Viability of Microorganisms," FEMS Microbio. Lett., 133:1-7, (1995).

Lochhead, "Microfluidic Devices that Capture Bacteria for Growth and Kill Analysis," Nov. 14, 2006, XP055207195, retrieved from the Internet: URL:http://acceleratediagnostics.com/docs/AVS_2006_Capture.pdf [retrieved on Aug. 11, 2015].

Luna et al., "Appropriateness and Delay to initiate Therapy in Ventilator-Associated Pneumonia," *Eur Respir J*. 27:158-164, 2006.

Maeyama et al., "Confocal Imaging of Biofilm Formation Process Using Fluoroprobed *Escherichia coli* and Fluorostained Exopolysaccharide," J. Biomed. Mater Res., 70:274-282, (2004).

Magnusdottir, et al. "Collection of Capillary Electrophoresis Fractions on a Moving Membrane," From Methods in Molecular Biology, vol. 162: Capillary Electrophoresis of Nucleic Acids, vol. 1: Introduction to the Capillary Electrophoresis of Nucleic Acids. 22: 323-331 (2001).

Markx, G. H. et al., "Dielectrophoretic Separation of Cells: Continuous Separation," Biotechnol. Bioeng., 45:337-343, (1995).

Markx, G.H. et al., "Dielectrophoretic Characterization and Separation of Micro-Organisms" Microbiology, 140:585-591 (1994).

Meinders et al., "In Situ Enumeration of Bacterial Adhesion in a Parallel Plate Flow Chamber—Elimination or in Focus Flowing Bacteria From the Analysis," J. Microbiol. Methods, 16:119-124, (1992).

Metzger et al. C-163: Poster—"Direct Observation of Inducible Clindamycin Resistance in *Staphylococcus aureus* Using Single Live Cell Imaging," Presented at the American Society for Microbiology General Meeting May 23, 2006.

Metzger C-032: Poster—"Direct Identification of Methicillin Resistant *Staphylococcus aureus* (MRSA) Using Small Numbers of Immobilized Cells and Response to Oxacillin (OCA) by Automated Growth Analysis," Presented at the American Society for Microbiology 107th General Meeting, May 22, 2007.

Metzger et al. D-892: Poster—"Identification of mecA in *Staphylococcus aureus* Using Small Numbers of Immobilized Cells and the Response to Cefoxitin (FOX) by Automated Growth Analysis," Presented at the 47th ICAAC Sep. 28, 2007.

Metzger et al. C-005: Poster—"Direct Identification of MRSA and $MLS_B$ Phenotypes in *Staphylococcus aureus* Using Small Numbers of Immobilized Cells," Presented at the American Society for Microbiology 108th General Meeting Jun. 2, 2008.

Metzger et al. C-145: Poster—"Direct Detection and Enumeration of Viable Bacteria in Human Bronchoalveolar Lavage Specimens Using Automated Growth Rate Analysis," Presented at the American Society for Microbiology 108th General Meeting Jun. 2, 2008.

(56) References Cited

OTHER PUBLICATIONS

Metzger et al. D-282: Poster—"Direct Identification of the ESBL Phenotype in *Enterobacteriaceae* Isolates Using Small Numbers of Immobilized Cells," Presented at the 48th ICAAC and IDSA Oct. 25, 2008, Washington, DC.
Metzger et al. C-207: Poster—"Rapid Identification of Resistance Phenotypes in Gram-Negative Bacilli Using Automated Digital Microscopy," Presented at the 109th General Meeting of the ASM, Philadelphia, PA, May 23, 2009.
Metzger et al. C-1140: Poster—"Rapid Quantitation and Identification of *Pseudomonas aeruginosa, Staphylococcus aureus*, and *Acinetobacter baumannii* In Bronchoalveolar Lavage Fluid," Presented at the 110th General Meeting of the ASM May 24, 2010, San Diego, CA.
Metzger et al. Poster: "Same-Day ID and Resistance Phenotyping Directly from Respiratory Specimens by Automated Microscopy," Presented at ASM 2011, New Orleans, May 22, 2011.
Metzger et al. Poster—"Automated 4-Hour Detection of Heteroresistant Vancomycin-Intermediate *Staphylococcus aureus* (hVISA)," Presented at ASM 2011 May 22, 2011, New Orleans.
Metzger et al. D-791: Poster—"Direct-From-Remnant-Specimen Quantitative Identification Using Automated Microscopy," Presented at the 50th ICAAC, Sep. 13, 2010, Boston, MA.
Metzger and Dunne D-102: Poster—"Same-Shift ID Directly from Respiratory Specimens by Automated Microscopy," Presented at 51st ICAAC Sep. 17, 2011, Chicago, IL.
Metzger et al. C-157: Poster—"3-Hour ESBL Detection from Positive Blood Cultures Using Multiplexed Automated Digital Microscopy (MADM)," Presented at ASM 2012 Jun. 17, 2012, San Francisco, CA.
Metzger et al. C-751: Poster—"Rapid and Automated Specimen Preparation for Clinical Microbiology," Presented at ASM 2012 Jun. 17, 2012, San Francisco, CA.
Metzger D-1410: Poster—"Same-Day Blood Culture with Digital Microscopy," Presented at ICAAC 2012 Sep. 11, 2012, San Francisco, CA.
Metzger et al., "Rapid Simultaneous Identification and Quantitation of *Staphylococcus aureus* and *Pseudomonas aeruginosa* Directly from Bronchoalveolar Lavage Specimens Using Automated Microscopy," *Diagn Microbiol Infect Dis*. 79:160-165, 2014.
Miller et al., "SOS Response Induction by Beta-Lactams and Bacterial Defense Against Antibiotic Lethality," Science, 305:1629-1631, 2004.
Mishra et al., "On-Chip Micro-Biosensor for the Detection of Human CD4+ Cells Based on AC Impedance and Optical Analysis," Biosensors and Bioelectronics, 21:696-704, (2005).
Moffitt et al., "The Single-Cell Chemostat: An Agarose-Based, Microfluidic Device for High-Throughput, Single-Cell Studies of Bacteria and Bacterial Communities," Lab Chip 12:1487-1494, 2012.
Mohamad et al., "Bacteria Identification from Microscopic Morphology Using Naïve Bayes," IJCSEIT 4:1-9, 2014.
Molin et al., "Rapid Detection of Bacterial Growth in Blood Cultures by Bioluminescent Assay of Bacterial ATP," J. Clin. Microbiol. 18:521-525 (1983).
Mueller et al., "Issues in Pharmacokinetics and Pharmacodynamics of Anti-Infective Agents: Kill Curves Versus MIC," Antimicrob. Agents Chemother., 48:369-377, (2004).
Oheim, "High-Throughput Microscopy Must Re-Invent the Microscope Rather Than Speed up its Functions," Br. J. Pharmacol., 152:1-4, (2007).
Okano et al., "Using Microparticle Labeling and Counting for Attomole-Level Detection in Heterogeneous Immunoassay," Analytical Biochem., 202:120-125, (1992).
Orjih, "Heme Polymerase Activity and the Stage Specificity of Antimalarial Action of Chloroquine," J. Pharm. Exp. Ther. 282(1): 108-112 (1997).
Ozkan et al., "Electro-Optical Platform for the Manipulation of Live Cells," Langmuir, 19:1532-1538, (2003).

Plowman, "Planar Integrated Optical Methods for Examining Thin Films and Their Surface Adlayers," Biomaterials, 19:341-355, (1998).
Price et al. ePoster "Rapid Identification and Antimicrobial Susceptibility Testing of Bacteria in Bloodstream Infections Using the Accelerate ID/AST Technology," ECCMID Apr. 23, 2015, Copenhagen, Denmark.
Price et al., "Rapid antibiotic Susceptibility Phenotypic Characterization of *Staphylococcus aureus* Using Automated Microscopy of Small Numbers of Cells," *J Microbiol Methods*. 98:50-58, 2014.
Probst et al.,"Polydimethylsiloxane Sub-Micron Traps for Single-Cell Analysis of Bacteria," Micromachines, 4:357-369, (2013).
Rabinovitch et al., "Removal and Inactivation of *Staphylococcus epidermidis* Biofilms by Electrolysis," Applied and Environmental Microbiology, 72:6364-6366, (2006).
Rajagopal et al., "Eight Gram-Negative Bacteria are 10,000 Times More Sensitive to Cationic Detergents than to Anionic Detergents," *Can J Microbiol*. 49:775-779, 2003.
RMM Product Matrix, http://rapidmicromethods.com/files/matrix. php, accessed Jul. 27, 2016. (13 pages).
Rohner et al., "Advantage of Combining Resin with Lytic BACTEC Blood Culture Media," J. Clin. Micro. 35(10): 2634-2638 (1997).
Rohner et al., "Evaluation of the New Improved BHI-Lysis Blood Culture Medium for the BCB Roche System," Eur. J. Clin. Micro. Infect. Dis. 10: 620-624, 1991.
Rösch el al., "Chemotaxonomic Identification of Single Bacteria by Micro-Raman Spectroscopy: Application to Clean-Room-Relevant Biological Contaminations," Applied and Environmental Microbiology, 71: 1626-1637, (2005).
Rose et al., "Using the Membrane Filter in Clinical Microbiology," Med. Lab. 3: 22-23, 29, 43, 1969. Note: The numbered pages omitted from this article are advertisements.
Rowe et al., "Array Biosensor for Simultaneous Identification of Bacterial, Viral, and Protein Analytes," Analytical Chem., 71:3846-3652, (1999).
Salmon et al., "Video-Enhanced Differential Interference Contrast Light Microscopy," BioTechniques, 7:624-633, (1989).
Sapsford et al., "Detection of Campylobacter and Shigella Species in Food Samples Using an Array Biosensor," Analytical Chem., 76:433-440, (2004).
Schrot et al., "Method for Radiorespirometric Detection of Bacteria in Pure Cultures and in Blood," Appl. Micro. 26(2): 867-873 (1973).
Shamsheyeva et al. 2538: Poster—"Rapid Antimicrobial Susceptibility Testing of Non-Fermenting Gram-Negative Bacilli Directly from Positive Blood Cultures by Automated Microscopy," Presented at ASM2014, May 20, 2014, Boston, MA.
Shamsheyeva et al. 2555: Poster—"Evaluation of an Antimicrobial Susceptibility Testing Algorithm to Determine Minimum Inhibitory Concentration Using Growth of Immobilized Staphylococcal Cells Measured by Automated Microscopy," Presented at ASM2014, May 20, 2014. Boston, MA.
Shamsheyeva et al. D-873: Poster "Evaluation of an Antimicrobial Susceptibility Testing Algorithm for Gram-Positive Bacteria Directly from Positive Blood Culture Using Automated Microscopy Analysis of Susceptibility Patterns," Presented at ICAAC Sep. 7, 2014, Washington, DC.
Shamsheyeva et al. P0332: Poster—"Next Generation Automated Phenotypic Antibiotic Susceptibility Testing Utilizing Automated Microscopy Analysis of Bacterial Cells," Presented at ECCMID 2014 May 10, 2014, Barcelona, Spain.
Shamsheyeva et al. P0335: Poster—"5-Hour Antibiotic Susceptibility Testing of Enterococcus faecium and E. faecalis, and Acinetobacter baumannii Directly from Positive Blood Cultures Using Automated Microscopy," Presented at ECCMID 2014 May 10, 2014, Barcelona, Spain.
Sippy et al., "Rapid Electrochemical Detection and Identification of Catalase Positive Micro-Organisms", Biosensors & Bioelectronics, 18:741-749, (2003).
Stewart et al., "Aging and Death in an Organism that Reproduces by Morphologically Symmetric Division," PLoS Biology, 3:295-300 (2005).
Stimpson et al., "Real-Time Detection of DNA Hybridization and Melting on Oligonucleotide Arrays by Using Optical Wave Guides," Genetics, Proc. Natl. Acad. Sci. USA, 92:6379-6383, (1995).

(56) References Cited

OTHER PUBLICATIONS

Stuart, "The Value of Liquid for Blood Culture," J. Clin. Path. 1: 311-314 (1948).
Sun et al., "Single-Cell Microfluidic Impedance Cytometry: A Review," Microfluidics and Nanofluidics, 8: 423-443, (2010).
Suo et al., "Ummunoimmobilization of Living *Salmonella* for Fundamental Studies and Biosensor Applications," in *Salmonella*—A Diversified Superbug, Chapter 25, pp. 497-522, (2012).
Taton et al., "Two-Color Labeling of Oligonucleotide Arrays via Size-Selective Scattering of Nanoparticle Probes," J. Am. Chem. Soc., 123:5164-5165, (2001).
Tison, D.L., "Culture Confirmation of *Escherichia coli* Serotype 0157:H7 by Direct Immunofluorescence," J. Clin. Microbio., 28, 612-613, (1990).
Tokuda et al., "Optical and Electric Multifunctional CMOS Image Sensors for On-Chip Biosensing Applications," *Materials* 4:84-102, 2011.
Tsang et al., "Characterization of Murine Monoclonal Antibodies Against Serogroup B *Salmonellae* and Application as Serotyping Reagents," J Clin Micro. 29:1899-1903, 1991.
Unknown, "Bacterial Counts—Quantitative Analysis of Microbes," Biology 251 General Microbiology Lab, Jul. 30, 2013, pp. 1-5, retrieved from internet: URL:http://biolabs.tmcc.edu/Micro%20Web/BacterialCounts.pdf [retrieved on Oct. 21, 2016].
van der Borden et al., Electric Current-Induced Detachment of *Staphylococcus epidermidis* Biofilms from Surgical Stainless Steel, Appl. Environ. Microbiol., 70:6871-6874, (2004).
van Soestbergen and Lee, "Pour Plates or Steak Plates?," Appl Microbiol. 18:1092-1093, 1969.
Varshney et al., "A Label-Free, Microfluidics and Interdigitated Array Microelectrode-Based Impedance Biosensor in Combination with Nanoparticles Immunoseparation for Detection of *Escherichia coli* O157:H7 in Food Samples," Sensors and Actuators, 128:99-107, (2007).
Vega, et al., "Effect of Ionic Strength and Porosity on Ion Diffusion in Agarose Gels," Summer Bioengineering Conference, Sonesta Beach Resort in Key Biscayne, Florida, 1-2 (2003).
Vener et al., "A Novel Approach to Nonradioactive Hybridization Assay of Nucleic Acids Using Stained Latex Particles," Analytical Biochem., 198, pp. 308-311, (1991).
Von Haebler et al., "The Action of Sodium Polyanethol Sulphonate ("Liquoid") on Blood Cultures," J. Pathol. Bacteriol. 46(2): 245-252 (1938).
Wallace et al. D-918: Poster—"Rapid identification of Gram-negative Bacteria in Positive Blood Culture Broth Using a Multiplex Fluorescence in situ Hybridization (FISH) Assay and Automated Microscopy," Presented at ICAAC Sep. 7, 2014, Washington, DC.
Weeratna et al., "Gene Expression Profiling: From Microarrays to Medicine", J. Clin. Immunol, 24: 213-224, (2004).
Willaert, "Cell Immobilization and its Applications in Biotechnology: Current Trends and Future Prospects," in Fermentation Microbiology and Biotechnology, Chapter 12, p. 313-368, 2006.
Wit, P., and Busscher, H.J., "Application of an Artificial Neural Network in the Enumeration of Yeasts and Bacteria Adhering to Solid Substrata," J. Microbio. Methods, 32, pp. 281-290, (1998).
Wu, et al., "Microfluidic Continuous Particle / Cell Separation via Electroosmotic-Flow-Tuned Hydrodynamic Spreading," J. Micromech. Microeng., 17, pp. 1992-1999, (2007).
Yang, et al., "Electrical/ Electrochemical Impedance for Rapid Detection of Foodborne Pathogenic Bacteria," Biotechnology Advances, 26, pp. 135-150, (2008).
Yeung et al.,"Bayesian Model Averaging: Development of an Improved Multi-Class, Gene Selection and Classification Tool for Microarray Data," Bioinformatics 21: 2394-2402 (2005).
Zhou, et al., "Automated Image Analysis for Quantitative Fluorescence In Situ Hybridization with Environmental Samples," App. Environ. Microbio. 73(9):2956-2962 (2007).
Zierdt et al., "Development of a Lysis-Filtration Blood Culture Technique," J. Clin. Micro. 5(1): 46-50 (1977).
Zierdt et al., "Lysis-Filtration Blood Culture Versus Conventional Blood Culture in a Bacteremic Rabbit Model," J Clin Microbiol. 15:74-77, 1982.
Zierdt, "Blood-Lysing Solution Nontoxic to Pathogenic Bacteria," J. Clin. Micro., 15(1): 172-174 (1982).
Zierdt, "Simplified Lysed-Blood Culture Technique," J. Clin. Micro. 23(3): 452-455 (1986).
CA 2,532,414 Office Action dated Jan. 27, 2014.
CA 2,532,414 Office Action dated Mar. 26, 2015.
EP 03716230.2, European Search Report dated Oct. 15, 2007.
EP 04809482.5, European Office Action dated Jul. 10, 2014.
EP 04809482.5, European Office Action dated Jun. 17, 2010.
EP 04809482.5, European Office Action dated Mar. 13, 2008.
EP 04809482.5, Supplementary European Search Report dated Oct. 19, 2007.
EP 05854636.7, European Office Action dated Mar. 3, 2014.
EP 05854636.7, European Search Report dated Feb. 13, 2013.
EP 12754797.4, Intention to Grant dated May 21, 2015.
EP 12754797.4, Supplementary European Search Report dated Sep. 24, 2014.
EP 13835702.5, European Partial Supplementary Search Report dated Feb. 25, 2016 (8 pages).
EP 13835702.5, European Supplementary Search Report dated Jun. 24, 2016 (12 pages).
EP 13835702.5, Rules 70(2) and 70a(2) EPC Communication dated Jul. 12, 2016 (1 page).
EP 14762411.8 Extended European Search Report dated Nov. 7, 2016 (11 pages).
EP 14762411.8 Partial Supplementary European Search Report dated Jul. 29, 2016 (10 pages).
EP 98911454, European Search Report dated Aug. 5, 2004.
EP16200084.8 Partial European Search Report dated Mar. 1, 2017.
PCT/US1998/04086, International. Preliminary Examination Report dated Jun. 11, 1999.
PCT/US1998/04086, International Search Report dated Jul. 14, 1998.
PCT/US1999/010917, International Search Report dated Jul. 30, 2001.
PCT/US2003/006086, International Search Report dated Jun. 27, 2003.
PCT/US2004/022025, International Preliminary Report on Patentability dated Sep. 26, 2006.
PCT/US2004/022025, International Search Report dated Aug. 7, 2006.
PCT/US2004/022025, Written Opinion dated Aug. 7, 2006.
PCT/US2005/045961, International Preliminary Report on Patentability dated Oct. 30, 2007.
PCT/US2005/045961, International Search Report dated Oct. 15, 2007.
PCT/US2005/045961, Written Opinion dated Oct. 15, 2007.
PCT/US2009/038988, International Preliminary Report on Patentability dated Oct. 5, 2010.
PCT/US2009/038988, International Search Report and Written Opinion dated Jun. 8, 2009.
PCT/US2012/028139, International Preliminary Report on Patentability dated Sep. 19, 2013.
PCT/US2012/028139, International Search Report dated Sep. 28, 2012.
PCT/US2012/028139, Search Report and Written Opinion dated Sep. 28, 2012.
PCT/US2013/059104, International Preliminary Report on Patentability dated Mar. 10, 2015.
PCT/US2013/059104, International Search Report and Written Opinion dated Jan. 10, 2014.
PCT/US2014/030745, International Search Report and Written Opinion dated Aug. 27, 2014.
PCT/US2015/032290; International Search Report and Written Opinion dated Aug. 24, 2015 (13 pages).
PCT/US2016/025075 Invitation to Pay Additional Fees with Partial International Search dated Jul. 6, 2016.

(56) References Cited

OTHER PUBLICATIONS

PCT/US2016/025075, International Search Report and Written Opinion dated Nov. 15, 2016 (36 pages).

* cited by examiner

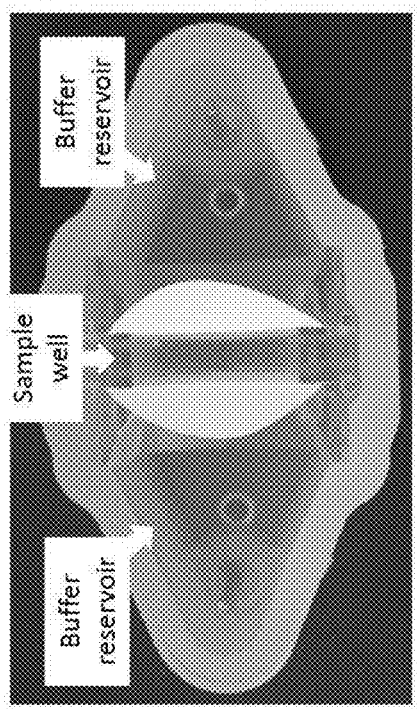
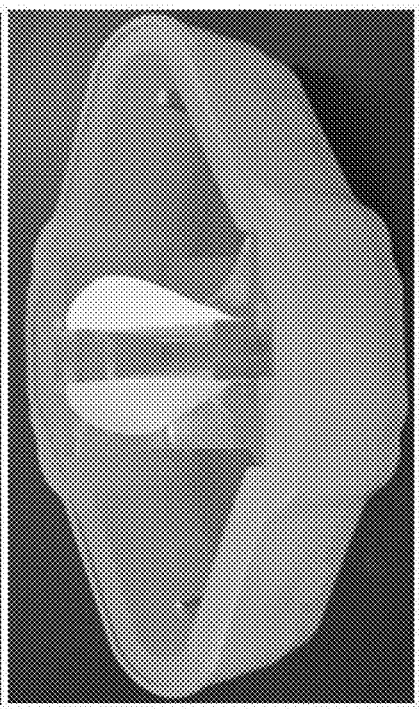
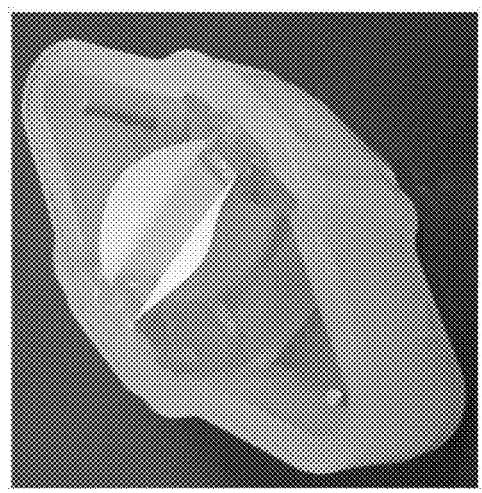
Fig. 10A
Fig. 10B
Fig. 10C

MEMBRANE-ASSISTED PURIFICATION

CROSS REFERENCE TO RELATED APPLICATIONS

This application is a continuation-in-part of U.S. patent application Ser. No. 15/236,021, filed Aug. 12, 2016, which in turn is a continuation of U.S. patent application Ser. No. 14/004,145, filed Oct. 16, 2013, now U.S. Pat. No. 9,434,937 which is a U.S. National Phase filing under 35 U.S.C. § 371 of PCT/US2012/028139, filed Mar. 7, 2012, and claims priority from U.S. Provisional Patent Application No. 61/449,824, filed Mar. 7, 2011, all of which are incorporated herein by reference in their entirety.

FIELD

This disclosure relates to methods and systems for purifying cells and/or viruses, particularly microorganisms in a sample, particularly in preparation for diagnostics systems.

BACKGROUND

Diagnostic systems that detect cells and/or viruses are of clinical and diagnostic interest. Detection of cells and/or viruses is often prevented or complicated by the presence of contaminants that interfere with collection or detection of the cells and/or viruses. This may be particularly true for cells or viruses that are adhered or fixed to a solid surface prior to detection.

Additionally, operator variability may adversely impact the quality of specimen. Specimen quality is dependent on patient factors including but not limited to differences between patients, and the presence or absence of various interfering substances. In many cases, the specimen is split and analyzed using various diagnostic tests. Therefore, purifying samples reliably and cost-effectively to remove inhomogeneities helps to improve the likelihood of relevant statistical sampling of cells and/or viruses therein.

SUMMARY

Methods and systems for purifying one or more microorganisms are provided. In some examples, the method includes adding a biological sample containing contaminants and one or more cells (such as microbial cells), to a well disposed (e.g., present) in a porous filter medium. The porous filter medium contains pores smaller than the one or more cells (such as microbial cells), thereby preventing the one or more cells from entering the porous filter medium. In some examples, the pores are about 200 nm to about 2000 nm in diameter, such as about 200 nm, about 400 nm, about 800 nm or about 2000 nm. The porous filter medium is contacted with a buffer disposed (e.g., present) in one or more reservoirs adjacent to the porous filter medium to initiate diffusion. An electrical potential is applied across the porous filter medium to cause the contaminants to enter the porous filter medium through one or more walls of the well, while retaining the one or more cells (such as microbial cells) in the well. The cells and/or viruses can be removed from the well, and optionally adhered or fixed to a surface, or detected. In one embodiment, the microbial cells and/or viruses are retained in the well by embedding in the medium. The medium including the embedded cells and/or viruses may be excised or otherwise removed and transferred to a glass slide or other solid surface. The medium may then be cut or sectioned to correspond to the respective wells. The medium can then be dried, Gram stained, and the microbial cells/viruses detected.

BRIEF DESCRIPTION OF THE DRAWINGS

FIG. 2I depicts Gram stained microorganisms that may be detected in accordance with the systems and methods described herein.

FIGS. 10A, 10B and 10C provide (A) top and (B, C) side views of an embodiment of a sample well located between filter membranes that separate a sample from fluid reservoirs, each fluid reservoir having an opposing electrode.

DETAILED DESCRIPTION

Described herein are various embodiments of systems and methods for purifying cells (such as microbial cells) and/or viruses in a biological sample. A sample containing cells (such as microbial cells) and/or viruses is added to a well disposed in a medium. A potential is applied across the medium to cause contaminants to enter the medium through one or more walls of said well which retain cells (such as microbial cells) and/or viruses in the well. The cells and/or viruses can then be removed from the well. The cells and/or viruses may also remain in or on the wall of the well, and/or the wall/well may be excised for further analysis.

The systems and methods described herein may concentrate microbial cells and/or viruses from a low content specimen or sample in the wells, thereby removing or reducing potentially interfering debris and resulting in more readable specimens. For example, the disclosed methods and systems may be used in testing of CSF (cerebro-spinal fluid) specimens or other hypocellular specimens. In such samples, bacterial organisms can be localized in 5×5 field of view capture areas (100× objective magnification) to minimize time-consuming searching during microscopic examination. A system having multiple wells may also be used to support parallel processing of sample aliquots for concurrent analyses by multiple downstream methods.

Figure 1:
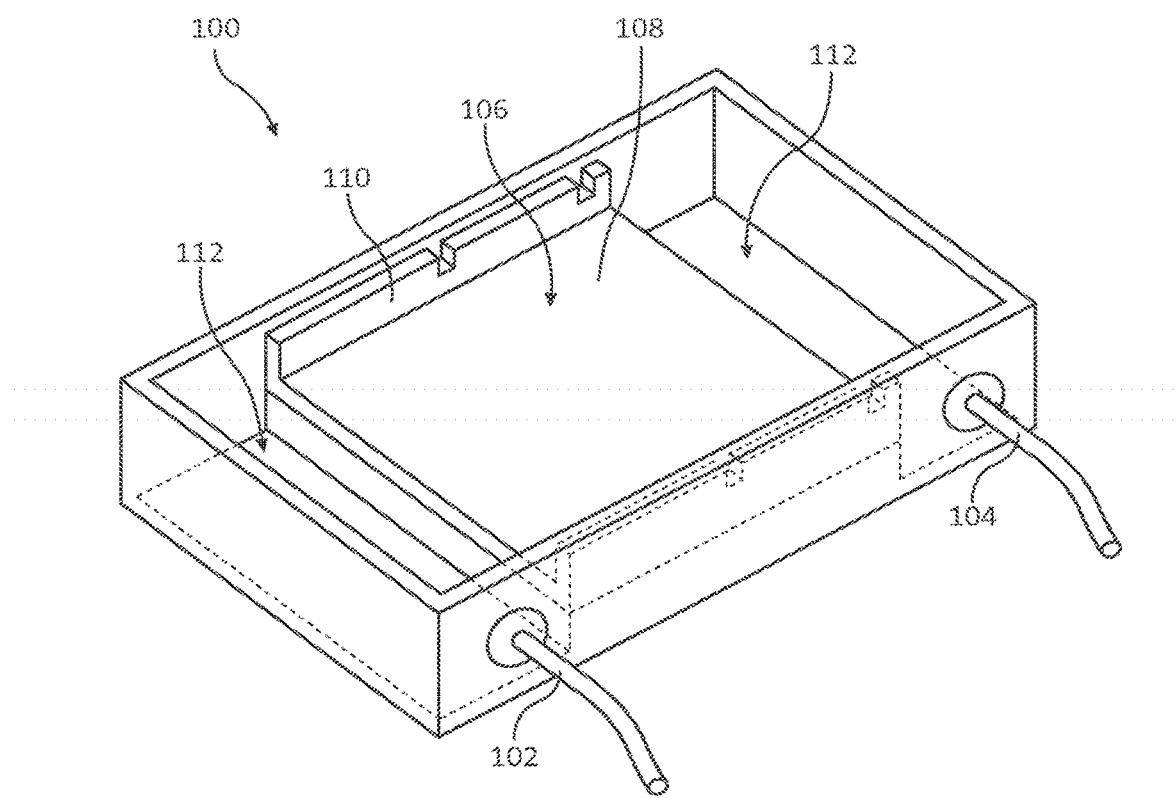
FIG. 1 is a perspective view of an embodiment of a system used to purify a microorganism.

An exemplary embodiment of the system is depicted in FIG. 1. FIG. 1 depicts a system 100 used to purify cells and/or viruses with a cassette 106 configured to receive a medium. The cassette 106 includes a bottom plate 108 and sides 110. Negative electrode 102 and positive electrode 104 are operably connected to the medium through a buffer (not shown) placed in a reservoir 112.

The sample is added to a well disposed in a medium, preferably formed in the medium. In some embodiments, a plastic well may also be disposed in the medium, in addition to well(s) formed in the medium. An electrical potential is applied to the well causing contaminant material to enter the medium while the cells and/or viruses accumulate on the wall of the well. In some embodiments, the cells and/or viruses may be localized on the wall of the well. Cells and/or viruses remain in the well, thereby purifying the sample. The sample may be mixed during or after a time period of the applied electric field. In some embodiments, the process can be repeated until separation of contaminants that interfere with adhesion to a detection surface has been achieved. The well can then be rinsed, and cells and/or viruses recovered. In some embodiments, the wall of the well where the cells and/or viruses have accumulated may be excised or otherwise removed from the rest of the gel medium. Alternatively, the electrical potential can be briefly reversed in polarity to displace the cells and/or viruses from the wall prior to rinsing and recovery. Mixing, applying a potential, and/or reversing polarity of applied field can be performed iteratively to further purify the sample.

In some embodiments, the sample volume recovered is less than, and sometimes substantially less than, the initial sample volume in the wells. In one embodiment, a barrier, such as an impermeable plastic sheet, is inserted into the wells and used to reduce the volume in the wells, thereby further concentrating the cells and/or viruses in the well and providing a reduced sample volume for recovery.

Systems, including electrophoresis boxes and electrodes, can be obtained from Thermo Fisher (Waltham, Mass.) under the EC-Apparatus brand name (e.g., product number EC 250-90).

Figure 2A:
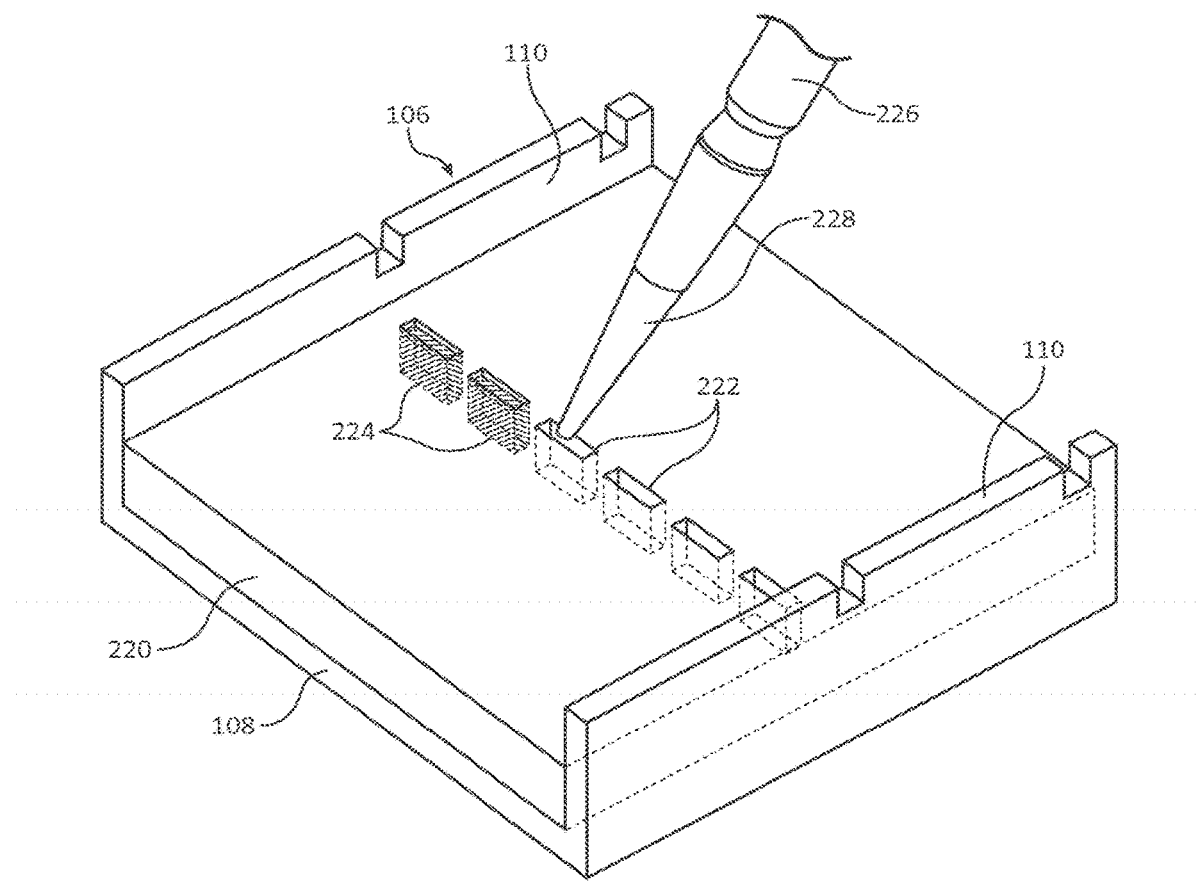
FIG. 2A is a perspective view of an embodiment of a medium in a cassette which may be used with the system of FIG. 1.
Figure 2B:
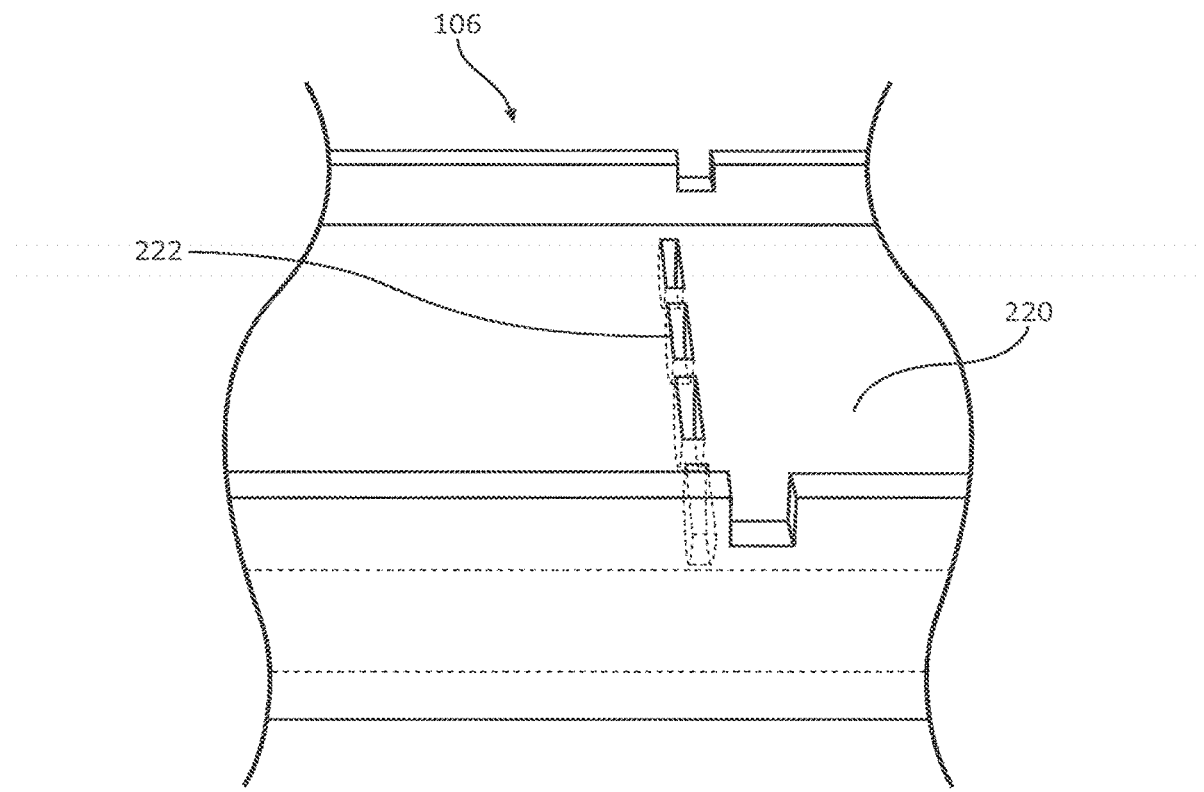
FIG. 2B is a partial perspective view of another embodiment of a medium in a cassette which may be used with the system of FIG. 1.
Figure 2C:
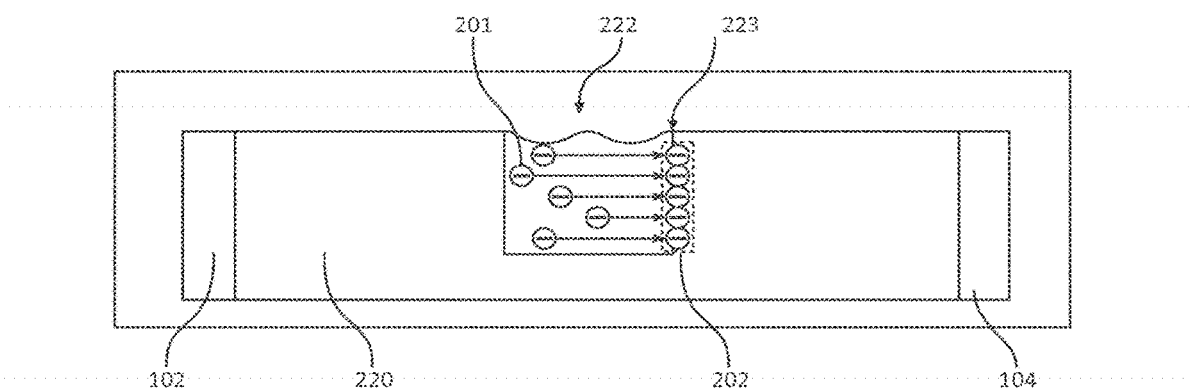
FIG. 2C depicts a side view of the medium and system of FIG. 2B.

FIG. 2A depicts an embodiment of a medium in a cassette 106 comprising a bottom plate 108 and sides 110, which may be used with the system 100. A medium 220 is disposed in the cassette 106 with a plurality of wells 222 in the medium 220. A sample 224 is added in some wells 222 with a pipette 226 comprising a pipette tip 228. Although the medium is shown as a top load gel slab, media in other forms, including but not limited to vertical gel slabs, can be used.

Figure 2D:
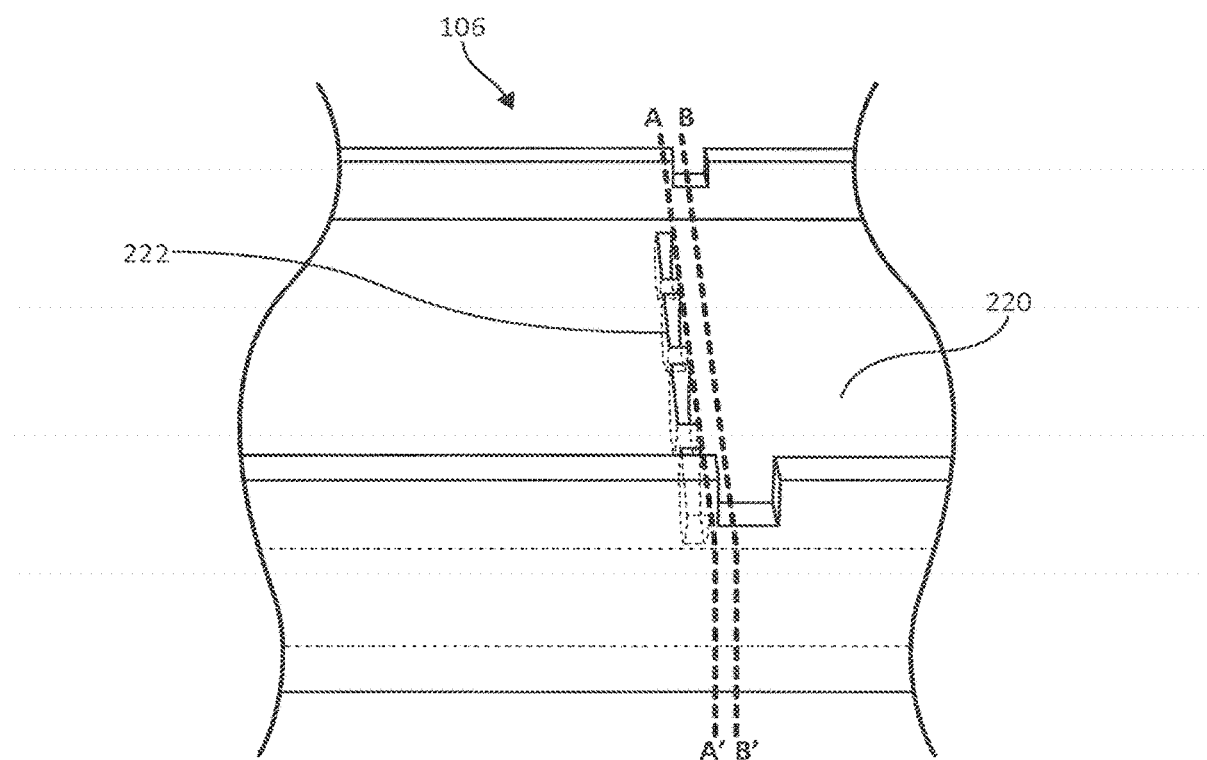
FIGS. 2D and 2E illustrate excision of a portion of the medium of FIG. 2B.
Figure 2E:
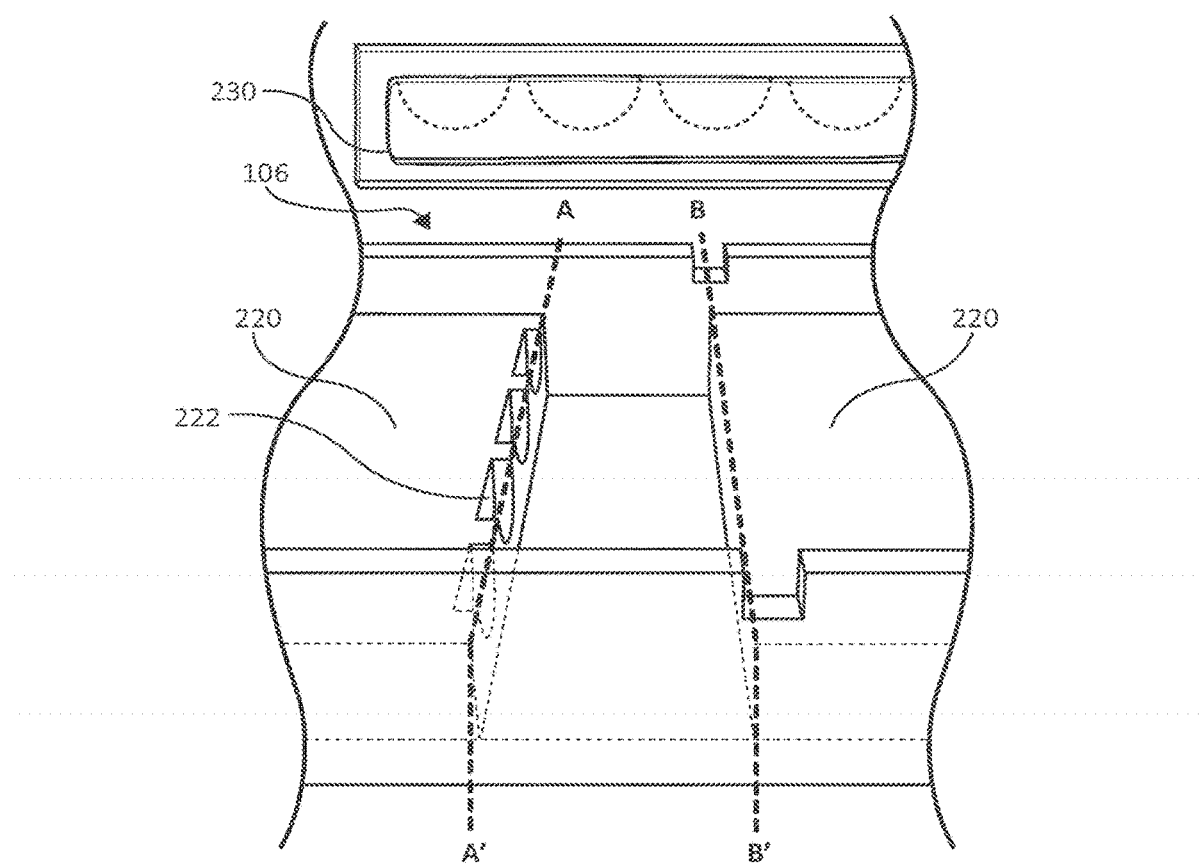

FIGS. 2B-2H illustrate an embodiment where a medium 220 is disposed in a cassette 106 and has a plurality of wells 222 in the medium 220. A sample is added and a potential is applied between negative electrode 102 and positive electrode 104 as described elsewhere herein to cause contaminant material to enter the medium while the cells 201 and/or viruses accumulate or become embedded on the wall 223 of the well 222, depicted in FIG. 2C as concentrated cells 202. As shown in FIGS. 2D-2E, a portion 230 of the medium 220, including at least a portion of the wells 222, is excised, such as by cutting the medium along planes of excision defined by lines A-A' and B-B', or otherwise removed from the medium. In some embodiments, the excision can be robotically automated.

Figure 2F:
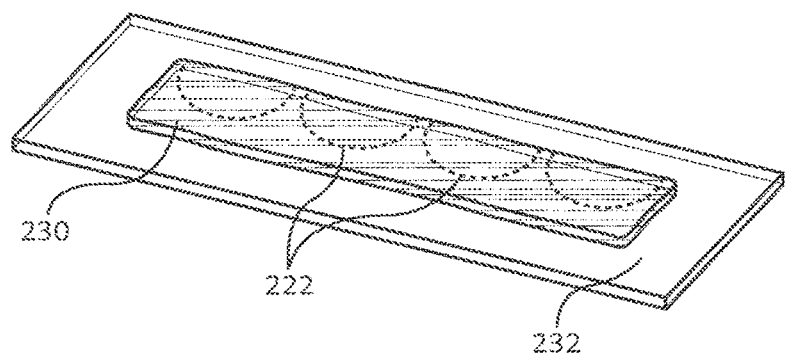
FIGS. 2F, 2G and 2H depict the excised portion of the medium of FIGS. 2D and 2E on a solid surface.
Figure 2G:
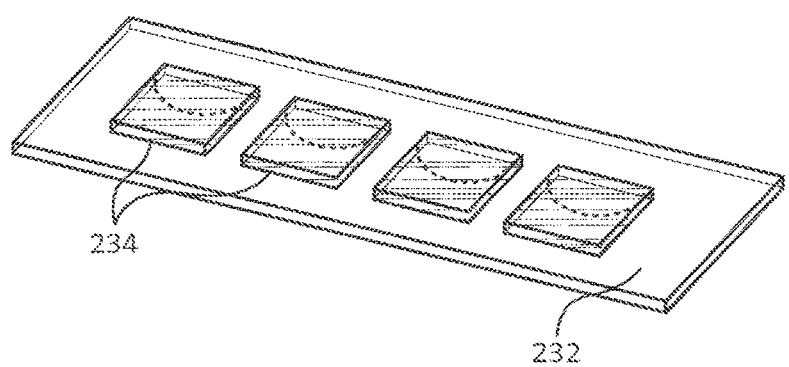
Figure 2H:
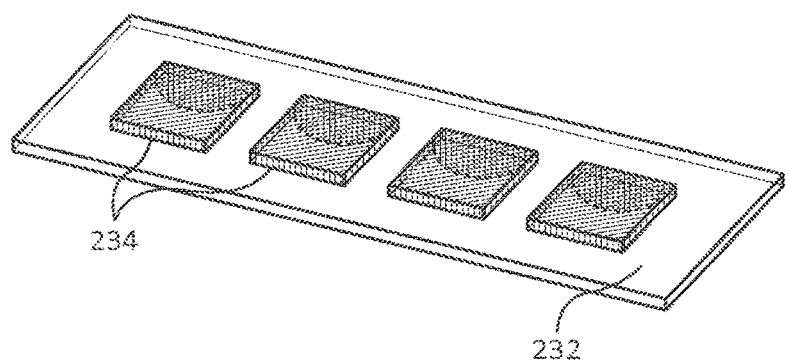
Figure 21:
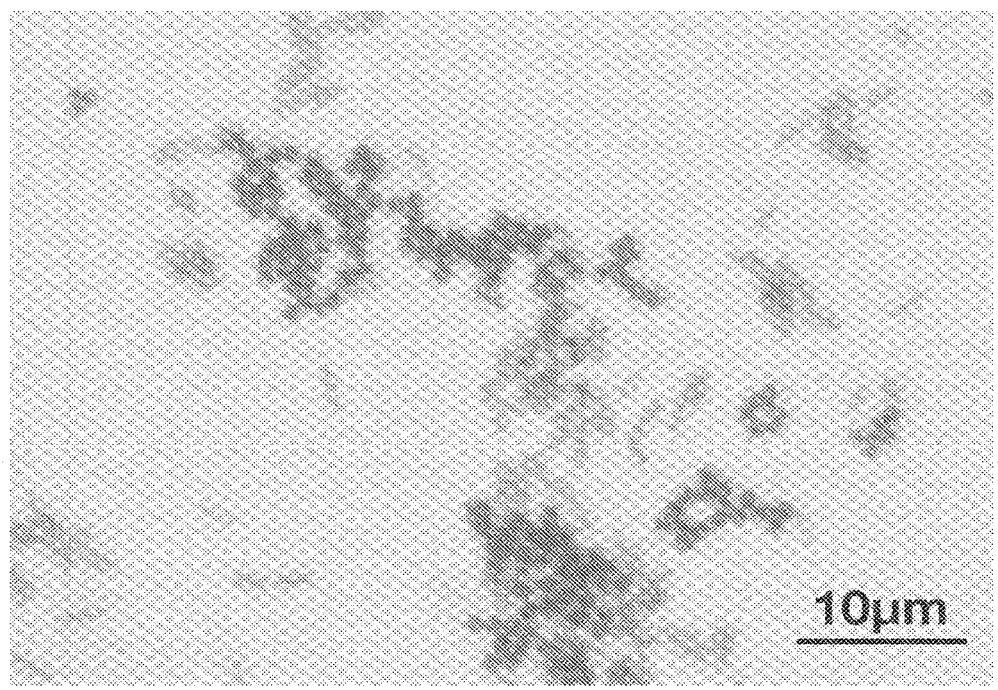

Following excision, the excised portion of the medium may be fixed, for example, for staining or extracting molecular samples for analysis. In some embodiments, and as shown in FIGS. 2F and 2G, the excised portion 230 may be placed on a solid surface 232, such as a glass slide, and the excised portion 230 may be sectioned at each well 222 into sections 231. The sections 231 of excised portion 230 may be dried, Gram stained, and detected as indicated in FIGS. 2H-2I. In some embodiments, a prepared slide (e.g., wherein the sectioned, excised portion has been dried) can be introduced into automated Gram staining equipment.

Figure 2J:
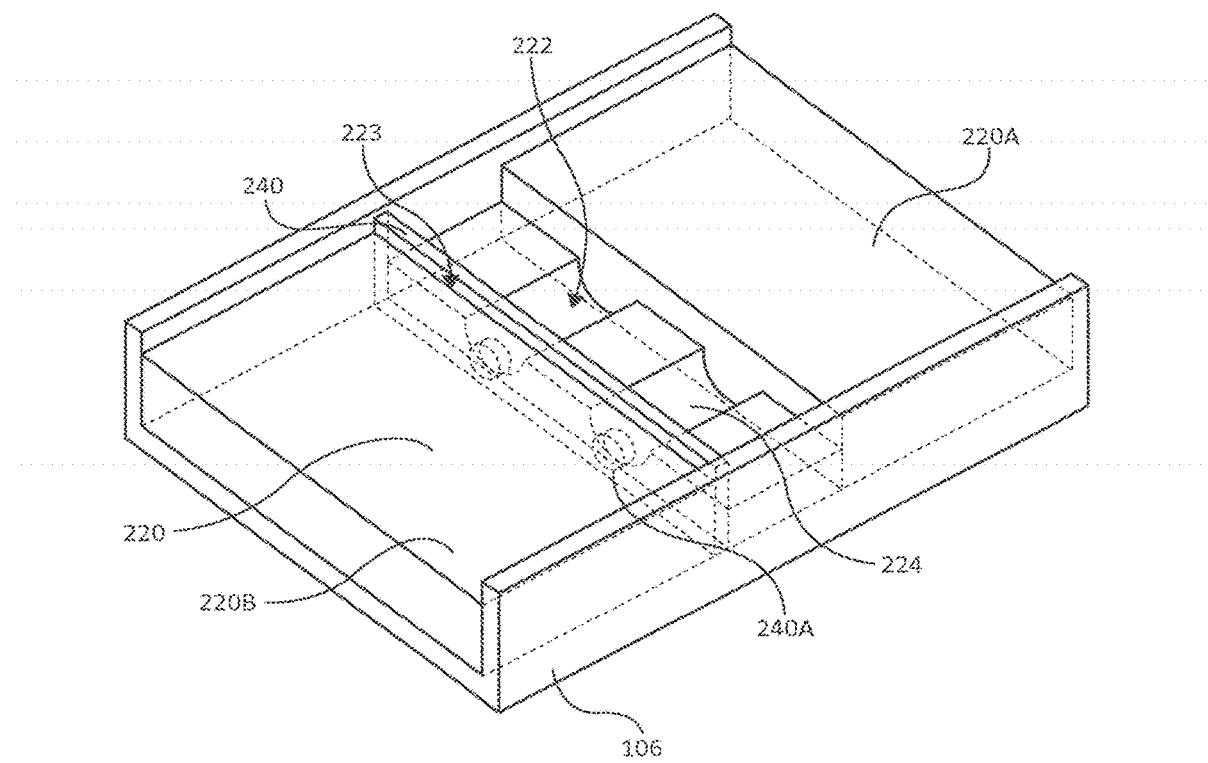
FIG. 2J is a top view of a medium in a cassette which may be used with the system of FIG. 1, wherein a localization device is used to localize the cells and/or viruses.
Figure 2K:
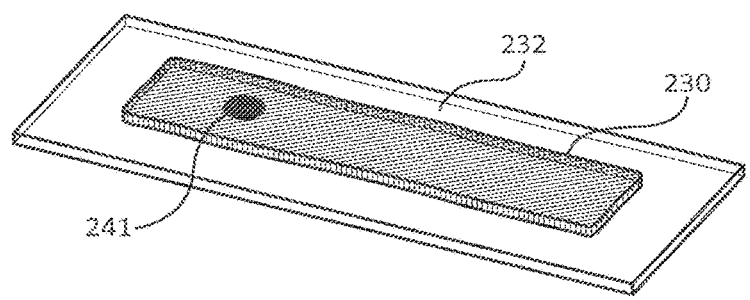
FIG. 2K depicts Gram stained microorganisms that may be detected in accordance with the systems and methods described herein.

In some embodiments, the cells and/or viruses may be localized on the wall of the well by, or with the help of, a localization device. FIGS. 2J and 2K depict an embodiment illustrating a localization device 240 and localized cells 241. FIG. 2J is a top view of a gel medium that utilizes non-conductive materials as a localization device to distort the electric field resulting in localized concentration of cells and/or viruses, such as microorganisms. FIG. 2J illustrates an embodiment where the medium 220 is disposed in the cassette 106 showing a plurality of wells 222, including a plastic well 224, in the medium 220. The medium 220 includes a proximal end 220*a* and a distal end 220*b*. Disposed between the wells 222 and the medium 220 is a localization device 240 comprising a non-conductive material including at least one hole or aperture 240*a*. A sample is added and a potential is applied as described elsewhere herein to cause contaminant material to enter the medium while the cells and/or viruses accumulate or become embedded on the wall 223 of the well 222. In this embodiment, the sample flows through the aperture 240a in the non-conductive localization device 240, thereby localizing the cells and/or viruses that accumulate or become embedded on the wall 223 of the well 222, as described with reference to FIG. 2C. In this embodiment, the non-conductive localization device 240 prevents or inhibits the sample from flowing anywhere but through the aperture(s) 240a. In one embodiment, the non-conductive material may be a plastic film. As described above with reference to FIGS. 2D-2I, a portion of the medium 220, including at least a portion of the wells 222, is excised or otherwise removed. The excised portion 230 may be placed on a solid surface 232, such as a glass slide, and may be dried, Gram stained, and detected. FIG. 2K depicts Gram stained localized microorganisms 241 that have been localized in accordance with the methods and systems described herein.

While FIGS. 2J and 2K depict an embodiment of a system and method for localization using a localization device 240 comprising non-conductive materials, other methods and devices for localization may also be used. In one embodiment, the localization device is a conductive material, such as a metal or metal alloy wire, that is embedded in or placed near a distal end 220b of the medium 220 (i.e., downstream relative to the direction of migration). When a potential is applied, the cells and/or viruses localize on the wall of the well in a location corresponding to the position of the conductive material. That is, where the conductive material is a straight metal wire, the cells and/or viruses localize on the wall of the well in a straight line corresponding to the line of the metal wire. In another embodiment, the localization device includes large and small (or discrete) electrodes are used. For example, a large electrode, such as a sheet electrode, may be placed at a proximal location relative to the proximal end 220a of the medium 220. A small electrode may be placed at a distal location relative to the distal end 220b of the medium 220. When a potential is applied, the cells and/or viruses localize on the wall of the well in a location corresponding to the location of the small electrode. In still other embodiments, the localization device is a discontinuous buffer system. In such a system, the conductivity inside the well is different from the conductivity outside the well. For example, where a well is made of the medium, the conductivity of the sample and the conductivity of the well are different. When a potential is applied, the cells and/or viruses localize on the wall of the well due, at least in part, to this conductivity difference.

Dyes can be used in samples to pre-label or added to provide a tracking dye for purposes of a quantitative reference or sample transfer quality control indicator. Examples of dyes include colorants, bio-active adjuncts such as labeled antibodies, vital stains, mortal stains (such as propidium iodide and the like). Zwitterionic or neutrally charged dye molecules can be used to monitor electro-osmotic flow.

The potential applied across the medium effective for removal of contaminants can be applied for a variable time and is dependent on the sample conductivity. For samples retrieved using normal saline and having a conductivity near that of normal saline, for example, the potential can be applied from 1 to 60 minutes.

In some embodiments, the method includes an asymmetric alternating potential. In other embodiments, the potential is a constant potential. In various embodiments, the applied potential induces electro-osmotic flow that is used to remove contaminants having a neutral charge. The potential can be reversed in polarity to displace cells and/or viruses from the surface of the medium. In some embodiments, the method includes applying a tangential flow across the medium to remove non-permeable contaminants from the surface of the medium. The tangential flow may be applied by flowing the sample over the medium. The tangential flow may be generated using additional buffer that is not the sample. The flow can be continuously cycled over the medium.

When a sample is taken from a patient, there are various components in the sample. For example, in a patient suffering from pneumonia, a sample may include saline, anionic and cationic species, pulmonary surfactants, bacteria, mucus, blood, host cells such as white blood cells, and/or lung tissue cells. Mucus components include, but are not limited to, mucoidal glycoproteins, proteins, extra-cellular nucleic acids, F-actin, lysed white blood cell fragments. Blood components may include, but are not limited to, red cells, white cells, platelets, and plasma. Plasma components may include, but are not limited to, sugar, fat, protein and salt solution, platelets, blood clotting factors, sugars, lipids, vitamins, minerals, hormones, enzymes, antibodies, and other proteins including heme, albumins, immunoglobulins, fibrinogens, regulatory proteins, lipoproteins (chylomicrons, VLDL, LDL, HDL), transferrin, prothrombin, enzymes, proenzymes, residual antibiotics used to treat the patient, and hormones. Lung tissue components include host epithelial cells (intact or lysed). The cells in the alveolar walls of the lung produce and secrete pulmonary surfactant. Pulmonary surfactant is a mixture of phospholipids and proteins. White blood cells may also be present in lung samples. All the above components may be solubilized.

In some embodiments, the cells include blood cells, fungal cells, bacterial cells, or microorganisms including parasites. Examples of blood cells include red blood cells and white blood cells. In some variations, the white blood cells can be neutrophils.

In various embodiments, microorganisms can include bacteria, fungi, algae, and protozoa. In one aspect, the microorganisms are bacteria. The microorganisms can be pathogenic to humans and animals. Suitable microorganisms include any of those well established in the medical art and those novel pathogens and variants that emerge from time to time. Exemplary bacteria that can be detected with the disclosed methods and devices include, but are not limited to, genera such as *Bacillus, Vibrio, Escherichia, Shigella, Salmonella, Mycobacterium, Clostridium, Cornyebacterium, Streptococcus, Staphylococcus, Haemophilus, Neissena, Yersinia, Pseudomonas, Chlamydia, Bordetella, Treponema, Stenotrophomonas, Acinetobacter, Enterobacter, Klebsiella, Proteus, Serratia, Citrobacter, Enterococcus, Legionella, Mycoplasma, Chlamydophila, Moraxella, Morganella*, and other human pathogens encountered in medical practice. Included in the genera are various species. For example, *Klebsiella* includes, but is not limited to, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*. Examples of viruses include viroids.

Similarly, microorganisms may comprise fungi. Exemplary fungi that can be purified and/or detected with the disclosed methods and devices include, but are not limited to, genera such as *Candida, Aspergillus*, and other human pathogens encountered in medical practice. Exemplary viruses that can be detected with the disclosed methods and devices include, but are not limited to, orthomyxoviruses (e.g., influenza virus), paramyxoviruses (e.g., respiratory syncytial virus, mumps virus, measles virus), adenoviruses, rhinoviruses, coronaviruses, reoviruses, togaviruses (e.g., rubella virus), parvoviruses, poxviruses (e.g., variola virus, vaccinia virus), enteroviruses (e.g., poliovirus, coxsackievirus), hepatitis viruses (including hepatitis A, B, and C), herpesviruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLVI and II), papovaviruses (e.g., papillomavirus), polyomaviruses, picornaviruses, and the like.

For example, viruses that can be purified and/or detected with the disclosed methods include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain). Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses).

DNA viruses that can be purified and/or detected with the disclosed methods include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Retroviruses that can be purified and/or detected with the disclosed methods include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

Bacteria can be classified as gram-negative or gram-positive. Exemplary gram-negative bacteria that can be purified and/or detected with the disclosed methods include, but are not limited to: *Escherichia coli* (e.g., K-12 and O157:H7), *Shigella dysenteriae*, and *Vibrio cholerae*. Exemplary gram-positive bacteria that can be purified and/or detected with the disclosed methods include, but are not limited to: *Bacillus anthracis, Staphylococcus aureus*, pneumococcus, gonococcus, and streptococcal meningitis.

Examples of bacteria that can be purified and/or detected with the disclosed methods, include without limitation: *Acinetobacter baumanii, Actinobacillus* sp., Actinomycetes, *Actinomyces* sp. (such as *Actinomyces israelii* and *Actinomyces naeslundii*), *Aeromonas* sp. (such as *Aeromonas hydrophila, Aeromonas veronii biovar sobria (Aeromonas sobria)*, and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as *enterotoxigenic E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio fumisii*), *Yersinia* sp. (such as *Yersinia enterocolitica*, *Yersinia pestis*, and *Yersinia pseudotuberculosis*) and *Xanthomonas maltophilia* among others.

Protozoa that can be detected with the disclosed methods include, but are not limited to: *Plasmodium*, *Leishmania*, *Acanthamoeba*, *Giardia*, *Entamoeba*, *Cryptosporidium*, *Isospora*, *Balantidium*, *Trichomonas*, *Trypanosoma*, *Naegleria*, and *Toxoplasma*. Exemplary fungi include, but are not limited to, *Coccidiodes immitis* and *Blastomyces dermatitidis*.

The methods and systems described herein can be used to identify host cells harboring viruses. In some examples, the cells are first purified, and subsequently the cells are manipulated to either produce viruses, or to identify nucleic acids in the cells.

The biological sample can be obtained from any number of sources, including, but not limited to, bodily fluids (including, but not limited to, blood, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms and semen) of virtually any organism, including mammalian samples and human samples, as well as environmental samples (including, but not limited to, air, agricultural, water and soil samples). In addition, samples can be taken from food processing, which can include both input samples (e.g., grains, milk or animal carcasses), samples in intermediate steps of processing, as well as finished food ready for the consumer. The method can be used for veterinary applications. The methods can be also used for the analysis of milk in the diagnosis and treatment of mastitis, and the analysis of respiratory samples for the diagnosis of bovine respiratory disease. Furthermore, the methods provide for the rapid detection of the presence of potential biological warfare agents in a sample.

Biological samples can range from less than a milliliter to up to a liter for certain respiratory lavage fluids, and can further range in bacterial concentration from less than one bacterium to greater than $10^9$ bacteria per milliliter. Furthermore, the sample can be present in blood, urine, sputum, lavage fluid or other medium. The sample can be concentrated prior to using the described methods for purifying cells and/or viruses from the sample. Sample concentration both concentrates the sample so that bacteria that are present in small numbers can all be effectively introduced into the system and adequately sampled, as well as so the background liquid medium can be normalized, or in some cases eliminated or reduced, to have consistent properties upon introduction to the system. Sample concentration can be performed by centrifugation, combining samples, removing solvents, and the like. It should be noted, however, that certain samples provided in the description can be used without concentration or other modification.

The rapid detection of various cells and/or viruses is useful for a patient suffering from various diseases and disorders. For example, pneumonia can result from a variety of causes, including infection with bacteria, viruses, fungi, or parasites, as well as chemical or physical injury to the lungs. However, some samples of cells and/or viruses contain contaminants that interfere with their detection. Purification of a microorganism (or virus or other cell), and detection of the type and amount of a microorganism (or virus or other cell) present in a sample, are helpful to diagnose and treat a patient effectively.

In other embodiments, the cells are selectively lysed. For example in the case of intracellular targets, the mammalian cells can be lysed, releasing intracellular microorganisms prior to, during, or after the purification described herein.

Contaminants

Contaminants are removed from the biological sample into the medium. Contaminants that can be removed using the disclosed methods and devices include ionic species, including, but not limited to, mono or divalent cations and anions, released intracellular materials, phospholipids, extracellular proteins, mucins, pulmonary surfactants, mucus plugs, pus, glycoproteins, and nucleic acids. Removing contaminants avoids other time intensive preparation steps such as vortexing and centrifugation. In various aspects, the removed contaminants interfere with cells (such as microbial cells) and/or virus surface immobilization, detection, and imaging. Cells and/or viruses remain in the well, and can be recovered. In certain aspects of the purification methods, certain components, such as cellular membrane fragments and larger cellular fragments, are not removed from the sample.

Medium

Organogels, xerogels, and aerogels may also be utilized as the medium. Aerogels include, but are not limited to, silica aerogel, carbon aerogels, alumina, cadmium, and selenide aerogels. Organic aerogels, such as SEAgel, are made of agar. Aerogels made of chalcogens such as sulfur, selenium, and other elements may also be of utility.

In various embodiments, the medium is a hydrogel. In some embodiments, hydrogels are a network of polymer chains that are hydrophilic. Hydrogels can be highly absorbent natural or synthetic polymers, and in some instances can contain over 99% water. In general, hydrogels are solid, yet porous media.

The concentration of the hydrogel affects the migration speed of the contaminants through the hydrogel. Increasing the concentration of the hydrogel decreases the pore size within the hydrogel. Additionally, contaminants with smaller molecules move faster and migrate further than contaminants with larger molecules.

The charge of the hydrogel also affects the migration speed of the contaminants through the hydrogel. Each contaminant molecule migrates to the electrode that carries a charge opposite of that of the contaminant molecule. Most biological materials have a net negative surface charge. Some have a net positive charge if the material has an excess of amines or other positively-charge moieties exposed to the surface. The charge is considered neutral if it is a balance of positive and negative, or uncharged, such as complexes coated with neutral materials that envelope and screen charged materials within. The uncharged material will migrate in the direction of electro-osmotic flow, if present.

The pH of the hydrogel also affects the migration speed of the contaminants and the targets. In some embodiments, the pH is selected to enhance mobility of the contaminants relative to the cells and/or viruses. In some embodiments, a pH may be selected such that the cells and/or viruses are substantially near the isoelectric point, minimizing the cells' and/or viruses' mobility relative to the contaminants. In other embodiments, the pH may be selected to be substantially different from the isoelectric point such that the direction of the cells' and/or viruses' mobility is reversed relative to the contaminants.

In some embodiments, a medium contains nutrients that promote the viability of the cells and/or viruses.

Media used in the systems described can separate contaminant molecules based on both their size and their charge.

The hydrogel's porosity is directly related to the concentration of agarose in the medium. Various levels of effective viscosity can be selected, depending on the experimental objectives.

Examples of hydrogels are alginates, as disclosed in Gadkari, 2007, "Optimal hydrogels for fast and safe delivery of bioactive compounds", Thesis of Drexel University; ethyl-vinyl-acetate copolymer as disclosed in U.S. Pat. No. 3,854,480; esters of hydantoic acid as disclosed in U.S. Pat. No. 3,792,081, olefin saturated polyester 500-8000, polyethylene glycol (PEG) 200-1500, ethyl-vinyl-acetate copolymer 20-40% VA (20-30K), chlorinated polyethylene 25-45% Cl—(20-30K), ethyl-ethylacrylate copolymer 20-40% EA (20-30K), and ethylene vinyl chloride copolymer 25-45% Cl—(20-30K) as disclosed in U.S. Pat. No. 3,938,515; methyl-methacrylate copolymer and glyceryl-methyacrylate copolymer as disclosed in U.S. Pat. No. 3,957,362; ethylene-vinyl-actetate copolymer 4-80% VA (20-30K) as disclosed in U.S. Pat. No. 4,069,307; polysiloxanes as disclosed in U.S. Pat. No. 4,136,250; hydrophilic dihydroxyalkyl acrylate and insoluble copolymer as disclosed in U.S. Pat. No. 4,267,295; cellulose triacetate as disclosed in U.S. Pat. No. 4,220,152; acrylamide, vinylpyrrolidone, and polyethyleneoxide diol as disclosed in U.S. Pat. No. 4,423,099; poly-amino acid homopolymers and copolymers as disclosed in U.S. Pat. No. 4,351,337; polyglutamic acid ethyl-glutamate copolymer (5-50% GA, 80-500 KDa) as disclosed in U.S. Pat. No. 4,450,150; polyoxyethlyene-polyoxypropylene copolymer thermoset as disclosed in U.S. Pat. No. 4,478,822; vinyl cross-linked copolymers of insoluble and soluble monoolefinic esters as disclosed in U.S. Pat. No. 4,548,990; copolymers with N-vinyl-2-pyrrolidone and methacrylates as disclosed in U.S. Pat. No. 4,693,884; polyanhydride as disclosed in U.S. Pat. No. 4,657,543; colpolymer of poly(alkylene oxide) and cyclic ester of alpha hydroxy acid (glycolide) as disclosed in U.S. Pat. No. 4,882,168; polyacrylonitrile-nitric acid copolymer as disclosed in U.S. Pat. No. 5,218,039; N-morpholinoethyl methacrylate and 2-hydroxyethyl methacrylate copolymer as disclosed in U.S. Pat. No. 4,857,313; cross-linked copolymers of vinyl pyrrolidone and allylamine as disclosed in U.S. Pat. No. 4,772,484; water soluble polyacetals having molecular weights from about 5,000-30,000 as disclosed in U.S. Pat. No. 4,713,441; thermoplastic hydrogels of polyvinyl pyrrolidone (PVP) and polyvinyl acetate (PVA), and gelatin as disclosed in U.S. Pat. No. 5,002,792; alginic acid with Ca++, Ba++ or Zn++, pectic acid with Ca++, Ba++ or Zn++, hyaluronic acid with Ca++, Ba++ or Zn++, polyglucuronic acid with Ca++, Ba++ or Zn++, polymanuronic acid with Ca++, Ba++ or Zn++, polygalacturonic acid with Ca++, Ba++ or Zn++, polyarabinic acid with Ca++, Ba++ or Zn++, and kappa-carrageenan with Ca++, Ba++ or Zn++, as disclosed in U.S. Pat. No. 5,089,606; charged side-chain polyphosphazenes with Ca++ cross-linking as disclosed in U.S. Pat. No. 5,149,543; carboxymethylcellulose as disclosed in U.S. Pat. No. 5,208,037; agarose as disclosed in U.S. Pat. No. 3,961,628; polyacrylamide as disclosed in U.S. Pat. No. 6,391,937; pluronic 127, N-isopropylacrylamide (NiPAM); and blends (block copolymer, etc.) of all the above listed hydrogels.

Agarose is a linear polymer, made up of the repeating monomeric unit of agarobiose. Agarobiose is a disaccharide made up of D-galactose and 3,6-anhydro-L-galactopyranose. Agarose pectin or sulfonated agarose can be used as the hydrogel. Agarose can be obtained from Lonza (Rockland, Me.) under the brand name SeaKem™. In certain embodiments, the concentration of the agarose gel for effectively removing contaminants is from 0.1-2.0% w/v.

Purified agarose hydrogels may be purchased for use in the described method. An example of a commercial purified hydrogel can be obtained from Invitrogen (Carlsbad, Calif.) under the brand name E-Gel® EX Starter.

Polyacrylamide is a polymer ($-CH_2CHCONH_2-$) formed from acrylamide subunits. It can be synthesized as a simple linear-chain structure or cross-linked, typically using N,N'-methylenebisacrylamide. In the cross-linked form, polyacrylamide is highly water-absorbent, forming a soft gel. Polyacrylamide can be obtained from BioRad (Hercules, Calif.).

Purified polyacrylamide hydrogels may be purchased for use in the described method. An example of a commercial purified hydrogel can be obtained from BioRad (Hercules, Calif.).

Preconditioning of a medium can be performed. Preconditioning of a medium is often done to remove impurities found in the medium. For example, providing a potential across a hydrogel helps mobile impurities to migrate outside of the hydrogel. The potential can be, for example, 50V, 75V, 95V, 100V, 150V, 200V, 250V, 300V, 350V, 400V or 500V. In various embodiments, the potential can be provided for a period of time, such as at least 2 minutes, at least 5 minutes, at least 10 minutes, at least 15 minutes, at least 30 minutes, at least 45 minutes, at least 60 minutes, at least 120 minutes, or at least 180 minutes.

In various embodiments, the medium can be a filter. Examples of filters include those available from Pall Corporation (Port Washington, N.Y.), such as hydrophilic polypropylene, ahydrophilic, low binding material with pore sizes of 0.2 µm and 0.45 µm; polytetrafluoroethylene (PTFE), a hydrophobic, high binding material with pore sizes of 0.2 µm, 0.45 µm, 1 µm, 2 µm and 3 µm; glass fiber, a hydrophilic, moderate binding material with a pore size of 1 µm; nylon, a hydrophilic, low binding material with pore sizes of 0.2 µm and 0.45 µm; polyvinylidene fluoride (PVDF), a hydrophilic, low binding material with pore sizes of 0.2 μm and 0.45 μm; PES (Supor®), a hydrophilic, low binding material with pore sizes of 0.1 μm, 0.2 μm, 0.45 μm, and 0.8 μm; vinyl/acrylic copolymer, a hydrophobic material that may be used for air sampling and has pore sizes of 0.45 μm and 0.8 μm; polyvinyl chloride (PVC), which may also be used for air sampling and has pore sizes of 5 μm; hydrophilic mixed cellulose esters, a high binding material with a pore size of 0.45 μm; hydrophilic acrylic copolymer, which may be used as a pre-filter on a support and has pore sizes of 0.2 μm, 0.45 μm, 0.8 μm, 1.2 μm, 3 μm, and 5 μm; and nitrocellulose, a high binding material with a pore size of 0.2 μm. Examples of filters available from Millipore (Billerica, Mass.) include PTFE (LCR), a hydrophilic, moderate binding material with pore sizes of 0.2 μm and 0.45 μm; PVDF (Durapore™), a hydrophilic, low binding material with pore sizes of 0.2 μm and 0.45 μm; PTFE (Fluoropore™), a hydrophilic, low binding material with pore sizes of 0.2 μm and 0.45 μm; nylon, a hydrophilic, low binding material with pore sizes of 0.2 μm and 0.45 μm; glass fiber, a hydrophilic, moderate binding material with a pore size of 1 μm; and hydrophilic mixed cellulose esters, a high binding material with exemplary pore sizes of 0.2 μm, 0.45 μm, and 0.8 μm. Filters can have pore sizes of greater than or equal to about 0.01 μm, 0.05 μm, or 0.1 μm, 0.2 μm, 0.4 μm, 0.6 μm, 0.8 μm, 1.0 μm, 1.5 μm, 2.0 μm, 2.5 μm, 3.0 μm, 4.0 μm, or 5.0 μm. Filters can have pore sizes of less than or equal to about 5.0 μm, 4.0 μm, 3.0 μm, 2.5 μm, 2.0 μm, 1.5 μm, 1.0 μm, 0.8 μm, 0.6 μm, 0.4 μm, 0.2 μm, 0.05 μm, or 0.01 μm.

In various embodiments the method includes adding a chemical agent to the medium to increase the permeability of the medium and/or increase the ability of the contaminant to enter the medium.

Examples of chemical agents include reducing agents, including, but not limited to, dithiothreitol (DTT), tris(2-carboxyethyl)phosphine (TCEP), and mercaptoethanol reducing agents; denaturing agent using surfactants, including, but not limited to, sodium lauryl sulfates, non-ionic surfactants such as Triton X-100, Tween-20, or chaotropic agents, including, but not limited to, urea, thiourea, or guanidinium chloride; chelating agents that can coordinate molecules such as calcium, magnesium, and other divalent and trivalent ions (including metal ions), including ethylenediaminetetraacetic acid (EDTA) and ethylene glycol tetraacetic acid (EGTA); cleavage agents including proteases, nucleases, glyconases, lipases; and excipients such as polyethylene glycol. In some embodiments a combination of one or more chemical agents can be utilized.

Viscous gels include cellulose ethers (such as hydroxylethyl cellulose or Methocel™ (Dow (Midland, Mich.)) and soluble polymer viscosity modifiers (such as polyethylene glycol, polyvinylpyrrolidone, dextrans, pluronic surfactants, and alginates). In a viscous gel, the pore size is not defined. The separation is based on retarded flow of the cells in the viscous medium.

In some embodiments, agents can be added to or used to treat the medium to control electroosmotic flow. In some embodiments, it may be desirable to increase or decrease electroosmotic flow.

Sample Mixing

To analyze a representative sample, the sample should be substantially uniform. In some embodiments, the homogenization of a sample can be done by a sample mixing or stirring step. Mixing the sample acts to re-suspend any caked material formed on the walls of the well.

In various embodiments, the method includes mixing a sample using a pipette tip. See, for example, the pipette tip 228 in FIG. 2A. The sample is passed through the narrow opening of the pipette to shear and homogenize the sample.

Buffer Solutions

In various embodiments, the method includes placing a buffer in contact with the medium.

In some embodiments, the mixing parameters of the buffer are designed to maximize the removal of debris and non-target material.

In some embodiments, the buffer can be replenished to prevent accumulation of undesirable electrophoresis products. For example, undesirable effects pH gradients generated at the cathode and anode and in proximity to the sample can be substantially minimized by buffer replenishment or replacement, potentially using continuous flow.

In various embodiments, electrophoretic buffers utilize pairs of redox mediators. In certain embodiments, these redox mediators facilitate low voltage electrophoresis that permits cell viability to be maintained. These redox mediators may also enable the use of electrode materials that have limited utility in high voltage electrophoresis (for example, indium tin oxide, "ITO" electrodes). In addition, these redox mediators find use in "closed systems" (i.e., systems not open to the atmosphere). In closed systems, bubble formation and generation of other reactive species during the electrophoresis step, which can cause a number of problems, is prevented, and closed systems also help to prevent the exposure of the technician to potentially infectious samples, as well as reducing problems associated with discarding biological samples In some embodiments, the buffer is placed in a reservoir in contact with the medium. In various embodiments, the medium is not submerged in the buffer.

Buffers include, for example, various electrophoresis buffers including zwitterionic buffers, neutral buffers such as phosphate-buffered saline (PBS), lower or higher pH buffers, and hypotonic or hypertonic buffers. In some embodiments, borate and other selected ions and counter-ions are included to facilitate effective electrophoresis.

In some embodiments, the buffer solution includes histidine and tris(hydroxymethyl)aminomethane. Histidine has low conductivity. Tris(hydroxymethyl)aminomethane has some conductivity but has low mobility. Histidine has pKa values close to physiological values providing adequate buffering capacity. Tris(hydroxymethyl)aminomethane can be obtained from Sigma-Aldrich (St. Louis, Mo.) as Trizma® base (Sigma, T1503).

In some embodiments, the sample (in 150 mM NaCl) is desalted to remove cationic and anionic species that may interfere with subsequent analysis. In some embodiments, desalting allows successful concentration and capture of the microorganism.

Electrophoretic mobility can be buffer dependent due to zeta potential variability with salt concentration, valency of salts present in the buffer, and the pH of the buffer. Bacteria can lose charge as the concentration of salt increases or as the pH is lowered below a certain pH, for example, pH 5.0. Divalent and trivalent salts are more effective quenchers than monovalent salts. For example, $CaCl_2$ is more effective than NaCl to quench a charge. Certain agents such as chelators, including, but not limited to, ethylenediaminetetraacetic acid (EDTA) and ethylene glycol tetraacetic acid (EGTA), both available from Sigma-Aldrich, can be used to control the concentration of charged species in the sample.

Wells

Figure 8:
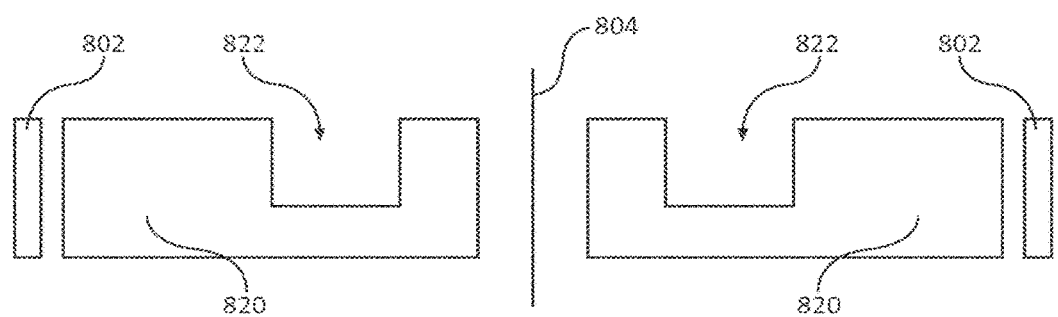
FIG. 8 is a side view of an embodiment of a circular well formed in a medium with corresponding electrodes

As shown in FIG. 2A, one or a plurality of wells can be formed in the medium. The wells are molded into the gel. For example, a custom well-forming comb can be used to create the appropriate well shape. Wells include side-walls that can be substantially vertical or diagonal. In various embodiments, the method includes wells that are non-rectangular shaped. In various embodiments, the wells are substantially chamfered to eliminate sharp edges in the well, enhancing target recovery. In some embodiments, the wells can hold various sample sizes. In various embodiments, the wells can hold from 10 µL to 500 µL. In some embodiments the wells are 5 to 250 mm wide. Multiple wells can be used for a sample. As illustrated in FIG. 8, a well 822 in medium 820 may be circular, surrounding an electrode such as cathode 804, and the counter electrodes may surround the well, such as the illustrated anode ring 802. In a circular well configuration, a sample placed in well 822 surrounds the cathode 804. In such an embodiment, a run buffer sheath may flow over cathode 804 to remove electrode byproducts during electrophoresis.

Figure 3:
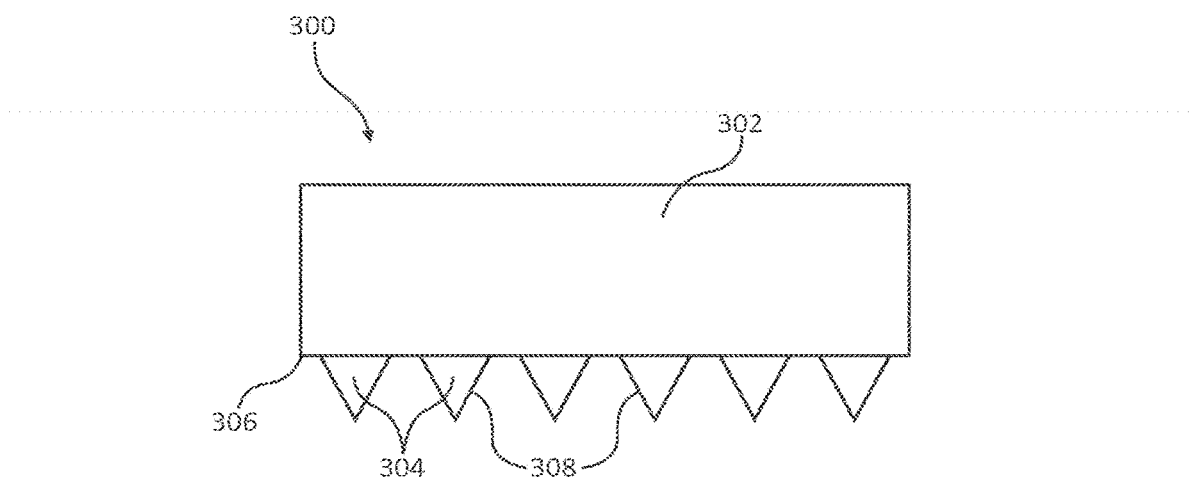
FIG. 3 is a side view of an embodiment of a custom well-forming comb used to make wells in a medium.

FIG. 3 depicts a side view of an embodiment of a custom well-forming comb 300. A comb body 302 has a plurality of well-forming teeth 304 connected to the comb body 302 by one edge 306. The sides of the teeth 308 form the side-walls of the non-rectangular shaped wells in a medium. In this embodiment the wells are triangular-shaped. The comb 300 is sized and shaped to fit the medium in a cassette, such as the cassette shown in FIG. 2A. In the illustrated embodiment, the comb 300 has six well-forming teeth 304, but could have more or less teeth depending on the size of the cassette.

In a rectangular or square bottomed well, sample solution can wick up the walls of the well. In a triangular shaped well, the sample solution does not tend as strongly to wick up the walls, making it easier to remove the microorganism from the well. In some embodiments, the triangular shaped well is narrowest at the bottom and widest at the top of the well. The well-forming teeth 304 shown in FIG. 3 create a pattern of triangular shaped wells in the medium. In other embodiments, the wells may be round-bottomed wells.

The samples can have high solids (e.g., from 1%-50% weight/volume of solid components). Minimizing the well width minimizes the caking of the solids on the well walls. In some embodiments, the well is 0.0025 inches wide at the widest point.

Chambers

Figure 9:
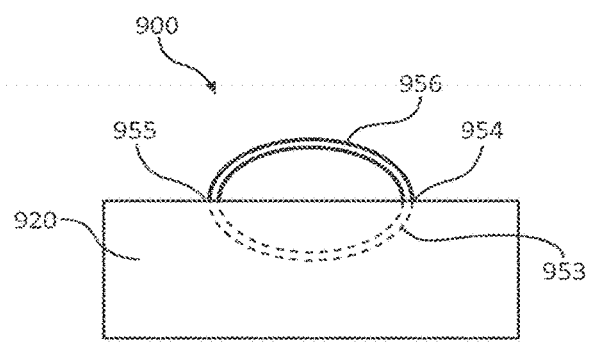
FIG. 9 is a side view of an embodiment of a chamber formed in the medium with an inlet and outlet port enabling sample recirculation.

In various embodiments, the method uses a system 900 wherein one or a plurality of chambers 953 can be formed in a medium 920. The chambers 953 are molded into the gel 920 and have an inlet and outlet port (954 and 955) as shown in FIG. 9. Inlet and outlet ports 954 and 955 are connected by tubing 956 for recirculating a sample through a chamber 953, such as by a peristaltic pump. The chambers may be submerged or partially submerged in buffer, and electrical potential is applied to the system orthogonally to the direction of the recirculating flow of sample.

Electrodes

In various embodiments of the method, an electrode or a plurality of electrodes may be contained within the well or chamber. Additionally, in various embodiments, the electrode or plurality of electrodes may be in contact with the medium or separated a distance from the medium. The electrode or plurality of electrodes may be connected to the medium using salt bridges, buffer, redox mediators, or other conductive charge transfer methods used by those skilled in the art or familiar with techniques used in applications for establishing faradaic current. In some embodiments the electrodes are in physical contact with the chamber walls.

In various embodiments, conductive materials may be utilized to distort the electric field resulting in localized concentration of cells and/or viruses. Electric field distortion may utilize material conductivity differences to accomplish the said localization.

Retention of the Cells and/or Viruses

In various embodiments, the method includes retaining the microorganism. Cells and/or viruses are retained by various filters that exclude the targets (microorganism) from penetrating, for example, tube walls, microchannels (horizontal or vertical), or any geometry that uses a capture surface (specific or nonspecific), mazes, fluidic dead space (eddy cul-de-sacs), and microwells of approximate cellular scale.

Detection Surface

In some embodiments, the method includes retention of cells (such as microbial cells) and/or viruses on a positively charged surface. For example, cells (such as microbial cells) and/or viruses can be captured onto a positively charged detection surface. In other embodiments, the cells and/or viruses may be retained by embedding in the medium.

Detection surfaces are disclosed in, for example, U.S. Pat. No. 6,844,028, incorporated by reference herein in its entirety. Detection surfaces can include those coated with poly-L-lysine, polyethylenimine, or other cationic polymers. Additionally, detection surfaces can include hydrophobic surface coatings.

After the contaminants are removed from the sample by the medium, the microorganism can be detected by a system. In some embodiments, the system comprises an optical sensing system. In some embodiments, the system comprises a microscope.

In some embodiments, the system is an automated system.

In various embodiments, the sequential or simultaneous use of a plurality of electrophoresis electrodes allows multidimensional electrophoresis, i.e., the solution may be targeted, "mixed," or "stirred" in the vicinity of a detection surface to further increase the kinetics of binding. For example, polarities can be reversed to allow cells and/or viruses that may not have bound to the detection surface to travel back "over" the surface, resulting in increased binding. Also, electrodes may be located and field polarity switched according to a programmed sequence so as to provide agitation in two dimensions of a plane, or in three dimensions.

Detection of the Microorganism

In various embodiments, the method includes detecting one or more microorganisms present in the biological sample. In general, biosensor devices are designed to fit into a detection unit, and generally utilize a number of components, which can either be "on-chip" (e.g., part of a biosensor cartridge) or "off-chip" (where some of the components are part of separate device or devices into which the biosensor cartridge fits). These components include, but are not limited to, one or a plurality (e.g., an array) of detection surface(s), concentration modules (which, as outlined herein, frequently are configured with the detection surface(s)), detection modules (again, frequently configured with the detection surface(s)), input and output ports, channels, pumps, mixers, valves, heaters, fluid reservoirs (including sample reservoirs, reagent reservoirs, and buffer reservoirs), concentration controllers (e.g., in the case of electrophoresis, electrical controllers), and data collection and analysis (e.g., computer) components.

An example of a microorganism diagnostic system is described in U.S. patent application Ser. No. 10/888,828 filed Jul. 8, 2004, issued as U.S. Pat. No. 7,687,239, and U.S. application Ser. No. 11/303,803, filed Dec. 16, 2005, issued as U.S. Pat. No. 7,341,841, both of which are incorporated herein by reference in their entirety.

Low levels of cells and/or viruses can be detected with this method. Cells can be measure in terms of cells per mL, colony forming units (CFU, or units) per mL for fungi and/or bacterial microorganisms, and viruses can be measured in particles per mL or plaque forming units per mL (PFU). Levels of cells and/or viruses are described in units per volume, typically per mL volume. Those skilled in the art understand the specific units are typically reported as appropriate for a given target. For exemplary purposes, the concentration ranges below are reported in generic units per mL. For example, levels of 0.1 to $1 \times 10^8$ units/mL can be detected. In various embodiments, cells and/or viruses of levels less than $5 \times 10^8$ units/mL, $3 \times 10^8$ units/mL, $1 \times 10^8$ units/mL, $0.8 \times 10^8$ units/mL, $0.6 \times 10^8$ units/mL, $0.4 \times 10^8$ units/mL, $0.2 \times 10^8$ units/mL, or $0.1 \times 10^8$ units/mL, can be detected.

Membrane-Assisted Purification of Bacterial Cells from Samples

Although gel purification is suitable for some diagnostic applications, it can be desirable to use a different approach for removing contaminants, such as background ions and molecules (e.g., proteins) from biological samples, while retaining pathogenic organisms (e.g., bacteria, viruses). In some instances, excessive amounts of ions and extraneous molecules can inhibit the capture and retention of cells during electrokinetic concentration. Moreover, such ions and extraneous molecules may also interfere with identification and antibiotic susceptibility testing of microbes in the biological sample.

Blood testing protocols that utilize a variant of gel electrophoresis, e.g., gel electro-filtration (GEF), can reduce the concentration of ions and molecules in blood samples. Despite the success of GEF at cleaning samples prior to testing, the process has deficiencies. Agarose, the raw material for the gel used in the filtration process, is not cultivated, but instead is harvested from seaweed naturally grown in the ocean. This creates an undesirable supply risk due to fluctuations in weather, seasons, etc. As a natural product, the sourced seaweed material generally produces agarose that varies in properties, necessitating the need for extensive testing of new batches of source material. Another undesirable quality of GEF is the soft mechanical structure of the gel component, which leads to significant manufacturing challenges. Gel stability concerns also necessitate the need to refrigerate commercial products containing agarose during transportation and storage. The soft mechanical structure of gel makes prepackaged products containing agarose prone to tearing, leading to gel 'chunks' in the prepackaged sample wells and reservoirs. Pipetting errors due to the presence of gel chunks in such wells and reservoirs can impair sample testing in an automated system.

Due to these disadvantages, non-gel based methods (e.g., those that do not utilize agarose) were developed to prepare biological samples before the identification and antimicrobial susceptibility testing of microbial cells in the sample. An alternative to gel electro-filtration is to utilize solid state membranes in lieu of a gel matrix (e.g., a membrane not made of a gel such as agarose) to perform separation by size exclusion. Such sample preparation strategies that employ porous filter membranes are referred to herein as membrane-assisted purification ("MAP").

The working principle behind GEF is electrophoresis, which is the movement of charged objects in an electric field. With this approach, ions and charged molecules are separated from the sample volume by driving them to migrate into the gel matrix and away from the sample well. Without intending to be bound by theory, it is thought that electrophoresis is a contributor to MAP cleanup performance, but that diffusion and electro-osmosis also play a significant and potentially dominant role.

The examples disclosed herein highlight some modes of operation for MAP sample preparation. Common among them all is the solid state approach, which is easier for manufacturing and does not require refrigerated storage of packaged products. The manmade filter materials are highly reproducible and do not exhibit the large variation in performance that may be associated with naturally sourced agarose gel material. Finally, elimination of gel from commercially produced sample preparation kits reduces the chances for pipetting errors associated with gel 'chunks' in automated instruments that conduct microbial identification and antimicrobial testing of samples.

Exemplary MAP Device Description

The MAP device separates a sample volume from one or more fluid reservoirs via a filter membrane (referred to herein as a porous filter medium) as shown in FIGS. 10A-10C. FIGS. 10A, 10B and 10C provide top and side views of an embodiment of a sample well located between filter membranes of the porous filter medium that separate a sample from fluid reservoirs, each fluid reservoir having an opposing electrode. The porous filter medium can be made of various membrane materials, such as one or more of polyvinylidene fluoride (PVDC), polycarbonate (such has track-etched polycarbonate), nitrocellulose, nylon, polyethersulfone, and aluminum oxide. The pore sizes of the porous filter medium can be 200 nm to 20 μm in diameter, such as 100 nm to 2000 nm in diameter, 200 nm to 2000 nm in diameter, such as 200 nm, 400 nm, 800 nm or 2000 nm in diameter.

During the MAP process, the sample buffer is exchanged with the reservoir buffer. As the buffer exchange occurs, objects larger than the pore size of the porous filter medium are prevented from leaving the sample well (e.g., are retained in the sample well). The reservoir buffer may be tailored to achieve a desired objective. For example, a bacteria-containing patient sample can be added to the sample well and growth media could be used in the fluid reservoirs. In this embodiment, concentrations of unwanted material in the sample decrease and are replaced by growth media, while the sample well retains the relatively large pathogenic cells. The final result would be cells suspended in growth media and free of undesirable background contaminants, such as proteins.

The physical principles driving the MAP buffer exchange include a combination of diffusion, electrophoresis, and electro-osmosis. The choice in pH and salt concentrations of the reservoir buffer and upfront preparation of the sample can be adjusted to achieve the desired combination of these buffer exchange effects. Additionally, electrophoretic and electro-osmotic effects may be controlled via electrodes in the buffer reservoirs and sample well. A range of voltages can be applied to achieve the electrophoretic and electro-osmotic effects, for example AC or DC voltages ranging from about 1 V to about 200 V, 50 V to 125 V, 50 V to 100 V, 75 V to 100 V, or 85 V to 95 V, such as a DC voltage of 95 V.

Thus, provided herein are methods for purifying one or more microbial cells, such as one or more different genus or species of bacteria, in a biological sample. In some examples, at least two different genus and/or microbial species are purified (such as 2 to 50, 2 to 25, 2 to 20, 2 to 10, or 2 to 5 different genus and/or microbial species), such as *E. coli* and *Acinetobacter baumannii*, or *Klebsiella oxytoca* and *Klebsiella planticola*. Exemplary biological samples include cerebrospinal fluid, urine, a respiratory specimen, blood or plasma (other examples are provided herein). Such samples may contain undesirable contaminants, such as proteins, salt, or ions (or other reagents, such as those described above). The disclosed methods can include adding a biological sample containing contaminants and one or more microbial cells to a well disposed in a porous filter medium. The porous filter medium includes pores smaller than the one or more microbial cells, thereby preventing the one or more microbial cells from entering the porous filter medium. In some examples, the pore sizes of the porous filter medium are about 200 nm to 20 μm in diameter, such as about 100 nm to 2000 nm in diameter, about 200 nm to 2000 nm in diameter, such as 200 nm, 400 nm, 800 nm or 2000 nm in diameter. In some examples, the porous filter medium includes polyvinylidene fluoride, track-etched polycarbonate, nitrocellulose, nylon, polyethersulfone, or combinations thereof. The porous filter medium is contacted with a buffer disposed in one or more reservoirs adjacent to the porous filter medium to initiate diffusion. Exemplary buffers include those that include histidine and tris(hydroxymethyl)aminomethane, as well as the other examples described above. An electrical potential (such as AC or DC) is applied across the porous filter medium to cause the contaminants to enter the porous filter medium through one or more walls of the well, while retaining the one or more microbial cells in the well. In some examples, the electrical potential is applied for about 5 minutes to about 15 minutes, such as 10 to 12 minutes, such as 5, 6, 7, 8, 9, 10, 11, 12, 13, 14 or 15 minutes. In some examples, AC or DC voltages ranging from about 1 V to about 200 V, 50 V to 125 V, 50 V to 100 V, 75 V to 100 V, or 85 V to 95 V, such as a DC voltage of 95 V are used. In some examples, the electrical potential includes a field polarity and the field polarity is switched according to a programmed sequence. The method can further include applying a tangential flow to the porous filter medium to remove non-permeable contaminants from the surface of the porous filter medium. The method can further include concentrating in the well the one or more microbial cells. The method can also include subsequently removing the one or more microbial cells from the well. In some examples, the buffer is replenished prior to removing the one or more microbial cells from the well. In some examples, the adding step and the applying step are repeated one or more times (such as 1 to 100 times, 1 to 20 times, or 1 to 10 times, such as 1 2, 3, 4, 5, 6, 7, 8, 9 or 10 times) prior to removing the one or more microbial cells from the well.

In some examples, the biological sample is mixed, for example prior to or after adding the sample to the well (or both before and after). In some examples, the biological sample is mixed, for example before application of the electrical potential, during application of the electrical potential, after application of the electrical potential, or combinations thereof. Exemplary mixing methods include one or more of stirring the sample, repeatedly passing the sample through a pipette tip, and repeatedly forcing the sample through tubing connected to a syringe. In some examples, a chemical agent (such as one or more of those described above) is added to the biological sample to increase permeability of the porous filter medium to the contaminants.

In some examples, the disclosed methods can decrease the amount of one or more contaminants (such as protein, NADH, and/or salt) in the sample within about 10 to 15 minutes (such as within about 10, 11, 12, 13, 14 or 15 minutes) of applying the electrical potential. In some examples, the disclosed methods can decrease the amount of one or more contaminants (such as protein, NADH, and/or salt) in the sample by at least 25%, at least 30%, at least 40%, at least 45%, at least 50%, at least 55%, or at least 60% within about 10 to 15 minutes (such as within about 5, 6, 7, 8, 9, 10, 11, 12, 13, 14 or 15 minutes) of applying the electrical potential.

In some examples, the disclosed methods do not significantly alter the amount of the one or more microbes (such as bacterial cells) in the sample within about 10 to 15 minutes (such as within about 10, 11, 12, 13, 14 or 15 minutes) of applying the electrical potential. In some examples, the disclosed methods do not significantly alter the amount or number of the one or more microbes (such as bacterial cells), in the sample by more than 20%, 15%, 10%, or 5% (such as within about 5, 6, 7, 8, 9, 10, 11, 12, 13, 14 or 15 minutes) of applying the electrical potential.

EXAMPLES

The following examples are provided for illustration purposes and are not intended to limit scope. Other variants will be readily apparent to one of ordinary skill in the art and are encompassed by the appended claims.

The examples described below anticipate a wide range of specimen variability. Processes may be adapted to a given specimen type, for example, first homogenizing the specimen if desirable. Next an aliquot (sample) of the specimen may be obtained, and then purified, to remove debris and other interfering materials. Purification may be achieved by placing the sample in a medium containing a well and applying a potential laterally across the medium to retain cells and pass contaminants into the medium.

Example 1. Purification of Bacteria Cells from Respiratory Specimens

Gel Preparation 10 grams of agarose powder (SeaKem, LE Agarose) was mixed with 1 L of buffered solution containing 100 mM histidine (Sigma, H8000) and 2.5 mM Trizma® base (Sigma, T1503). The final concentration of agarose slurry was 1.0% (w/v). The solution was boiled to melt the agarose powder and the molten agarose was stored in liquid form at 40° C. until use.

Gel Casting

Those familiar in the art of gel slab electrophoresis recognize that solid inserts or combs are routinely used to create a void volume in a gel slab that is later utilized for sample loading. Gel electrophoresis combs are generally nominally 1-2 mm thick, capable of holding nominally 100 μL of sample volume. In this example, a custom equilateral V-shaped well was used. The well had sides 1 cm long and a thickness of nominally 0.6 mm (0.025"). The comb was inserted into a gel box container (E-C Apparatus, EC 250-90) and the box filled with the molten agarose submerging a portion of the comb. The agarose was allowed to cool to room temperature forming an agarose gel. The comb was removed from the solidified agarose and the void volume of the comb formed a well in the material. The V-shaped well enabled facile recovery of the sample volume from the well, described in further detail below.

Pretreatment of the Agarose Gel Medium

The gel box containing the agarose gel medium having triangular wells was placed in an electrophoresis apparatus and then submerged in a run buffer containing 100 mM histidine and 2.5 mM Trizma® base. A 250 volt potential was applied for 1 hr. The applied potential yielded 22 mA of current. The pretreated gels were removed from the electrophoresis apparatus and transferred to a closed container and stored submerged in fresh run buffer until use.

Specimen Homogenization

A remnant specimen having a known level of bacteria was homogenized by pouring into a syringe connected to 0.02" (0.5 mm) inner diameter PEEK tubing and forcing through the PEEK tubing 10 times at a flow rate of approximately 0.1 mL/sec to liquefy the specimens. The specimen was then filtered through 5 μm track etch polycarbonate filters (SPI Pore, E5013-MB). A 1 mL sample aliquot of the specimen was processed as described below. An aliquot of the specimen was also reserved as a control.

A control or a known clinical sample (e.g., with a known concentration of bacteria) can be compared to the unknown sample.

Assessment of the Sample

The sample was diluted to a final nominal bacterial concentration of $1.5 \times 10^3$ CFU/mL. 50 μL of the diluted sample was plated in triplicate on Mueller Hinton Agar (MHA) and placed in the incubator overnight. The number of colonies counted on the overnight incubated plates divided by the plated volume and multiplied by dilution factor yielded the actual number of input *Klebsiella oxytoca* bacteria in CFU/mL.

The sample was diluted 10-fold and the optical density read was acquired at 625 nm to assess the amount of particulate debris in the sample.

Sample Loading

The pretreated gels were placed in the gel box and apparatus, patted dry, and excess liquid was removed from the triangular wells using 0.2 mm thick flat capillary plastic pipette tips (Fisher 07-200-519). The well was filled with a 20 μL sample of the homogenized specimen.

Sample Treatment

Histidine/Tris run buffer was added to the apparatus so that the liquid level was below the top of the gel slab. The sample was electrophoresed for 5 minutes at 250 volts and the samples were hydrodynamically sheared by pipetting the sample volume up and down 5× using a capillary pipette tip. The samples were electrophoresed again for 5 minutes at 250 volts and the samples then hydrodynamically sheared by pipetting the sample volume up and down 5× using a capillary pipette tip.

Post-Treatment Assessment of Spiked Sample

The treated sample was diluted to a final concentration of $1.5 \times 10^3$ CFU/mL. 50 μL of the diluted sample was plated in triplicate on Mueller Hinton Agar (MHA) and place in the incubator overnight. The number of colonies counted on the overnight incubated plates divided by the plated volume and multiplied by dilution factor yielded the actual number of *Klebsiella oxytoca* bacteria recovered in CFU/mL.

The treated sample was diluted 10-fold and then the optical density read was acquired at 625 nm to assess the amount of particulate debris remaining in the sample.

Results

|  | Pre-Treatment Optical Density (OD) | Post-Treatment Optical Density (OD) | Fold Cleanup |
| --- | --- | --- | --- |
| MEDIA METHOD | 0.2841 | 0.065 | 4.35 |

Electrode Configuration and Circuit Details

The 20 μL of recovered sample volume was diluted with 40 μL of 10 mM ascorbic acid and then introduced into a flow cell (described below) for electrokinetic concentration.

For comparison purposes, a 20 μL of a non-treated sample was diluted with 40 μL of 10 mM ascorbic acid and then introduced into a flow cell (described below) for electrokinetic concentration.

Flow Cell Construction

Figure 4A:
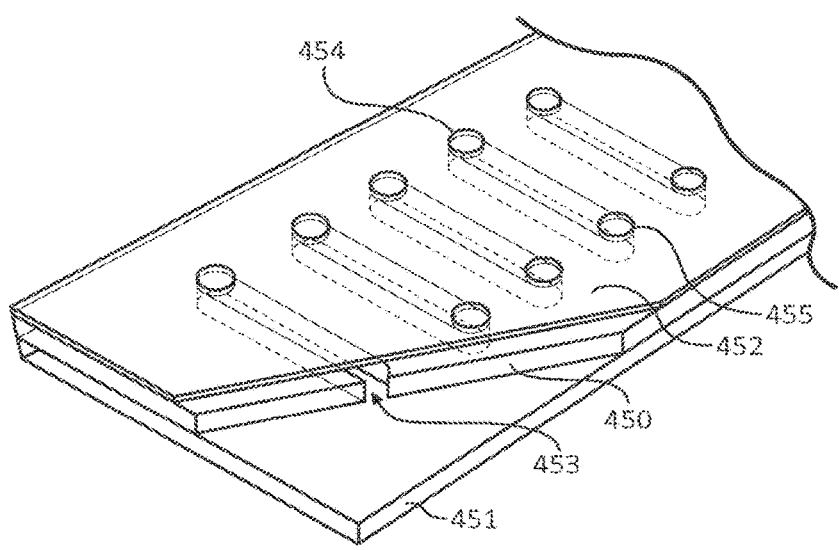
FIGS. 4A and 4B are a perspective view of multiple flow cell laminate assembly and a single flow cell cutaway view with corresponding electrode and circuit details used to create a potential across a medium.
Figure 4B:
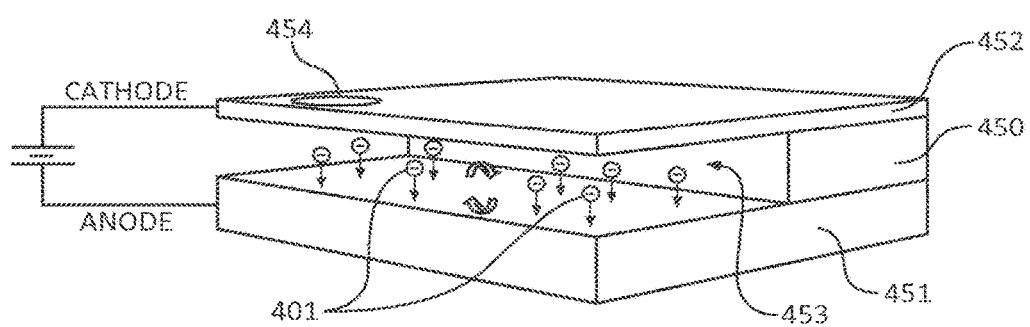

FIG. 4A is a perspective view of a multiple flow cell laminate flow cell assembly 400, and FIG. 4B is a single flow cell cutaway view with corresponding electrode and circuit details. Flow cells were assembled using a three layer die-cut laminate flow cell assembly 450 (DLE, Oceanside, Calif.), sandwiched between an indium tin oxide (ITO) coated glass slide flow cell floor 451 (Delta Technology, Stillwater, Minn.) and an ITO coated 5 mil polyester (ITO PET) plastic flow cell ceiling 452 (Sheldahl, Northfield, Minn.) forming a fluidic flow cell chamber. The laminate flow cell assembly contained 32 separate channels 453, each having 1.78 mm width×0.30 mm height×11.28 mm length, with 1.78 mm diameter fluidic inlet and outlet ports (454 and 455, respectively) to interface with plastic pipette tips for fluid exchanges using manual pipettors. The transparent top and bottom electrodes enabled microscope imaging.

Bacteria 401 suspended in redox active EKB were contacted with uniform transparent electrodes constructed from transparent ITO coated glass (Delta Technologies, Stillwater, Minn.) or polyester film (Sheldahl, Northfield, Minn.). A potential was applied to the conductive ITO surfaces completing the circuit, establishing a faradaic current and an electric field between the electrodes and enabling bacterial electrokinetic concentration (EKC) and surface capture, as illustrated in FIG. 4B.

Bacterial Suspension and Surface Concentration Experiments

Studies were performed by loading the flow cells with samples, with the power supply turned off, and then inserting the flow cells onto the microscope stage. The microscope acquired images at the bottom flow cell surface during subsequent steps. The power supply was connected and cells electrokinetically concentrated to the flow cell's bottom surface by application of a 1.4V DC fixed potential. The top electrode (flow cell ceiling) was connected to the negative power supply terminal, and the bottom electrode (flow cell floor) was connected to the positive terminal. The applied potential resulted in complete bacterial concentration in less than 3 minutes. After 300 seconds, a −1.0 V DC fixed potential was applied for an additional 60 seconds to measure the degree of irreversible binding of the sample debris and bacteria on the flow cell floor. The digital microscope acquired images every 3-7 seconds during concentration.

Digital Microscopy Setup

An Olympus IX-71 inverted microscope equipped with a 12-bit, 1200×1600 pixel array monochrome CCD digital camera (MicroFire, Leeds Precision Instruments, Minneapolis, Minn.) was used for image acquisition. The transmitted illumination cone, created with an IX-PH3 annular ring placed in a 0.55 NA transmitted light condenser, was 33.4° from the normal to the microscope's focal plane. The illumination cone, after refraction through the flow cell's air-glass-ITO-liquid interfaces (described below), resulted in a 24.5° forward scatter angle-of-incidence relative to the focal plane normal. The forward scatter angle-of-incidence relative to the flow cell's air-plastic-ITO-liquid interfaces was not calculated. In all formats, a dark image was obtained in the absence of scatterers, as the illumination cone passed outside the 20×, 0.4 NA microscope objective's (LCPlanFl Olympus, Leeds Precision Instruments) imaging cone. The presence of scatterers resulted in the appearance of bright objects on a dark image background (dark-field image for objects within the focal depth). The system field-of-view was 444×592 µm with corresponding 0.37 µm pixel resolution. The imaging system's depth-of-focus and image depth were 5.8 µm and 3.8 mm respectively. Constant camera exposure and gain settings were maintained when relative intensity comparisons were performed, as in the case of growth experiments described below.

Accumulation Time Results

Figure 5:
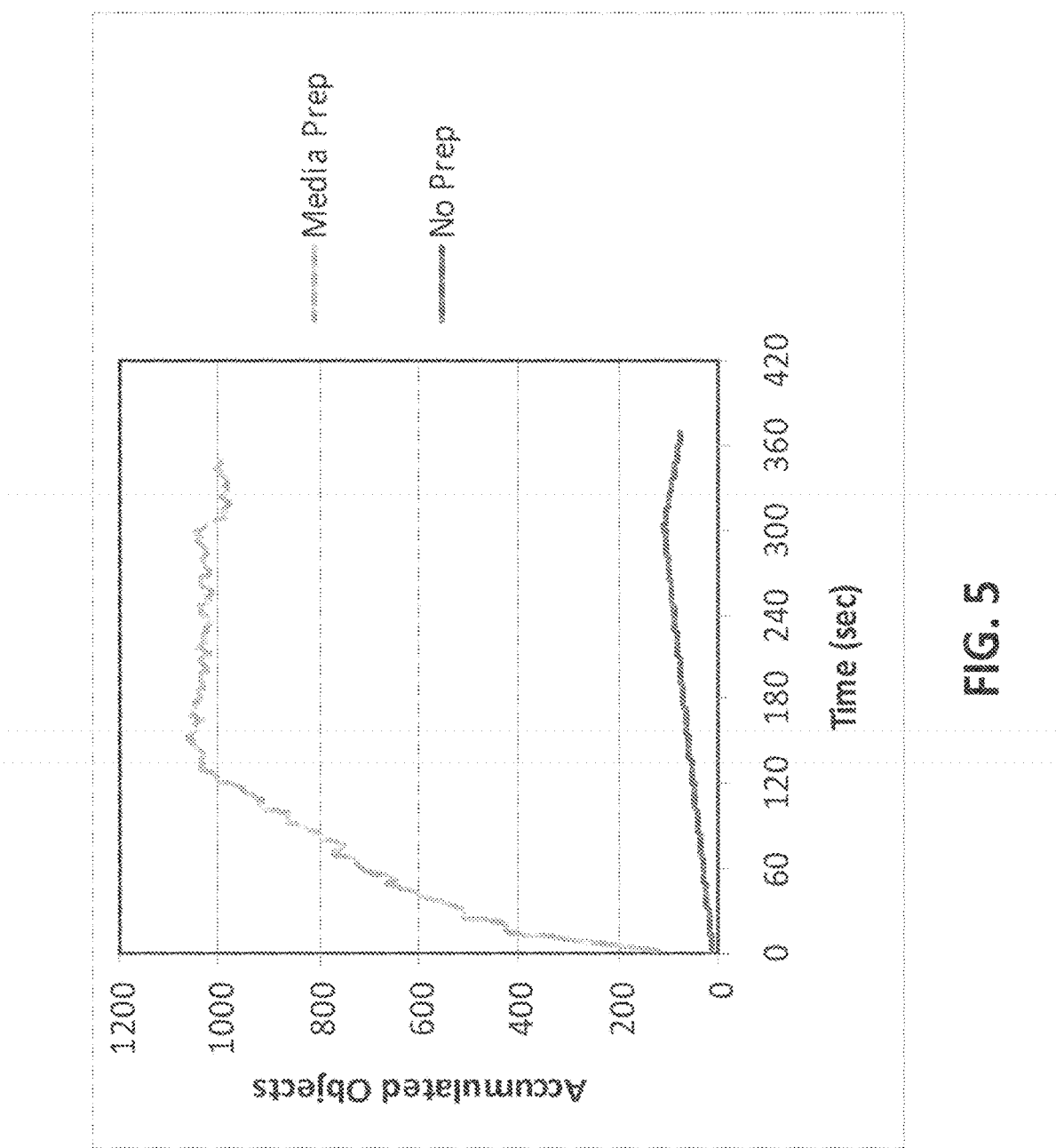
FIG. 5 is a graph showing results of accumulated objects (solid materials immobilized on a surface) over time for treated compared to non-treated samples.

FIG. 5 is a graph showing results of accumulated objects over time for treated compared to non-treated samples. The non-treated sample data is expected data.

The objects are solid material, such as cells, viruses, and cellular debris that are immobilized on a sample surface. FIG. 5 shows that material concentrates, and then adheres to, the surface. Subsequent processes, such as measuring the growth or growth rate, can be utilized to determine the number of viable cells, and additionally probing the material using receptor-ligand binding techniques, including, but not limited to, antibody recognition or nucleic acid hybridization methods can be used to measure the abundance of microorganisms present.

Figure 6A:
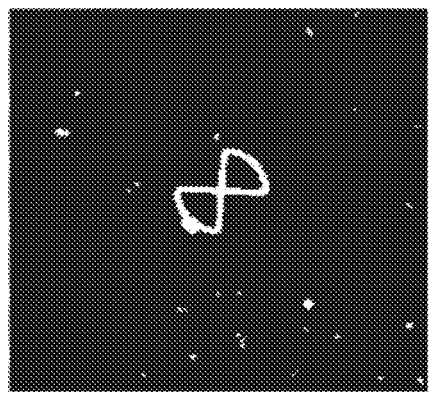
FIGS. 6A, 6B and 6C depict microscopic images of non-treated samples over time.
Figure 6B:
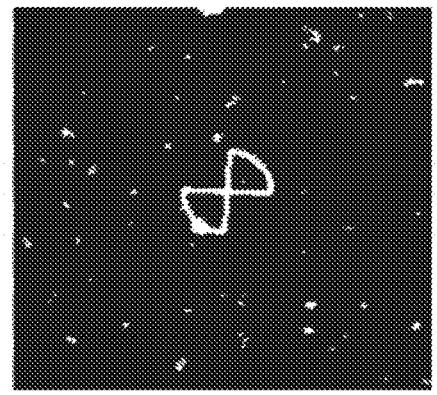
Figure 6C:
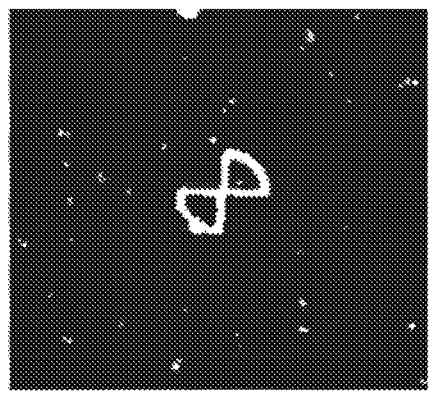

FIGS. 6A, 6B and 6C depict microscopic images of non-treated samples at initial time, time of 300 seconds, and time of 360 seconds, respectively. The surface accumulation rate is low. As shown in FIGS. 6A, 6B and 6C, poor surface retention of the objects occurs when samples are not treated.

Figure 7A:
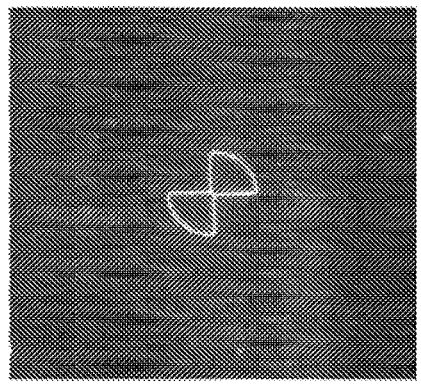
FIGS. 7A, 7B and 7C depict microscopic images of treated samples over time.
Figure 7B:
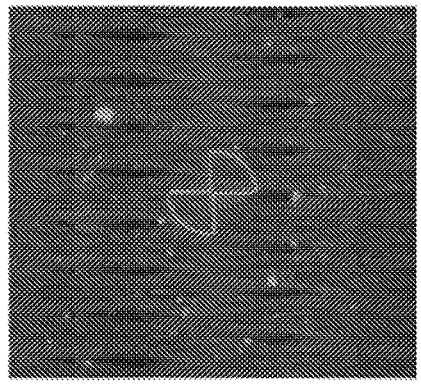
Figure 7C:
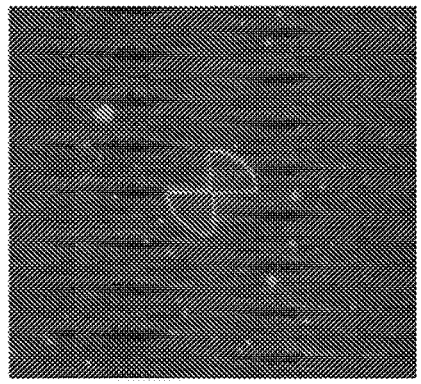

FIGS. 7A, 7B and 7C depict microscopic images of treated samples at initial time, time of 300 seconds, and time of 360 seconds, respectively. The treated sample surface accumulates all objects, as evidenced by a plateau occurring in less than 3 minutes. As shown in FIGS. 7A, 7B and 7C, the objects were irreversibly bound to the surface, as evidenced by consistent accumulated counts during reverse electrophoresis.

Bacterial Growth

After cell immobilization, the flow cell was rinsed with 10 times the internal cell volume of 1/10th strength cation-adjusted Mueller-Hinton Broth (CAMHB) growth media (Difco, Sparks, Md.). 100 µL of liquefied Mueller Hinton Agar (MHA) was loaded into the flow cell and then cooled to room temperature, solidifying into a hydrogel.

Time Lapse Imaging

Direct observation of bacterial growth was performed by inserting the disposable 32-channel flow cell assembly into a custom benchtop automated instrument that combined digital microscopy, motion control, and image analysis software. The system was enclosed in an incubator maintained at 35° C. The motorized microscope stage enabled automated XY translation, location logging, and memory with 10 µm repeatability. The system automatically focused and acquired surface images of adherent bacteria at programmed time intervals for multiple fields-of-view during an experiment. The system used the fiducial markings to autofocus and mechanically align (±1 pixel) the fields-of-view prior to image acquisition. Unless stated otherwise, a single field-of-view contained sufficient numbers of cells for analysis, and automated analysis routines counted the number of growing clones.

Growth Results

The number of growing clones observed using the digital microscope method was compared with the number of expected growing clones, assuming 100% yield and a 1 to 1 correlation between growing colonies on MHA plates, to calculate a digital microscopy method efficiency. The medium method was compared to an alternative medium method wherein the gel was submerged. A total efficiency was calculated by multiplying the treatment recovery and digital microscopy efficiency.

|  | Post Treatment Recovery | Digital Microscopy EFF | Total EFF |
| --- | --- | --- | --- |
| Control - No Prep | 100% | 12% | 12% |
| Medium Method | 82% | 90% | 74% |
| Submerged Medium Method | 43% | 100% | 43% |

The total efficiency for the medium method was highest when the gel slab was not submerged.

Example 2. Purification of Bacterial Cells from Blood Culture Specimens Utilizing Passive Membrane-Assisted Purification This Example describes experiments exploring the preparation of clinically relevant bacteria-containing blood samples for analysis in an automated microbial identification and antimicrobial susceptibility instrument. Results are shown utilizing MAP devices comprising structures that resemble tubs with various membranes comprising various pore sizes and material types.

Preparation of MAP Devices

The MAP devices used contain three fluidic regions separated by filter paper membranes. In one set of experiments, various types of paper filter membranes were used (polycarbonate, polyvinylidene fluoride (PVDF), nitrocellulose, nylon, polyethersulfone) while keeping the pore size approximately constant. In another set of experiments, various pore sizes were tested while keeping the material type constant. Each reservoir was filled with 6.1 mL of 12.5 mM L-histidine for all experiments.

Preparation of Sample

Clinically relevant samples were prepared to mimic positive blood cultures as they appear in the clinical lab. A 0.5 McFarland sample of *Acinetobacter baumannii* (ATCC 19606) was prepared in 90% saline solution. The solution was diluted 1:20 (vol:vol) with donor blood, and then 10 mL of the resulting solution was added to a commercially available blood culture bottle. The blood culture bottle was incubated in a related blood culture instrument until the instrument flagged the bottle as positive for bacteria (typically in about 10 hours with a resulting cell concentration of $10^8$ CFU/mL). After positivity was determined, the solution from the bottle culture bottle was diluted 1:30 (vol:vol) with 12.5 mM L-Histidine. The MAP sample wells were emptied of buffer fluid (if any was present) and the sample solution was added to the sample well of each MAP device. Unused sample was retained for use as a control for future quantification of protein and bacterial cell concentrations.

Filtration

Each MAP device was allowed to sit on a laboratory bench at room temperature while sample filtration occurred. During the filtration process, sample buffer exchanged with the 12.5 mM L-histidine buffer of the reservoirs flanking both sides of the sample well. To quantify filtration performance versus time, 10 µL aliquots were removed periodically (approximately every 10 minutes) from each device's sample well and absorbance data was immediately collected on a Nanodrop 2000 UV-Vis spectrophotometer.

Figures 11A, 11B, 11C:
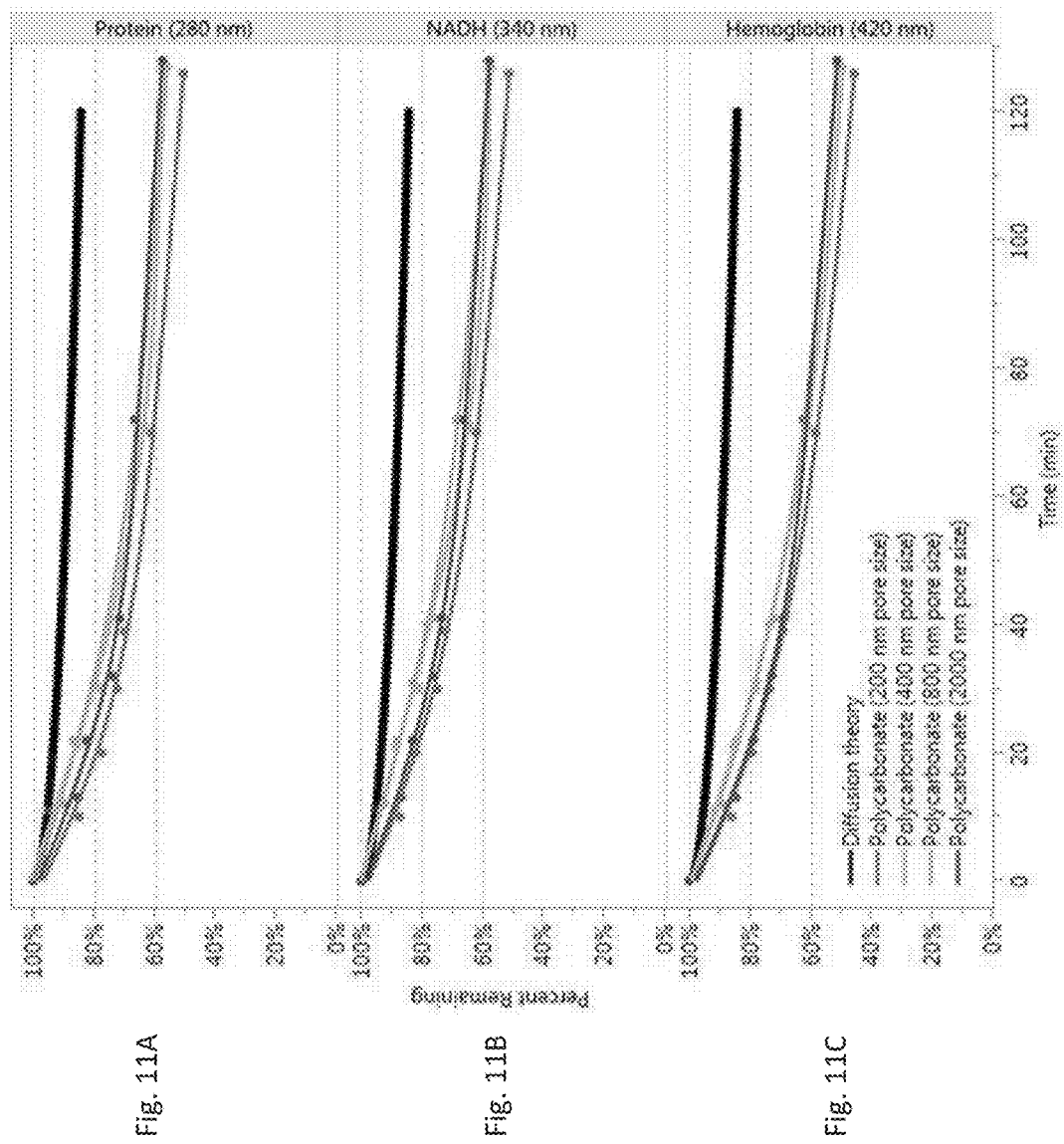
FIGS. 11A, 11B and 11C show spectrophotometric profiles of a sample subjected to membrane assisted purification using membrane pore sizes of 200 nm, 400 nm, 800 nm, and 2000 nm. Absorbance at (A) 280 nm was used to infer relative concentration of protein, (B) 340 nm was used to infer relative concentration of NADH, and (C) 420 nm was used to infer relative concentration of hemoglobin.

FIGS. 11A, 11B and 11C show spectrophotometric profiles of a sample subjected to membrane assisted purification using polycarbonate membranes with pore sizes of 200 nm, 400 nm, 800 nm, or 2000 nm. Absorbance at 280 nm was used to infer relative concentration of protein (FIG. 11A), 340 nm was used to infer relative concentration of NADH (FIG. 11B), and 420 nm was used to infer relative concentration of hemoglobin (FIG. 11C). The top line in each graph illustrates the theoretical expectation based on diffusion at room temperature utilizing a diffusion coefficient of $D=1 \times 10^{-10}$ $m^2s^{-1}$ and assuming ideal filters (porosity=1). Over two hours of diffusion, the MAP device reduced sample concentrations of protein, NADH, and hemoglobin by approximately 50% of their starting values (FIGS. 11A-C). FIGS. 11A-C also display the theoretical cleanup profile as expected from Fick's $2^{nd}$ law of diffusion (top line in each graph). The MAP devices exhibit cleanup speeds significantly faster than expected from a diffusion alone. Thus, physical mechanisms drive the fast filtration speeds. One explanation for this observation is that 'built in' electric fields due to pH mismatch between the sample and buffer reservoirs might lead to electro-osmotic and electrophoretic effects that act to enhance filtration speeds. Another contributing factor could be convective mixing in the sample well, which could lead to steeper concentration gradients at the filter membrane which would lead to faster diffusion of material out of the sample well.

Figures 12A, 12B, 12C:
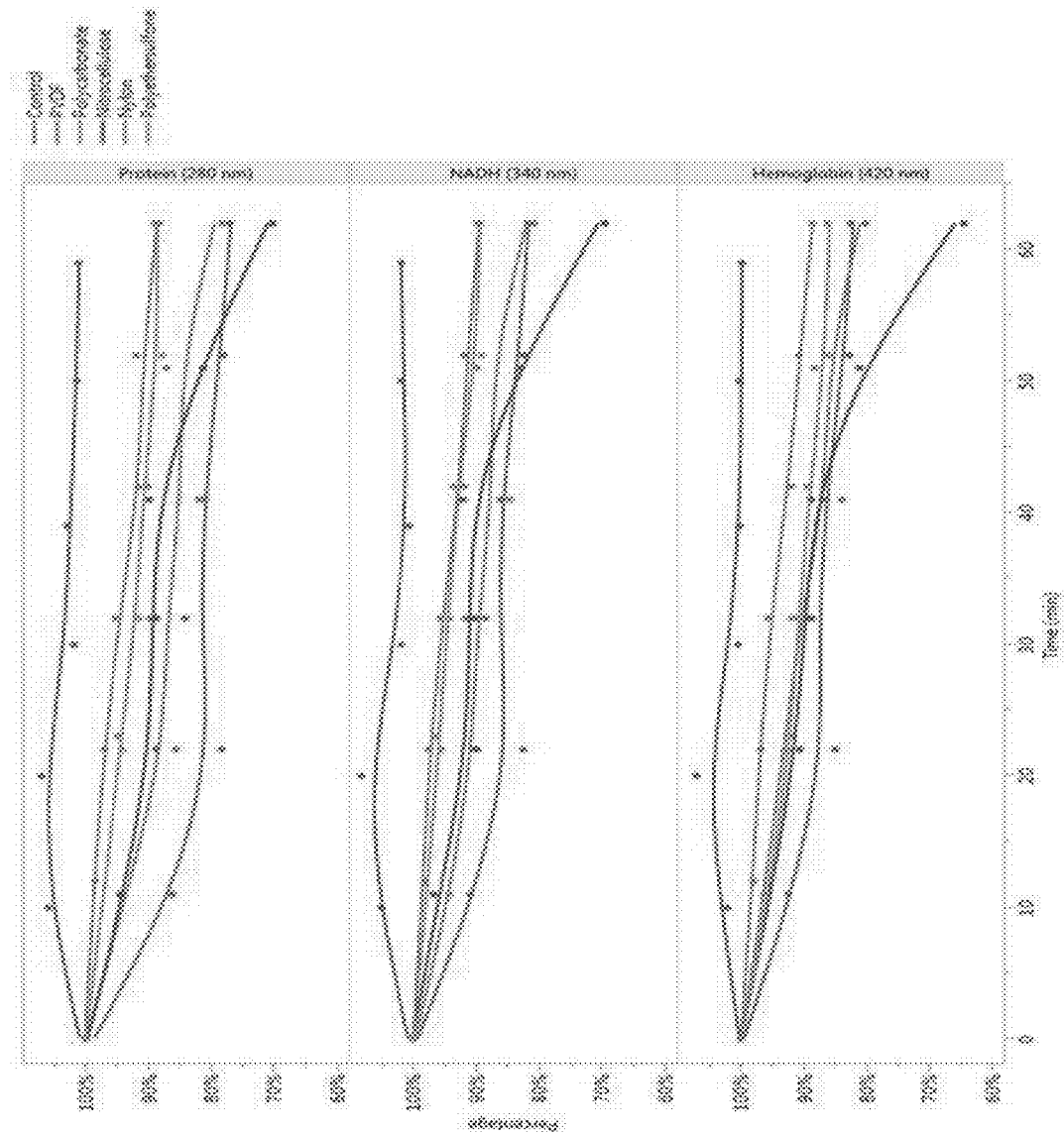
FIGS. 12A, 12B and 12C show spectrophotometric profiles of a sample subjected to membrane assisted purification using different membrane materials while maintaining pore size at around 200 nm. Absorbance at (A) 280 nm was used to infer relative concentration of protein, (B) 340 nm was used to infer relative concentration of NADH, and (C) 420 nm was used to infer relative concentration of hemoglobin.

FIGS. 12A-C show results from a second set of experiments wherein pore size was kept approximately constant (200 nm or 220 nm) while the following membrane material types were used: polyvinylidene fluoride (PVDF), track-etched polycarbonate, nitrocellulose, nylon, and polyethersulfone. All filters used a pore size of 220 nm, except nylon and polycarbonate which used a pore size of 200 nm. The spectrophotometric profiles of FIGS. 12A, 12B and 12C show MAP cleanup profiles in comparison to a control sample (top line in each graph) prepared identically but which did no undergo MAP filtration.

Figure 13:
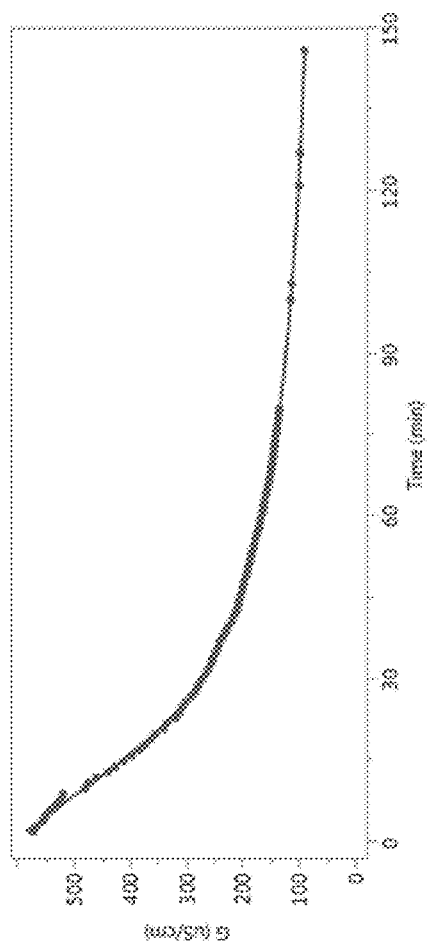
FIG. 13 depicts the time evolution of decreasing sample conductivity resulting from membrane assisted purification using polycarbonate filters having a 200 nm pore size.

FIG. 13 depicts the time evolution of decreasing sample conductivity resulting from membrane assisted purification using polycarbonate filters having a 200 nm pore size. In this experiment, the blood culture specimen was *Escherichia coli* (ATCC 25922). The decreasing conductivity indicates that the salt concentration is decreasing.

Cell Retention

Post-filtration bacterial cell concentrations were quantified and compared to unfiltered control samples. This was accomplished using a staining assay performed in an automated instrument system designed to identify microorganisms in patient samples and determine antimicrobial susceptibility of the identified microorganisms. The automated assay begins with electrokinetic capture of cells for subsequent microscopic imaging as described in Example 1. Each sample was diluted 1:1 by volume in 2 mM L-dopa, followed by loading each sample into a series of microfluidic flow channels (5 channels per sample, 20 µL per flow channel). Electrokinetic capture was then performed by applying 1.6 V for 5 minutes between two indium tin oxide (ITO) electrodes located on opposing sides of the sample volume. Cells migrate under the influence of the resulting electric field and are captured on the poly-L-lysine coated ITO anode. After electrokinetic capture the flow channel volumes were washed with 80% ethanol and allowed to sit for 5 minutes to facilitate permeabilization of the cell wall. Lastly, each flow channel was rinsed with 1 µM propidium iodide stain, after which each flow channel was imaged under the instrument system's fluorescence microscope. Twenty-four fluorescence images were collected per flow channel, comprising 14 $mm^2$ of imaging area per channel. Imaging was performed under 520 nm green laser illumination and image collection was through a bandpass filter around 590 nm in order to clearly resolve fluorescently labeled cells. The instrument system's automated image analysis was employed to count individual cells in the fluorescent images.

Figure 14:
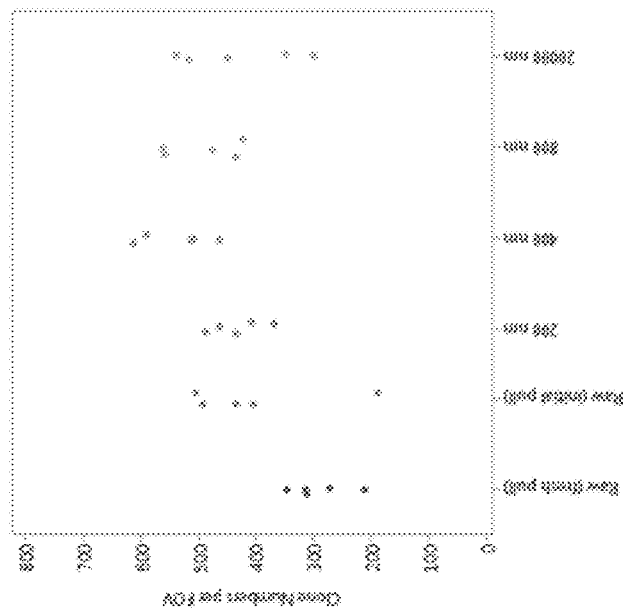
FIG. 14 depicts enhanced bacterial cell densities in samples subjected to membrane assisted purification as compared to unfiltered control samples.

FIG. 14 depicts enhanced bacterial cell densities in samples subjected to membrane assisted purification as compared to unfiltered control samples. Bacterial cell concentrations in post-filtration MAP samples and two control samples were determined by the automated instrument system. Bacterial cells were localized on glass within individual flow channels, stained, and imaged. Each field of view ("FOV") represents 0.585 $mm^2$. As shown in FIG. 14, bacterial cell concentrations following membrane assisted purification are comparable to the unfiltered control samples. This indicates that even as the protein and salt concentrations decrease in the sample (e.g., contaminants are removed), the bacterial cell concentrations remain constant (e.g., bacterial cells are not significantly removed).

Example 3. Purification of Bacteria Cells from Blood Culture Specimens Utilizing Active Membrane-Assisted Purification Example 2 provides results from MAP processes that do not utilize external control of the electrical environment during sample cleaning. The incorporation of electrodes into the process allows for additional control over the electrophoretic and electro-osmotic effects which can change the rate of buffer exchange.

Preparation of MAP Devices

MAP devices were prepared as in Example 2, but with the addition of a gold coated stainless steel electrode located in each of the two buffer reservoirs on either side of the sample well as depicted in FIGS. 10A, 10B, and 10C.

Preparation of Sample

Sample preparation was similar to Example 2, but an *Escherichia coli* (ATCC 25922) isolate was cultured in a commercially available blood culture bottle. After establishing blood culture bottle positivity, the sample was diluted 1:1 in Mueller-Hinton Broth and then 1:20 in 12.5 mM L-Histidine containing 0.01% sodium dodecyl sulfate before loading into the MAP sample well defined between membrane filters.

Filtration

Figures 15A, 15B, 15C:
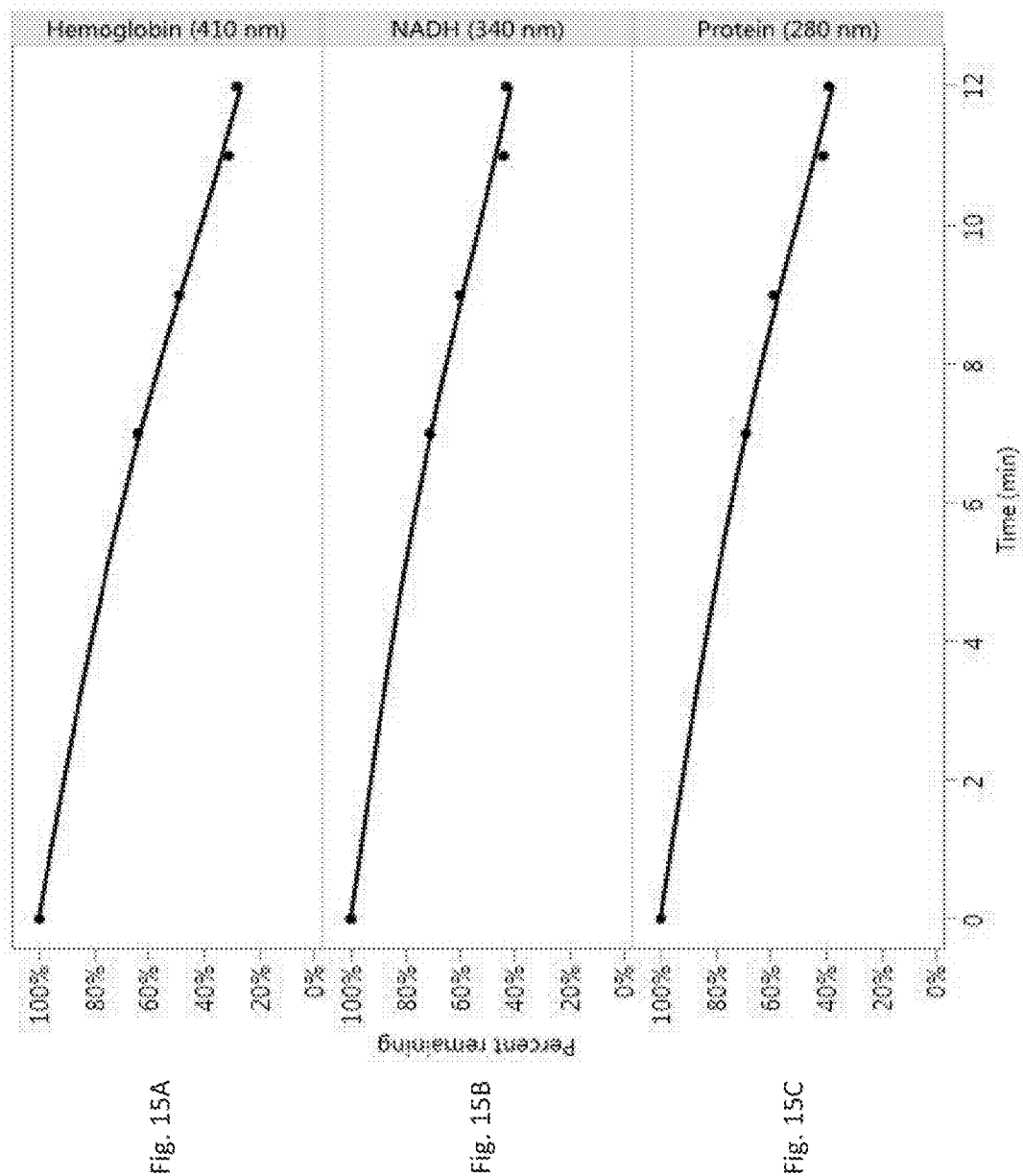
FIGS. 15A, 15B and 15C depict spectrophotometric measurements indicating a reduction of background ions and molecules over time in an *Escherichia coli* blood sample subjected to membrane assisted purification enhanced with a 95 volt charge. Absorbance at (A) 420 nm was used to infer relative concentration of hemoglobin, (B) 340 nm was used to infer relative concentration of NADH, and (C) 280 nm was used to infer relative concentration of protein.

A MAP device was allowed to sit on a laboratory bench at room temperature with a 95 V bias maintained across the two gold electrode pins situated in the buffer reservoirs of the MAP device, as illustrated in FIGS. 10A-10C. To quantify filtration performance versus time, 10 µL aliquots were removed periodically from the device's sample well and absorbance data was collected on a Nanodrop 2000 UV-Vis spectrophotometer. Absorbance at 280 nm was used to infer relative concentration of protein, 340 nm was used to infer relative concentration of NADH, and 420 nm was used to infer relative concentration of hemoglobin. FIGS. 15A, 15B and 15C depict spectrophotometric measurements indicating a reduction of background (e.g., contaminating) ions and molecules over time in an *Escherichia coli* blood sample subjected to membrane assisted purification with a 95 Volts applied across the electrodes. FIG. 15A shows a reduction of hemoglobin contaminants in the blood sample over the 12 minute reaction period. Likewise, FIG. 15B shows a reduction in sample NADH concentration and FIG.

15C shows a reduction in sample protein concentration over 12 minutes of voltage exposure.

Figure 16:
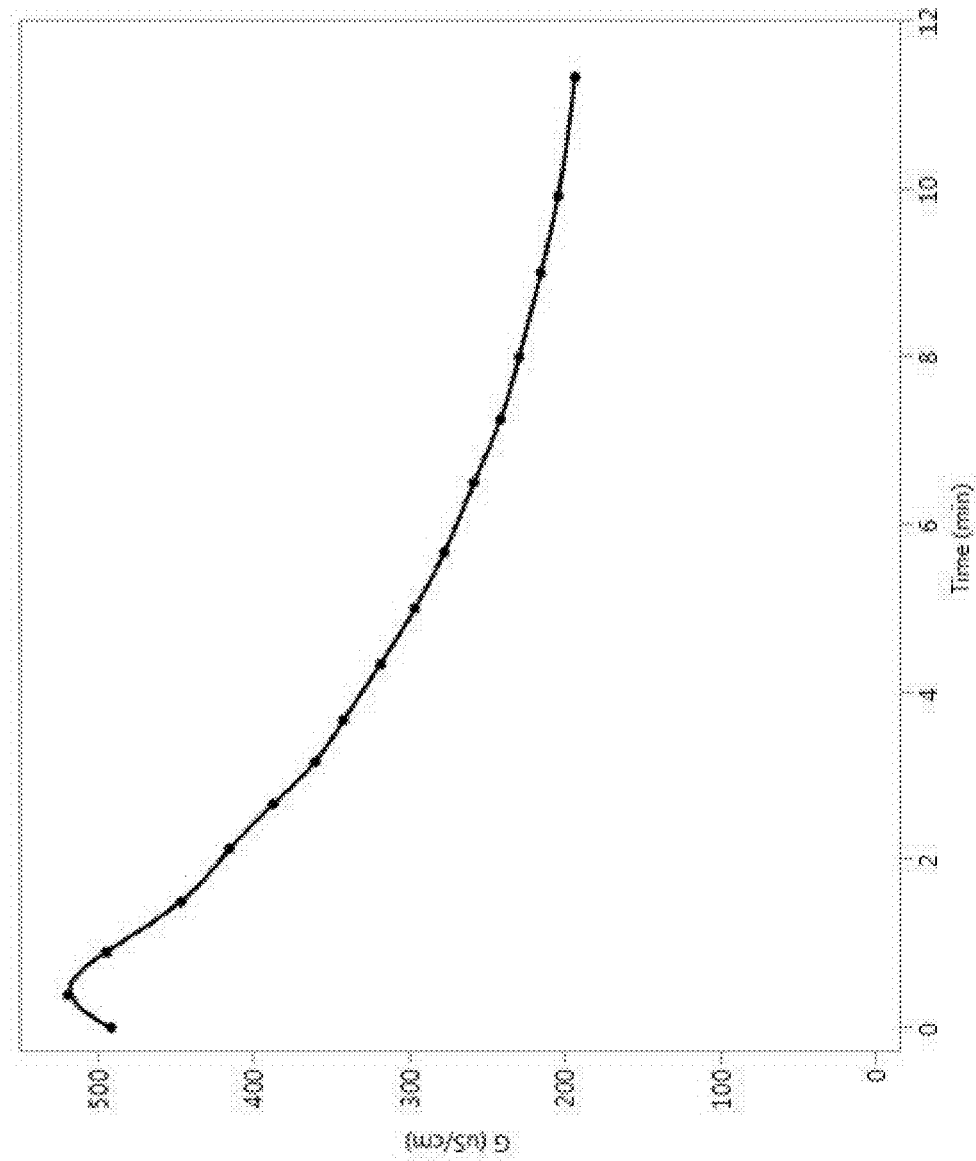
FIG. 16 shows sample conductance versus time for a *Proteus vulgaris* sample that was subjected to membrane assisted purification enhanced with the application of 95 volts for about 12 minutes.

FIG. 16 shows sample conductance versus time for a similar experiment utilizing a *Proteus vulgaris* isolate grown in a commercially available blood culture bottle, and then subjected to a 1:27 (vol:vol) dilution in 12.5 mM L-Histidine after bottle positivity and before loading into a MAP device. The results depicted in FIG. 16 show that sample conductance decreased substantially for a *Proteus vulgaris* sample that was subjected to membrane assisted purification enhanced with the application of 95 V for about 11 minutes.

The amount of contaminating salt removed from the blood sample during the MAP process that included exposure to 95 V for about 11 min (FIG. 16) was comparable to 30 min when no voltage was applied (FIG. 13). Likewise, the level of sample protein cleanup performance for about 7 minutes at 95 V (FIG. 15C) is comparable to 2 hours when no voltage is applied (FIG. 11A). Thus, the addition of an electrical voltage reduces the time needed to achieve sample purification using a membrane medium over diffusion alone. The choice of buffer, voltage, and porous filter material may be modified or adjusted to achieve the desired reduction of contaminants and cleanup time. In some examples, MAP processes are conducted for about 5 minutes to about 15 minutes, depending upon the choice of buffer, voltage, pore size and/or membrane type.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily imply that two elements are directly connected and in fixed relation to each other. The exemplary drawings are for purposes of illustration only, and the dimensions, positions, order and relative sizes reflected in the drawings attached hereto may vary.

Numerous and varied other arrangements can be readily devised by those skilled in the art without departing from the spirit and scope of the description. Moreover, all statements herein reciting principles, aspects and embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. All references cited herein are incorporated by reference in their entirety.

The invention claimed is:

1. A method of purifying one or more microbial cells in a biological sample, comprising:
    adding a biological sample containing contaminants and one or more microbial cells to a well disposed in a porous filter medium, wherein the porous filter medium comprises pores smaller than the one or more microbial cells, thereby preventing the one or more microbial cells from entering the porous filter medium;
    contacting the porous filter medium with a buffer disposed in one or more reservoirs adjacent to the porous filter medium to initiate diffusion;
    applying an electrical potential across the porous filter medium to cause the contaminants to enter the porous filter medium through one or more walls of the well, while retaining the one or more microbial cells in the well; and
    removing the one or more microbial cells from the well.

2. The method of claim 1, wherein the one or more microbial cells are bacteria.

3. The method of claim 1, wherein the biological sample comprises cerebrospinal fluid or urine.

4. The method of claim 1, wherein the biological sample comprises blood or plasma.

5. The method of claim 1, wherein the biological sample comprises a respiratory specimen.

6. The method of claim 1, wherein the electrical potential is applied for about 5 minutes to about 15 minutes.

7. The method of claim 1, wherein the buffer is replenished prior to removing the one or more microbial cells from the well.

8. The method of claim 7, wherein the buffer comprises histidine and tris(hydroxymethyl)aminomethane.

9. The method of claim 1, further comprising adding a chemical agent to the biological sample to increase permeability of the porous filter medium to the contaminants.

10. The method of claim 1, further comprising applying a tangential flow to the porous filter medium to remove non-permeable contaminants from the surface of the porous filter medium.

11. The method of claim 1, further comprising concentrating in the well the one or more microbial cells.

12. The method of claim 11, further comprising repeating the adding step and the applying step prior to removing the one or more microbial cells from the well.

13. The method of claim 1, further comprising mixing the biological sample.

14. The method of claim 13, wherein the biological sample is mixed by stirring the sample, repeatedly passing the sample through a pipette tip, repeatedly forcing the sample through tubing connected to a syringe, or combinations thereof.

15. The method of claim 13, wherein the biological sample is mixed before application of the electrical potential, during application of the electrical potential, after application of the electrical potential, or combinations thereof.

16. The method of claim 1, wherein the electrical potential comprises a field polarity and the field polarity is switched according to a programmed sequence.

17. The method of claim 1, wherein the porous filter medium comprises polyvinylidene fluoride, track-etched polycarbonate, nitrocellulose, nylon, polyethersulfone, or combinations thereof.

18. The method of claim 1, wherein the pores of the porous filter medium are about 200 nm to about 2000 nm in diameter.

* * * * *